US012691086B2

(12) United States Patent
Ali et al.

(10) Patent No.: US 12,691,086 B2
(45) Date of Patent: Jul. 28, 2026

(54) METHODS OF TREATING SYSTEMIC SCLEROSIS AND IDIOPATHIC PULMONARY FIBROSIS

(71) Applicant: HORIZON THERAPEUTICS IRELAND DAC, Dublin (IE)

(72) Inventors: Farah Naseer Ali, Dublin (IE); Paul Peloso, Dublin (IE)

(73) Assignee: HORIZON THERAPEUTICS IRELAND DAC, Dublin (IE)

( * ) Notice: Subject to any disclaimer, the term of this patent is extended or adjusted under 35 U.S.C. 154(b) by 578 days.

(21) Appl. No.: 18/177,487

(22) Filed: Mar. 2, 2023

(65) Prior Publication Data

US 2023/0414547 A1 Dec. 28, 2023

Related U.S. Application Data

(60) Provisional application No. 63/315,793, filed on Mar. 2, 2022.

(51) Int. Cl.

| | |
|---|---|
| ***A61K 31/196*** | (2006.01) |
| ***A61K 31/4418*** | (2006.01) |
| ***A61K 31/496*** | (2006.01) |
| ***A61P 11/00*** | (2006.01) |

(52) U.S. Cl.
CPC ........ *A61K 31/196* (2013.01); *A61K 31/4418* (2013.01); *A61K 31/496* (2013.01); *A61P 11/00* (2018.01); *C07B 2200/13* (2013.01)

(58) Field of Classification Search
CPC ................ A61K 31/192; A61K 31/196; A61K 31/4418; A61K 31/496; A61K 31/506; A61P 11/00; A61P 17/00
See application file for complete search history.

(56) References Cited

U.S. PATENT DOCUMENTS

| | | | |
|---|---|---|---|
| 5,571,506 | A | 11/1996 | Regan et al. |
| 6,225,352 | B1 | 5/2001 | Horwell et al. |
| 6,375,986 | B1 | 4/2002 | Ryde et al. |
| 6,431,478 | B1 | 8/2002 | Reed et al. |
| 6,582,285 | B2 | 6/2003 | Czekai et al. |
| 6,592,903 | B2 | 7/2003 | Ryde et al. |
| 6,656,971 | B2 | 12/2003 | Wu et al. |
| 6,742,734 | B2 | 6/2004 | Reed et al. |
| 6,745,962 | B2 | 6/2004 | Reed et al. |
| 6,861,448 | B2 | 3/2005 | Brouillette et al. |
| 6,953,857 | B2 | 10/2005 | Nazare et al. |
| 6,969,529 | B2 | 11/2005 | Bosch et al. |
| 6,976,647 | B2 | 12/2005 | Reed et al. |
| 6,991,191 | B2 | 1/2006 | Reed et al. |
| 7,067,665 | B2 | 6/2006 | Nazare et al. |
| 7,084,136 | B2 | 8/2006 | Tanimoto et al. |
| 7,208,601 | B2 | 4/2007 | Mjalli et al. |
| 7,244,451 | B2 | 7/2007 | Bosch et al. |
| 7,288,267 | B2 | 10/2007 | Bosch et al. |
| 7,459,472 | B2 | 12/2008 | Mjalli et al. |
| 7,465,825 | B2 | 12/2008 | Van Zandt et al. |
| 7,501,538 | B2 | 3/2009 | Mjalli et al. |
| 7,521,068 | B2 | 4/2009 | Bosch et al. |
| 7,575,184 | B2 | 8/2009 | Reed et al. |
| 7,695,739 | B2 | 4/2010 | Cooper et al. |
| 7,713,551 | B2 | 5/2010 | Mcgurk et al. |
| 7,842,232 | B2 | 11/2010 | Bosch et al. |
| 8,309,136 | B2 | 11/2012 | Cooper et al. |
| 8,362,073 | B2 | 1/2013 | Schaefer et al. |
| 8,367,805 | B2 | 2/2013 | Chamberlain et al. |
| 8,445,530 | B2 | 5/2013 | Schaefer et al. |
| 8,802,720 | B2 | 8/2014 | Schaefer et al. |
| 9,328,071 | B2 | 5/2016 | Schaefer et al. |
| 9,345,665 | B2 | 5/2016 | Ryde et al. |
| 9,974,746 | B2 | 5/2018 | Ryde et al. |
| 9,974,747 | B2 | 5/2018 | Ryde et al. |
| 9,974,748 | B2 | 5/2018 | Ryde et al. |
| 2002/0165275 | A1 | 11/2002 | Wu et al. |
| 2002/0198195 | A1 | 12/2002 | Nazare et al. |
| 2003/0083269 | A1 | 5/2003 | Brouillette et al. |
| 2004/0024019 | A1 | 2/2004 | Tanimoto et al. |
| 2004/0157919 | A1 | 8/2004 | Wu et al. |
| 2005/0049310 | A1 | 3/2005 | Mjalli et al. |
| 2005/0059713 | A1 | 3/2005 | Mjalli et al. |
| 2005/0165058 | A1 | 7/2005 | Nazare et al. |
| 2005/0171148 | A1 | 8/2005 | Mjalli et al. |
| 2006/0122257 | A1 | 6/2006 | Van Zandt et al. |

(Continued)

FOREIGN PATENT DOCUMENTS

| | | | |
|---|---|---|---|
| EP | 1217000 | A1 | 6/2002 |
| EP | 1349847 | B1 | 4/2005 |

(Continued)

OTHER PUBLICATIONS

Allanore et al. Lysophosphatidic Acid Receptor 1 Antagonist SAR100842 for Patients With Diffuse Cutaneous Systemic Sclerosis: A Double-Blind, Randomized, Eight-Week Placebo-Controlled Study Followed by a Sixteen-Week Open-Label Extension Study. Arthritis Rheumatol 70(10):1634-1643 (Oct. 2018).
Berge et al. Pharmaceutical Salts. Journal of Pharmaceutical Sciences 66(1):1-19 (Jan. 1977).
Birring et al., Development of a symptom specific health status measure for patients with chronic cough: Leicester Cough Questionnaire (LCQ). Thorax. 58:339-43 (2003).
Brooks et al. Limited fibrosis accompanies triple-negative breast cancer metastasis in multiple model systems and is not a preventive target. Oncotarget 9(34):23462-23481 (2018).
Byrn et al. Chapter II: Hydrates and Solvates. Solid-State Chemistry of Drugs, 2nd edition pp. 233-248 (1999).

(Continued)

*Primary Examiner* — Sarah Pihonak
(74) *Attorney, Agent, or Firm* — MARSHALL, GERSTEIN & BORUN LLP

(57) ABSTRACT

Described herein are uses of crystalline forms of 2-(4-methoxy-3-(3-methylphenethoxy)benzamido)-2,3-dihydro-1H-indene-2-carboxylic acid in the treatment of diseases or conditions that would benefit by administration with an LPA1 receptor antagonist compound.

19 Claims, 26 Drawing Sheets

(56) References Cited

U.S. PATENT DOCUMENTS

| | | | |
|---|---|---|---|
| 2009/0076070 | A1 | 3/2009 | Harada et al. |
| 2009/0124654 | A1 | 5/2009 | Mjalli et al. |
| 2010/0267778 | A1 | 10/2010 | Kusuda et al. |
| 2011/0152290 | A1 | 6/2011 | Schaefer et al. |
| 2013/0030008 | A1 | 1/2013 | Schaefer et al. |
| 2013/0225605 | A1 | 8/2013 | Schaefer et al. |
| 2014/0309264 | A1 | 10/2014 | Schaefer et al. |
| 2015/0031708 | A1 | 1/2015 | Hadida-Ruah et al. |
| 2022/0064105 | A1 | 3/2022 | Pernerstorfer et al. |
| 2023/0147835 | A1 | 5/2023 | Peloso et al. |

FOREIGN PATENT DOCUMENTS

| | | | |
|---|---|---|---|
| WO | WO-9220350 | A1 | 11/1992 |
| WO | WO-9806691 | A2 | 2/1998 |
| WO | WO-0194309 | A1 | 12/2001 |
| WO | WO-0207516 | A2 | 1/2002 |
| WO | WO-02051831 | A1 | 7/2002 |
| WO | WO-02059080 | A2 | 8/2002 |
| WO | WO-03006628 | A2 | 1/2003 |
| WO | WO-2004099127 | A1 | 11/2004 |
| WO | WO-2005012221 | A1 | 2/2005 |
| WO | WO-2005014533 | A2 | 2/2005 |
| WO | WO-2006055625 | A2 | 5/2006 |
| WO | WO-2006093823 | A1 | 9/2006 |
| WO | WO-2009135590 | A1 | 11/2009 |
| WO | WO-2010048149 | A2 | 4/2010 |
| WO | WO-2012016133 | A2 | 2/2012 |
| WO | WO-2021202955 | A1 | 10/2021 |
| WO | WO-2022043755 | A2 | 3/2022 |

OTHER PUBLICATIONS

Caira. Crystalline Polymorphism of Organic Compounds. Topics in Current Chemistry. 198:163-208 (Jan. 1998).

Cole et al., Single-factor scoring validation for the Health Assessment Questionnaire-Disability Index (HAQ-DI) in patients with systemic sclerosis and comparison with early rheumatoid arthritis patients. Qual Life Res. 15(8):1383-94 (2006).

Collard et al. Acute exacerbation of idiopathic pulmonary fibrosis. An international working group report. Am J Respir Crit Care Med. 194(3):265-75 (2016).

Ellery et al. Identification of compounds acting as negative allosteric modulators of the LPA 1 receptor. Eur J Pharmacol 833:8-15 (2018).

Giron. Applications of Thermal Analysis and Coupled Techniques in Pharmaceutical Industry. J Therm Anal Calorim 68:335-357 (2002).

Giron. Investigations of Polymorphism and Pseudo-polymorphism in Pharmaceuticals by Combined Thermoanalytical Techniques. J Therm Anal Calorim 64:37-60 (2001).

González-Gil et al. The status of the lysophosphatidic acid receptor type 1 (LPA 1 R). MedChemComm 6:13-23 (2015).

Graham et al., Executive Summary: 2017 ERS/ATS standards for single-breath carbon monoxide uptake in the lung. Eur Respir J. 49(1):1600016 (2017).

Graham et al., Standardization of Spirometry 2019 Update. An Official American Thoracic Society and European Respiratory Society Technical Statement. Am J Respir Crit Care Med. 200:e70-e88 (2019).

Guillory. Chapter 5: Generation of Polymorphs, Hydrates, Solvates, and Amorphous Solids. Polymorphism in Pharmaceutical Solids pp. 183-226 (Brittain, H.G., ed., 1999).

Harel et al., Measuring fatigue in SSc: a comparison of the Short Form-36 Vitality subscale and Functional Assessment of Chronic Illness Therapy-Fatigue scale. Rheumatology (Oxford) 51:2177-85 (2012).

Holzer et al. K$\alpha$1,2 and K$\beta$1,3 x-ray emission lines of the 3d transition metals. Phys. Rev. A56(6):4554-4568 (1997).

Hutchinson et al., Global incidence and mortality of idiopathic pulmonary fibrosis: a systematic review. Eur Respir J. 46:795-806 (2015).

International Conference on Harmonization of Technical Requirements for Registration of Pharmaceuticals for Human Use (ICH), Impurities: Guidelines for Residual Solvents, Q3C(R3) (40 pgs) (Nov. 2005).

Johnson et al., The Health Assessment Questionnaire Disability Index and Scleroderma Health Assessment Questionnaire in scleroderma trials: an evaluation of their measurement properties. Arthritis Rheum. 53:256-62 (2005).

Khanna et al., Abatacept in early diffuse cutaneous systemic sclerosis: results of a phase 2 investigator-initiated, multicenter, double-blind, randomized, placebo-controlled trial. Arthritis Rheumatol. 72:125-36 (2020).

Khanna et al. Outcome measures in systemic sclerosis: an update on instruments and current research. Curr Rheumatol Rep. 9:151-7 (2007).

Khanna et al., Reliability and validity of UCLA Scleroderma Clinical Trial Consortium Gastrointestinal Tract (UCLA SCTC GIT 2.0) instrument. Arthritis Rheumatol. 61(9):1257-63 (2009).

Khanna et al. The American College of Rheumatology Provisional Composite Response Index for Clinical Trials in Early Diffuse Cutaneous Systemic Sclerosis Arthritis Rheumatol. 68(2):299-311 (2016).

Kihara et al. Lysophospholipid receptors in drug discovery. Exp Cell Res 333(2):171-177 (2015).

Lancaster. Utility of the six-minute walk test in patients with idiopathic pulmonary fibrosis. Multidiscip Respir Med. 13:45 (2018).

Ledein et al. Translational engagement of lysophosphatidic acid receptor 1 in skin fibrosis: from dermal fibroblasts of patients with scleroderma to tight skin 1 mouse. J Pharmacol 177(18):4296-4309 (2020).

Llona-Minguez et al. Lysophosphatidic acid receptor (LPAR) modulators: The current pharmacological toolbox. Prog Lipid Res 58:51-75 (2015).

Luquet et al. Peroxisome proliferator-activated receptor delta controls muscle development and oxydative capability. FASEB J 17(13): 209-226 (2003).

Man et al., Development and validation of a patient-reported outcome instrument for skin involvement in patients with systemic sclerosis. Ann Rheum Dis. 76:1374-80 (2017).

Merkel et al., Current status of outcome measure development for clinical trials in systemic sclerosis. Report from OMERACT 6. J Rheumatol. 30:1630-47 (2003).

Palmer et al., Randomized, double-blind, placebo-controlled, phase 2 trial of BMS-986020, a lysophosphatidic acid receptor antagonist for the treatment of idiopathic pulmonary fibrosis. Chest. 154:1061-9 (2018).

PCT/IB2021/000594 International Search Report and Written Opinion dated Feb. 24, 2022.

PCT/IB2021/000594 Invitation to Pay Additional Fees dated Jan. 3, 2022.

PCT/US2021/025505 International Search Report and Written Opinion dated Jun. 29, 2021.

Raghu et al., An official ATS/ERS/JRS/ALAT statement: idiopathic pulmonary fibrosis: evidence-based guidelines for diagnosis and management. Am J Respir Crit Care Med. 183:788-824 (2011).

Raghu et al. Diagnosis of idiopathic pulmonary fibrosis. An official ATS/ERS/JRS/ALAT clinical practice guideline. Am J Respir Crit Car Med. 198:e44-68 (2018).

Reay. The quality of life in patients with diffuse and limited systemic sclerosis. Thesis. Doctor of Philosophy, the University of Leeds, School of Healthcare and School of Medicine. Published online 2008. https://etheses.whiterose.ac.uk/26111/1/503274.pdf.

Rodriguez-Spong et al. General principles of pharmaceutical solid polymorphism: a supramolecular perspective. Adv Drug Deliv Rev 56:241-274 (2004).

Sierakowska et al., Factors associated with quality of life in systemic sclerosis: a cross-sectional study. Qual Life Res. 28:3347-54 (2019).

Smyth et al., A cross-sectional comparison of three self-reported functional indices in scleroderma. Rheumatology 42(6):732-8 (2003).

Souillac et al. Characterization of Delivery Systems, Differential Scanning Calorimetry. Encyclopedia of Controlled Drug Delivery pp. 212-227 (John Wiley & Sons 1999).

(56) References Cited

OTHER PUBLICATIONS

Spiera et al., Safety and efficacy of lenabasum in a Phase II, randomized, placebo-controlled trial in adults with systemic sclerosis. Arthritis Rheumatol. 72(8):1350-60 (2020).
Steen et al., Assessment of kidney involvement. Clin Exp Rheumatol. 21(3Suppl29):S29-31 (2003).
Strickland et al., Predictors of health-related quality of life and fatigue in systemic sclerosis: evaluation of the EuroQol-5D and FACIT-F assessment tools. Clin Rheumatol. 31:1215-22 (2012).
Sultan et al. The health assessment questionnaire (HAQ) is strongly predictive of good outcome in early diffuse scleroderma: results from an analysis of two randomized controlled trials in early diffuse scleroderma. Rheumatology 43:472-8 (2004).
Swigris et al., The SF-36 and SGRQ: validity and first look at minimum important differences in IPF. Respir Med. 104:296-304 (2010).
Tomioka et al., Health-related quality of life in patients with idiopathic pulmonary fibrosis—cross-sectional and longitudinal study. Intern Med. 46:1533-42 (2007).
Vippagunta et al. Crystalline Solids. Advanced Drug Delivery Reviews 48:3-26 (2001).
Ware et al., A 12-Item Short-Form Health Survey: construction of scales and preliminary tests of reliability and validity. Med Care. 34:220-33 (1996).
Horizon Therapeutics plc Announces First Patient Enrolled in Phase 2b Pivotal Trial Evaluating HZN-825 for the Treatment of Idiopathic Pulmonary Fibrosis (IPF) (Jan. 24, 2022). Retrieved from the Internet: URL:https://ir.horizontherapeutics.com/news-releases/news-release-details/horizon-therapeutics-plc-announces-first-patient-enrolled-1 [retrieved on Jul. 17, 2023].
PCT/IB2023/000142 International Search Report and Written Opinion dated Jul. 27, 2023.
Rogliani et al. Pirfenidone, nintedanib and N-acetylcysteine for the treatment of idiopathic pulmonary fibrosis: A systematic review and meta-analysis. Pulm Pharmacol Ther 40:95-103 (2016).

Intergral    -139.76 mJ
normalsiert    -49.37 Jg^-1
Onset    213.88 °C
Peak    216.29 °C Intergral    -274.78 mJ
normalsiert    -97.06 Jg^-1
Onset    204.82 °C
Peak    205.79 °C Intergral    -50.67 mJ
normalsiert    -17.90 Jg^-1
Onset    198.46 °C
Peak    200.35 °C 20 mW Methode: 25-350°C; 10°C/min
dt 1.00s
25.0-350.0°C 10.00°C/min. N2 50.0 ml/min
Synchronisation eingeschatet Modul: DSC822e/700/109/414935/0025, 11.12.2000 14:29:07

Stufe          -15.4463 %
                -0.7878 mg
Onset          298.89 °C
Peak           287.90 °C 1 mg Methode: 25° 10' 25-350° 10°/min  Al 100ul
dt 1.00s
25.0°C 10.0 min  N2 50.0 ml/min
25.0-350.0°C 10.00°C/min  N2 50.0 ml/min
Synchronisation eingeschatet Modul: TGA/SDTA851e/SF1100/MT5/MT5/042. 02.02.2001 12:48:06

Intergral 39.03 mJ
normalsiert 21.39 Jg^-1
Onset 207.48 °C
Peak 208.70 °C

Intergral -129.19 mJ
normalsiert -77.41 Jg^-1
Onset 204.22 °C
Peak 205.29 °C

Intergral -116.09 mJ
normalsiert -69.56 Jg^-1
Onset 213.57 °C
Peak 215.75 °C 10 mW Methode: 25-350°C; 10°C/min
dt 1.00s
25.0-350.0°C 10.00°C/min. N2 50.0 ml/min
Synchronisation eingeschatet
Modul: DSC822e/700/109/414935/0025, 11.12.2000 14:29:07

Panalytical X-Pert Pro MPD PW3040 Pro
X-ray Tube: Cu(1.54060 Å)  Voltage: 45 kV  Amperage: 40 mA  Scan Range: 1.00-39.99 °θ  Step Size: 0.017 °θ
Collection Time: 722 s  Scan Speed: 3.2°/min  Slit: DS: Fixed slit 1/2°  SS: null  Revolution Time: 1.0 s  Mode: Transmission Panalytical X-Pert Pro MPD PW3040 Pro
X-ray Tube: Cu(1.54060 Å)  Voltage: 45 kV  Amperage: 40 mA  Scan Range: 1.00-39.99 °θ  Step Size: 0.017 °θ
Collection Time: 721 s  Scan Speed: 3.2°/min  Slit: DS: Fixed slit 1/2°  SS: null  Revolution Time: 1.0 s  Mode: Transmission

METHODS OF TREATING SYSTEMIC SCLEROSIS AND IDIOPATHIC PULMONARY FIBROSIS

CROSS-REFERENCE

This application claims the benefit of U.S. Provisional Application No. 63/315,793 filed on Mar. 2, 2022, which is incorporated by reference in its entirety.

FIELD OF THE INVENTION

Described herein are methods of using a lysophosphatidic acid receptor 1 (LPA$_1$ receptor, LPAR1, also known as endothelial differentiation gene 2 or EDG-2) antagonist compound, and crystalline forms thereof, as well as pharmaceutical compositions thereof, in the treatment of diseases or conditions that would benefit with treatment with an LPA$_1$ receptor antagonist compound, such as fibrotic diseases or conditions.

BACKGROUND OF THE INVENTION

The LPA$_1$ receptor (LPAR1) is a member of the G protein-coupled receptor family of integral membrane proteins that are important for lipid signaling. LPA$_1$ receptor antagonists are being investigated for the potential as novel therapeutics of diseases or conditions for which abnormal LPA signaling plays a role, such as systemic sclerosis, pulmonary fibrosis, atherosclerosis, myocardial infarction, and heart failure.

SUMMARY OF THE INVENTION

The present disclosure relates to various methods of treating systemic sclerosis and lung diseases, such as pulmonary fibrosis with the LPA$_1$ receptor antagonist 2-(4-methoxy-3-(3-methylphenethoxy)benzamido)-2,3-dihydro-1H-indene-2-carboxylic acid (Compound I).

In one aspect, described herein is a method of treating systemic sclerosis or lung disease in a subject in need thereof, comprising administering to the subject a therapeutically effective amount of 2-(4-methoxy-3-(3-methylphenethoxy)benzamido)-2,3-dihydro-1H-indene-2-carboxylic acid (Compound I), or a pharmaceutically acceptable salt thereof, wherein Compound I, or a pharmaceutically acceptable salt thereof, is administered at a daily dose equivalent to at least about 300 mg/day of Compound I. In some embodiments, Compound I is Crystalline Form 1 of Compound I, characterized as having an X-ray powder diffraction (XRPD) pattern with peaks at 5.2±0.2° 2-Theta, 9.0±0.2° 2-Theta, 14.4±0.2° 2-Theta, and 17.7±0.2° 2-Theta, as measured using Cu (Kα) radiation. In some embodiments, the crystalline Form 1 of Compound I is substantially free of crystalline Form 2 of Compound I. In some embodiments, the crystalline Form 1 of Compound I comprises less than 1% w/w of crystalline Form 2 of Compound I. In some embodiments, Compound I is the amorphous phase of Compound I, characterized as having: an X-ray powder diffraction (XRPD) pattern showing a lack of crystallinity, and a Solid State $^{13}$Carbon Nuclear Magnetic Resonance (ssNMR) spectrum substantially the same as shown in FIG. 16.

In some embodiments, the systemic sclerosis is chosen from limited cutaneous systemic sclerosis, diffuse cutaneous systemic sclerosis, and systemic sclerosis sine scleroderma. In some embodiments, the systemic sclerosis is diffuse cutaneous systemic sclerosis. In some embodiments, the systemic sclerosis is early diffuse cutaneous systemic sclerosis. In some embodiments, treatment with Compound I, or a pharmaceutically acceptable salt thereof, results in a CRISS score of greater or equal to 0.60. In some embodiments, treatment with Compound I, or a pharmaceutically acceptable salt thereof, results in a reduction in skin fibrosis as measured by mRSS change of ≥5. In some embodiments, treatment with Compound I, or a pharmaceutically acceptable salt thereof, results in an improvement in HAQ-DI of ≥0.14.

In some embodiments, the lung disease is lung fibrosis. In some embodiments, the lung disease is interstitial lung disease (ILD). In some embodiments, the lung disease is idiopathic interstitial pneumonia, connective tissue disease-associated interstitial lung disease (CTD-ILD), sarcoidosis, hypersensitivity pneumonitis, eosinophilic ILD, or familial pulmonary fibrosis. In some embodiments, the lung disease is idiopathic pulmonary fibrosis (IPF), Non-specific interstitial pneumonia (NSIP), Cryptogenic organizing pneumonia (COP), respiratory bronchiolitis interstitial lung disease (RBILD), desquamative interstitial pneumonia (DIP), acute interstitial pneumonia (AIP), or lymphoid interstitial pneumonia (LIP). In some embodiments, the lung disease is autoimmune-ILD (e.g rheumatoid arthritis-ILD, systemic sclerosis-ILD, Sjögren syndrome-ILD, dermatomyositis-ILD, Lupus-ILD, plymyositis-ILD, sarcoidosis-ILD). In some embodiments, the lung disease is unclassifiable-ILD, hypersensitivity pneumonitis-ILD, or drug-induced-ILD. In some embodiments, the lung disease is radiation-induced lung injury (RILI). In some embodiments, the lung disease is idiopathic pulmonary fibrosis (IPF). In some embodiments, the lung disease is chronic fibrosing interstitial lung disease (ILD). In some embodiments, the lung disease is chronic fibrosing interstitial lung diseases (ILDs) with a progressive phenotype. In some embodiments, the lung disease is progressive phenotype is usual interstitial pneumonia (UIP) or UIP-like high resolution computed tomography (HRCT) fibrotic pattern. In some embodiments, the lung disease is systemic sclerosis-associated interstitial lung disease (SSc-ILD). In some embodiments, the lung disease is systemic sclerosis-associated interstitial lung disease (SSc-ILD), and wherein treating the lung disease comprises slowing the rate of decline in pulmonary function in the subject with SSc-ILD.

In some embodiments, treating lung disease comprises slowing the decline in lung function, reducing the frequency of exacerbations of the lung disease, reducing hospitialization rates for patients with lung disease, improving survival of the patient with lung disease, or combinations thereof.

In some embodiments, Compound I, or a pharmaceutically acceptable salt thereof, is administered for a period of at least about 24 consecutive weeks. In some embodiments, Compound I, or a pharmaceutically acceptable salt thereof, is administered for a period of at least about 36 weeks. In some embodiments, Compound I, or a pharmaceutically acceptable salt thereof, is administered for a period of at least about 52 weeks.

In some embodiments, Compound 1, or a pharmaceutically acceptable salt thereof, is administered orally. In some embodiments, Compound I, or a pharmaceutically acceptable salt thereof, is administered at a dose equivalent to about 300 mg of Compound I once daily. In some embodiments, Compound I, or a pharmaceutically acceptable salt thereof, is administered at a dose equivalent to about 300 mg of Compound I twice daily for a total daily dose equivalent to about 600 mg/day of Compound I.

In some embodiments, Compound I, or a pharmaceutically acceptable salt thereof, is administered in combination with a cough suppression medication, a corticosteroid, an immunosuppressant, N-acetyl cysteine (NAC), an anti-fibrotic therapeutic agent, or combinations thereof. In some embodiments, Compound I, or a pharmaceutically acceptable salt thereof, is administered in combination with N-acetyl cysteine, a corticosteroid, an immunosuppressant, pirfenidone, nintedanib, imatinib, a tyrosine kinase inhibitor, PBI-4050, recombinant pentraxin-2/SAP (PRM-151), aerosol IFN-$\gamma$, an inhibitor of CTGF activity, a LPA receptor antagonist, an autotaxin inhibitor, a galectin-3 inhibitor, a LOXL2 inhibitor, tipelukast, an integrin antagonist, a PI3K inhibitor, a JNK inhibitor, a ROCK inhibitor, an anti-IL-13 compound, a CCL2 antagonist, a CCR2 antagonist, an anti-CD20 compound, an anticoagulant, a collagen V treatment, an ASK1 inhibitor, belimumamb, a B-cell activating factor inhibitior, belumosudil, a Rho-associated coiled-cil kinase 2 (Rock2) inhibitor, a NO-independent soluble guanylate cyclase (sGC) activator, a transforming growth factor beta 1 antagonist, a PDE-4b inhibitor, or combinations thereof.

In some embodiments, Compound I, or a pharmaceutically acceptable salt thereof, is administered in combination with nintedanib, or a pharmaceutically acceptable salt thereof. In some embodiments, nintedanib, or a pharmaceutically acceptable salt thereof, is admininsted at a daily dose equivalent to about 200 mg/day or about 300 mg/day of nintedanib. In some embodiments, nintedanib, or a pharmaceutically acceptable salt thereof, is orally admininsted at a dose equivalent to about 150 mg twice daily, wherein each dose is administered approximately 12 hours apart. In some embodiments, nintedanib, or a pharmaceutically acceptable salt thereof, is orally admininsted at a dose equivalent to about 100 mg twice daily, wherein each daily dose is administered approximately 12 hours apart.

In some embodiments, Compound I, or a pharmaceutically acceptable salt thereof, is administered in combination with pirfenidone. In some embodiments, pirfenidone is administered at a dose of about 801 mg/day to about 2403 mg/day. In some embodiments, pirfenidone is administered at a dose of about 267 mg three times a day. In some embodiments, pirfenidone is administered at a dose of about 534 mg three times a day.

In some embodiments, pirfenidone is administered at a dose of about 801 mg three times a day.

In some embodiments, Compound I, or a pharmaceutically acceptable salt thereof, is administered in the form of a solid form pharmaceutical composition. In some embodiments, the solid form pharmaceutical composition is a tablet, a pill, or a capsule. In some embodiments, the solid form pharmaceutical composition is a tablet.

In some embodiments, Compound I, or a pharmaceutically acceptable salt thereof, is administered in the form of one or more tablets. In some embodiments, each tablet and comprises about 50 mg to about 300 mg of Compound I. In some embodiments, each tablet and comprises about 50 mg to about 150 mg of Compound I.

In some embodiments, the subject is an adult human. In some embodiments, the subject is an adult male human.

Also described herein, in some embodiments, is a pharmaceutical composition comprising a crystalline form Compound I and at least one pharmaceutically acceptable excipient. For example, in some embodiments, described herein is a pharmaceutical composition comprising Crystalline Form 1 and at least one pharmaceutically acceptable excipient. In some embodiments, the pharmaceutical composition is formulated for administration to a mammal by oral administration. In some embodiments, the pharmaceutical composition is formulated for administration to a mammal by oral administration in the form of a tablet, a pill, a capsule, a suspension, or a solution. In some embodiments, the pharmaceutical composition is in the form of a solid form pharmaceutical composition. In some embodiments, the pharmaceutical composition is in the form of a tablet, a pill, or a capsule. In some embodiments, the pharmaceutical composition is substantially free of Compound I impurities. In some embodiments, the pharmaceutical composition comprises less than about 1% w/w of Compound I impurities. In some embodiments, the Compound I impurities comprise one or more degradants of Compound I, one or more intermediates used in the synthesis of Compound I, or combinations thereof. In some embodiments, the Compound I impurities comprise one or more intermediates used in the synthesis of Compound I.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Figure 1:
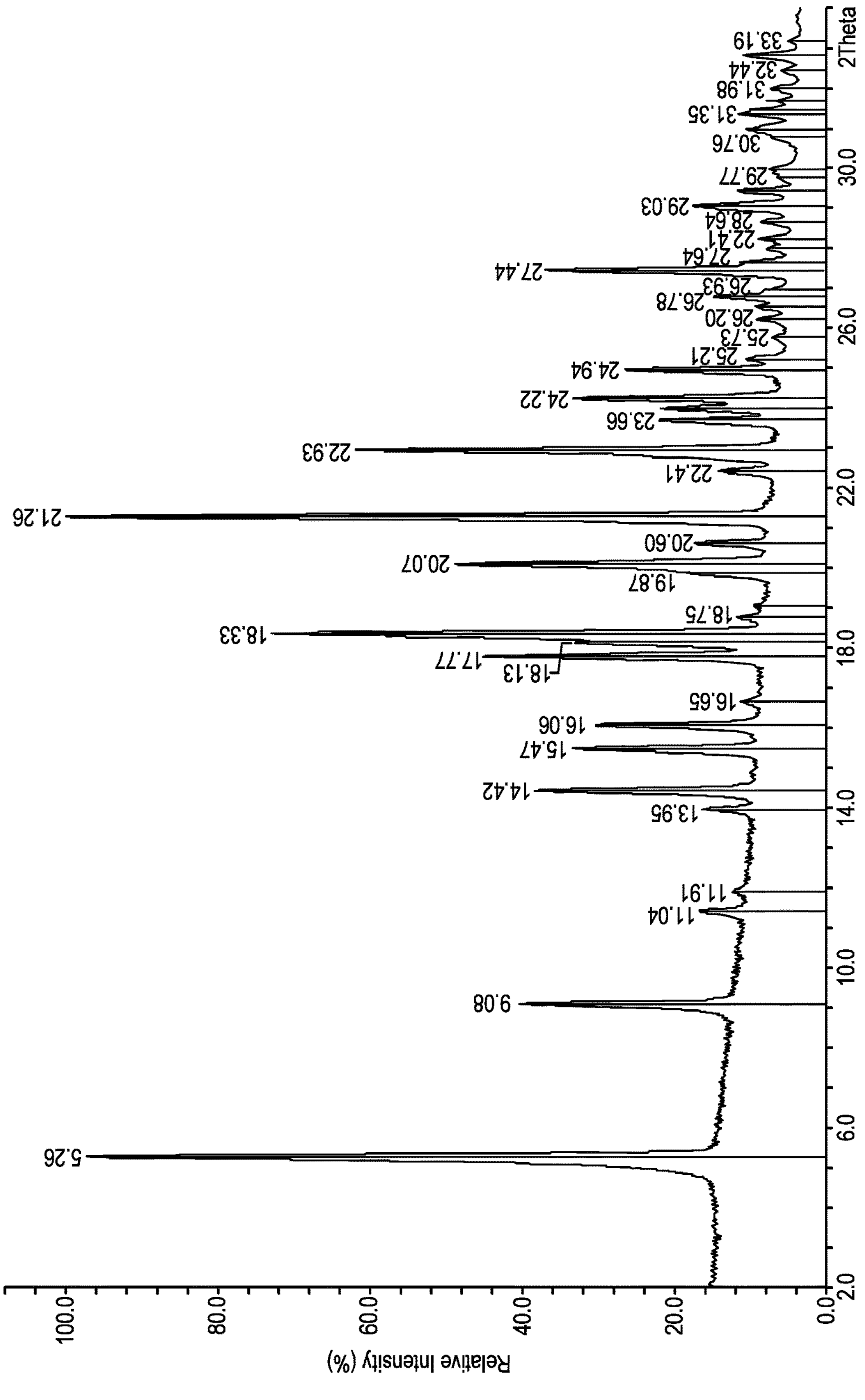
FIG. 1 shows the X-ray powder diffraction (XRPD) pattern of Form 1.

Compound I refers to "2-(4-methoxy-3-(3-methylphenethoxy)benzamido)-2,3-dihydro-1H-indene-2-carboxylic acid" or "2-[4-methoxy-3-(2-m-tolyl-ethoxy)-benzoylamino]-indane-2-carboxylic acid", which has the chemical structure shown below:

Compound I

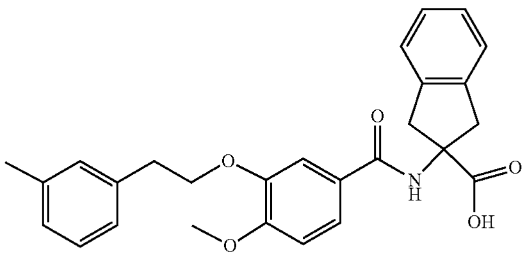

See, U.S. Pat. Nos. 9,328,071 and 8,362,073, each of which is hereby incorporated by reference in its entirety. Compound 1 also may be referred to as CZN001, SAR100842, or HZN-825.

Compound I is a potent and selective antagonist of lysophosphatidic acid receptor 1 (LPAR1). LPAR1 signaling has been implicated in fibrosis and inflammation. Specifically, animal models of fibrosis demonstrate that LPAR1 is involved in fibrosis of skin, lung, kidney, and heart. LPAR1 deletion in mice was found to be protective against dermal and lung fibrosis. LPAR1 antagonism reduced immune cell infiltration into lungs in an experimental model of lung irritation. Serum lysophosphatidic acid (LPA) levels are elevated in patients with systemic sclerosis. Fibroblasts from patients show elevated LPAR1 levels and increased sensitivity to LPAR1 antagonism versus normal fibroblasts.

In vivo, Compound I reversed dermal thickening and significantly inhibited myofibroblast differentiation and reduced collagen content in a mouse model of skin fibrosis. Mechanistic investigations showed that the antifibrotic effects of $LPA_1$ blockade could be mediated partly via inhibition of the Wnt signaling pathway. In the clinical setting, Compound I was well tolerated in patients with diffuse cutaneous systemic sclerosis SSc (dcSSc), demonstrated target engagement, and improved outcome measures (Y. Allanore et al. *Arthritis & Rheumatology*, Vol. 70, No. 10, October 2018, pp 1634-1643).

Scleroderma

Scleroderma or systemic sclerosis is a potentially fatal autoimmune disease of unknown etiology, characterized by progressive multi-organ fibrosis that is largely refractory to currently available pharmacological therapies. Systemic sclerosis is thought to be initiated by tissue injury, in response to which dysregulated wound-healing processes are thought to contribute to the development of fibrosis.

In some embodiments, disclosed herein is the use of Compound I, or a pharmaceutically acceptable salt thereof, in the treatment of scleroderma. There are two major forms of scleroderma: limited systemic sclerosis (also known as morphea or cutaneous scleroderma) and diffuse systemic sclerosis. In some embodiments, Compound I, or a pharmaceutically acceptable salt thereof, is used to treat limited systemic sclerosis. In some embodiments, Compound I, or a pharmaceutically acceptable salt thereof, is used to treat diffuse systemic sclerosis.

As used herein, "limited systemic scleroderma" means a disorder characterized by the thickening and hardening of the skin and subcutaneous tissues from excessive collagen deposition. It is often accompanied by the following: calcinosis, Raynaud's phenomenon, esophageal dysfunction, sclerodactyly, and telangiectasias. Additionally, an individual suffering from limited systemic sclerosis may present with pulmonary arterial hypertension.

As used herein, "diffuse systemic scleroderma" means a disorder of the skin and internal organs characterized by the thickening and hardening of the skin and subcutaneous tissues from excessive collagen deposition. In certain instances, diffuse systemic scleroderma is accompanied by Raynaud's phenomenon and calcinosis.

In some embodiments, Compound I, or a pharmaceutically acceptable salt thereof, is used in the treatment or prevention of any one of the following in a mammal: localized cutaneous scleroderma, localized morphea, morphea-lichen sclerosus et atrophicus overlap, generalized morphea, atrophoderma of Pasini and Pierini, pansclerotic morphea, morphea profunda, linear scleroderma, systemic scleroderma, CREST syndrome, sclerodactyly, systemic sclerosis, progressive systemic sclerosis.

Systemic sclerosis sine scleroderma is a rare disorder in which patients develop vascular and fibrotic damage to internal organs in the absence of cutaneous sclerosis.

In a Phase 2a trial that evaluated 32 subjects with diffuse cutaneous SSc, administration of Compound I at a dose of about 300 mg BID resulted in numerical improvement on clinical outcomes, including the modified Rodnan skin score (mRSS), Health Assessment Questionnaire—Disability Index (HAQ-DI) and other components of Scleroderma Health Assessment Questionnaire (SHAD), overall disease severity (visual analog scale [VAS]) and pruritus (VAS) (Y. Allanore et al. *Arthritis & Rheumatology*, Vol. 70, No. 10, October 2018, pp 1634-1643). In this trial, Compound I at a dose of about 300 mg BID was administered up to 24 weeks and was well tolerated. During the 8-week double-blind period, the most frequent treatment-emergent adverse events (TEAEs) in the Compound I group were headache, diarrhea, nausea and fall.

Lung Fibrosis

In a Phase 2 clinical trial of IPF, LPAR1 antagonism significantly slowed the rate of decline in forced vital capacity (FVC) compared with placebo [Palmer et al., Randomized, double-blind, placebo-controlled, phase 2 trial of BMS-986020, a lysophosphatidic acid receptor antagonist for the treatment of idiopathic pulmonary fibrosis. *Chest.* 2018; 154:1061-9]. These findings suggest a role for antagonists of LPAR1 as therapeutic treatments for a variety of fibrotic conditions.

Idiopathic pulmonary fibrosis (IPF) is a specific form of chronic, progressive, fibrosing interstitial pneumonia of unknown cause that is limited to the lungs. Well over one hundred different forms of interstitial lung disease (ILD) have been described. These diffuse infiltrative lung disorders are typically characterized by the presence of inflammation and altered lung interstitium. The histopathologic changes in the lungs of patients with ILD can range from granulomatous inflammation without parenchymal fibrosis in patients with sarcoidosis to extensive pulmonary fibrosis with architectural distortion of the lung in patients with idiopathic pulmonary fibrosis (IPF). Some forms of ILD have been linked to specific genetic abnormalities (e.g. Hermansky-Pudlak syndrome, familial pulmonary fibrosis), and a number of gene variants have been associated with an increased risk to develop ILD disorders such as IPF, sarcoidosis, or chronic beryllium disease (CBD).

Interstitial lung disease can also complicate connective tissue disorders (CTD), and lung histopathologic changes can have features of usual interstitial pneumonia (UIP) or non-specific interstitial pneumonia (NSIP) patterns in CTD-associated ILD.

In some embodiments, interstitial lung disease (ILD) includes, but is not limited to, idiopathic interstitial pneumonia, scleroderma-associated ILD, connective tissue disease-associated interstitial lung disease (CTD-ILD), sarcoidosis, hypersensitivity pneumonitis, iatrogenic pneumonitis/fibrosis (drug-induced ILD, radiation injury), eosinophilic ILD (e.g. eosinophilic pneumonia), occupational lung disease, inherited disorders (e.g. familial pulmonary fibrosis, Hermansky-Pudlak syndrome), and primary disorders (e.g. pulmonary Langerhans cell histiocytosis). In some embodiments, idiopathic interstitial pneumonia includes, but is not limited to, idiopathic pulmonary fibrosis (IPF), non-specific interstitial pneumonia (NSIP), Cryptogenic organizing pneumonia (COP), respiratory bronchiolitis interstitial lung disease (RBILD), desquamative interstitial pneumonia (DIP), acute interstitial pneumonia (AIP), lymphoid interstitial pneumonia (LIP).

In some embodiments, the lung fibrosis is idiopathic interstitial pneumonia, CTD-ILD, sarcoidosis, hypersensitivity pneumonitis, eosinophilic ILD, or familial pulmonary fibrosis. In some embodiments, the lung fibrosis is IPF, NSIP, COP, RBILD, DIP, AIP, or LIP. In some embodiments, the lung fibrosis is autoimmune-ILD (e.g rheumatoid arthritis-ILD, systemic sclerosis-ILD, Sjögren syndrome-ILD, dermatomyositis-ILD, Lupus-ILD, plymyositis-ILD, sarcoidosis-ILD). In some embodiments, the lung fibrosis is unclassifiable-ILD, hypersensitivity pneumonitis-ILD, or drug-induced-ILD. In some embodiments, the lung fibrosis is radiation-induced lung injury (RILI). In some embodiments, the lung fibrosis is idiopathic pulmonary fibrosis (IPF). In some embodiments, the lung fibrosis is chronic fibrosing interstitial lung disease (ILD). In some embodiments, the lung fibrosis is chronic fibrosing interstitial lung diseases (ILDs) with a progressive phenotype. In some embodiments, the lung fibrosis is progressive phenotype is usual interstitial pneumonia (UIP) or UIP-like high resolution computed tomography (HRCT) fibrotic pattern. In some embodiments, the lung fibrosis is systemic sclerosis-associated interstitial lung disease (SSc-ILD). In some embodiments, the lung fibrosis is SSc-ILD, and wherein treating the lung fibrosis comprises slowing the rate of decline in pulmonary function in the subject with SSc-ILD.

IPF is a progressive and ultimately fatal disease of the lungs involving airway epithelial cell damage, fibroblast activation and proliferation, and excessive deposition of collagen and other extracellular matrix (ECM) components. These modifications of ECM composition and organisation alter the biomechanical properties of the lung parenchyma and increase local tension, which is critical in IPE disease pathogenesis.

IPF is a specific form of chronic, progressive, fibrosing interstitial pneumonia of unknown cause, that is limited to the lungs, and associated with the histopathologic and/or radiologic pattern of UIP or UIP-like. It is a disease characterized clinically by progressive worsening of dyspnea and lung function and pathologically by the formation of scar tissue within the lungs in the absence of any known provocation.

In 2018, the American Thoracic Society (ATS), European Respiratory Society (ERS), Japanese Respiratory Society (JRS) and the Latin American Thoracic Society (ALAT) jointly updated recommendations to reach a consensus for the diagnosis of IPF [Raghu et al., *Am J Respir Crit Car Med.* 2018; 198:e44-68]. IPF is the most common type of ILD, estimated to affect 132,000 to 200,000 people in the US. In the US, approximately 50,000 new cases are diagnosed each year, and as many as 40,000 patients die from IPF each year according to the Pulmonary Fibrosis Foundation. IPF is diagnosed more frequently in men than women, patients usually present with symptoms of IPF between the ages of 40 and 70 years with the median age for presentation being 66 years. IPF is characterized by progressive dyspnea, non-productive cough and progressive pulmonary insufficiency consistent with increasing fibrosis.

Evidence suggests that the incidence of IPF is rising [Hutchinson et al., *Eur Respir J.* 2015; 46:795-806]. Mortality following diagnosis of IPF is high, with a median survival of 2 to 3 years from time of diagnosis [Raghu et al., *Am J Respir Crit Care Med.* 2011; 1 83:788-824].

IPF is characterized by decline in lung function over time. The most prominent symptoms of IPF are exercise-induced dyspnea and chronic dry cough, which interfere with daily activities of the patients. Aside from restrictive defects on pulmonary function, other frequent clinical features of IPF include bibasilar inspiratory crackles and hypoxemia induced clubbing. Retrospective studies suggest that symptoms precede the IPF diagnosis by a duration of 6 months to 2 years. The onset of symptoms is slow, but over a period of months to years, symptoms worsen and lung function slowly declines, leading to hypoxia and eventually death from respiratory failure. There are 3 potential clinical courses for IPF: a) slow physiologic deterioration with worsening severity of dyspnea, which is the most common; b) rapid deterioration and progression to death; or c) periods of relative stability interposed with periods of acute respiratory decline sometimes manifested by hospitalizations for respiratory failure.

Although IPF is considered a disorder of unknown etiology by definition, a number of potential risk factors have been identified. Cigarette smoking is strongly associated with IPF. In addition, various other environmental and occupational exposures to metal dusts, wood dust, farming, hairdressing, stone cutting/polishing, livestock, and vegetable dust/animal dust have been linked with increased risk for developing IPF.

The pathogenesis of most lung fibroses, including the aforementioned diseases, are not well understood, however all are characterized by an influx of inflammatory cells and a subsequent increase in the synthesis and deposition of collagen-rich extracellular matrix.

IPF is characterized by inflammation, and eventually fibrosis, of lung tissue; although these two symptoms can also be dissociated. The cause of IPF is unknown; it may arise either from an autoimmune disorder or as a result of infection. Symptoms of IPF include dyspnea (i.e., shortness of breath) which becomes the major symptom as the disease progresses, and dry cough. Death can result from hypoxemia, right-heart failure, heart attack, lung embolism, stroke or lung infection, all of which can be brought on by the disease.

In some embodiments, Compound I, or a pharmaceutically acceptable salt thereof, is used in the treatment of a fibrotic condition of the lung. In some embodiments, the fibrotic condition of the lung is chosen from one or more of: pulmonary fibrosis, idiopathic pulmonary fibrosis (IPF), usual interstitial pneumonitis (UIP), interstitial lung disease, cryptogenic fibrosing alveolitis (CFA), acute respiratory distress syndrome (ARDS), diffuse parenchymal lung disease (DPLD), bronchiolitis obliterans, or bronchiectasis. In some embodiments, the fibrosis of the lung is secondary to a disease, a toxin, an insult, a medical treatment, or a combination thereof. In some embodiments, fibrosis of the lung is associated with one or more of: a disease process such as asbestosis and silicosis; an occupational hazard; an environmental pollutant; cigarette smoking; an autoimmune connective tissue disorders (e.g., rheumatoid arthritis, scleroderma and systemic lupus erythematosus (SLE)); a connective tissue disorder such as sarcoidosis; an infectious disease, e.g., infection, particularly chronic infection; a medical treatment, including but not limited to, radiation therapy, and drug therapy, e.g., chemotherapy (e.g., treatment with as bleomycin, methotrexate, amiodarone, busulfan, and/or nitrofurantoin). In some embodiments, the fibrotic condition of the lung treated with the methods of the invention is associated with (e.g., secondary to) a cancer treatment, e.g., treatment of a cancer (e.g. squamous cell carcinoma, testicular cancer, Hodgkin's disease with bleomycin).

In some embodiments, Compound I, or a pharmaceutically acceptable salt thereof, is administered to an adult human with lung fibrosis. In some embodiments, the lung fibrosis is IPF. In some embodiments, the adult human is >18 years of age, >20 years of age, >25 years of age, >30 years of age, >35 years of age, >40 years of age, >45 years of age, >50 years of age, >55 years of age, >60 years of age, >65 years of age, >70 years of age, >75 years of age, >80 years of age, or >85 years of age. In some embodiments, the adult human is 30 to 85 years of age, 35 to 85 years of age, 40 to 85 years of age, 45 to 85 years of age, or 40 to 80 years of age.

Idiopathic pulmonary fibrosis affects more adult men than women. In some embodiments, Compound I, or a pharmaceutically acceptable salt thereof, is administered to an adult male human with lung fibrosis.

Compound I

The preparation and uses of Compound I have been previously described (see, WO 2009/135590, U.S. Pat. Nos. 8,362,073, 8,445,530, 8,802,720, 9,328,071, each of which is incorporated by reference in its entirety).

In some embodiments provided herein, Compound I is crystalline.

In some embodiments provided herein, Compound I is a single crystalline form. In some embodiments provided herein, Compound I is a single crystalline form that is substantially free of any other crystalline form. In some embodiments, the crystalline solid form is a single solid state form, e.g. crystalline Form 1. In some embodiments, "substantially free" means less than about 10% w/w, less than about 9% w/w, less than about 8% w/w, less than about 7% w/w, less than about 6% w/w, less than about 5% w/w, less than about 4% w/w, less than about 3% w/w, less than about 2.5% w/w, less than about 2% w/w, less than about 1.5% w/w, less than about 1% w/w, less than about 0.75% w/w, less than about 0.50% w/w, less than about 0.25% w/w, less than about 0.10% w/w, or less than about 0.05 w/w of any other crystalline form (e.g., Form 2) in a sample of crystalline Form 1. In some embodiments, "substantially free" means an undetectable amount (e.g., by XRPD analysis).

In some embodiments, crystallinity of a solid form is determined by X-Ray Powder Diffraction (XRPD). In some embodiments, crystallinity of a solid form is determined by solid state NMR. In some embodiments, crystallinity of a solid form is determined by Fourier Transform IR Spectroscopy (FTIR).

Crystalline Form 1 of Compound I

Figure 4:
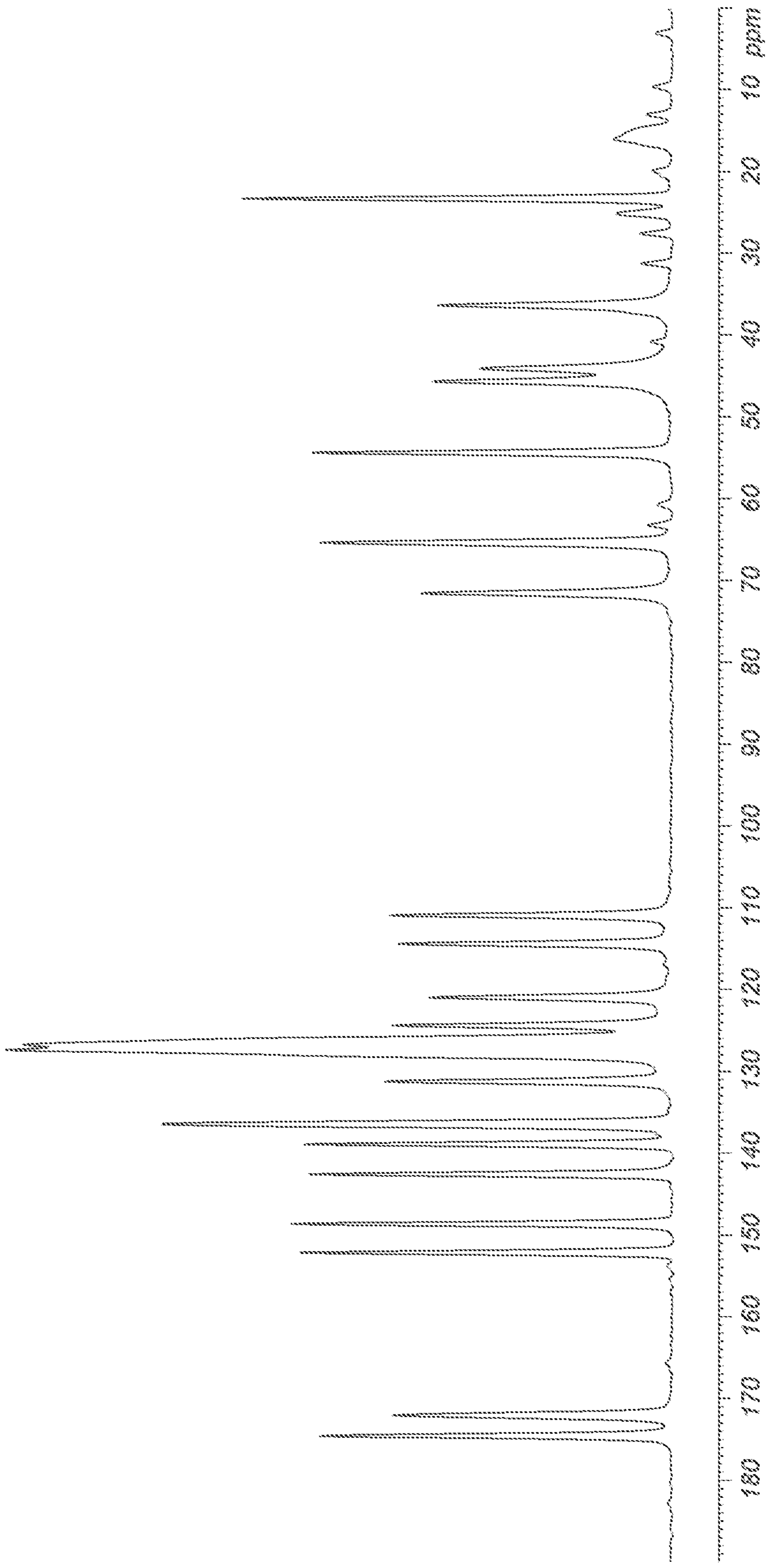
FIG. 4 shows the Solid State $^{13}$Carbon NMR Spectrum of Form 1.

In one aspect, provided herein is crystalline Form 1 of Compound I. Some embodiments provide a composition comprising crystalline Form 1 of Compound I. In some embodiments, crystalline Form 1 of Compound I is characterized as having:

an X-ray powder diffraction (XRPD) pattern substantially the same as shown in FIG. 1, as measured using Cu (Kα) radiation;

an X-ray powder diffraction (XRPD) pattern derived using Cu (Kα) radiation with peaks at 5.2±0.2° 2-Theta, 9.0±0.2° 2-Theta, 14.4±0.2° 2-Theta, and 17.7±0.2° 2-Theta, as measured using Cu (Kα) radiation;

a Fourier Transform IR Spectroscopy (FTIR) pattern with a peak at about 1739.6 $cm^{-1}$;

unit cell parameters substantially equal to the following at 293 K:

| | |
|---|---|
| Crystal System | triclinic |
| Space Group | P-1; Z = 2 |
| a (Å) | 6.521(6) |
| b (Å) | 10.548(9) |
| c (Å) | 17.453(15) |
| α (°) | 104.080(16) |
| β (°) | 92.430(16) |
| γ (°) | 101.081(17) |
| V ($Å^3$) | 1137.6(17) |
| Calculated Density ($Mg/m^3$) | 1.301 |
| Unique Reflections | 4753 |

a Solid State $^{13}$Carbon Nuclear Magnetic Resonance (ssNMR) spectrum substantially the same as shown in FIG. 4;

a Solid State $^{13}$Carbon Nuclear Magnetic Resonance (ssNMR) spectrum characterized by resonances (δc) at 23.35, 124.43, 126.78, 127.42, and 136.47 ppm; or combinations thereof.

In some embodiments, crystalline Form 1 of Compound I has an X-ray powder diffraction (XRPD) pattern with peaks at 5.2±0.2° 2-Theta, 9.0±0.2° 2-Theta, 14.4±0.2° 2-Theta, and 17.7±0.2° 2-Theta, as measured using Cu (Kα) radiation.

In some embodiments, crystalline Form 1 of Compound I has an X-ray powder diffraction (XRPD) pattern with peaks at 5.2±0.2° 2-Theta, 9.0±0.2° 2-Theta, 14.4±0.2° 2-Theta, and 17.7±0.2° 2-Theta, as measured using Cu (Kα)

radiation; and a Fourier Transform IR Spectroscopy (FTIR) pattern with a peak at about 1739.6 $cm^{-1}$.

In some embodiments, crystalline Form 1 of Compound I has an X-ray powder diffraction (XRPD) pattern with peaks at 5.2±0.2° 2-Theta, 9.0±0.2° 2-Theta, 14.4±0.2° 2-Theta, and 17.7±0.2° 2-Theta, as measured using Cu (Kα) radiation; and a Differential Scanning calorimetry (DSC) thermogram with three endothermic events having: an onset at about 198.5° C. and a peak at about 200.4° C.; an onset at about 204.8° C. and a peak at about 205.8° C.; and an onset at about 213.9° C. and a peak at about 216.3° C.

In some embodiments, crystalline Form 1 of Compound I has an X-ray powder diffraction (XRPD) pattern with peaks at 5.2±0.2° 2-Theta, 9.0±0.2° 2-Theta, 14.4±0.2° 2-Theta, and 17.7±0.2° 2-Theta, as measured using Cu (Kα) radiation; and a Solid State $^{13}$Carbon Nuclear Magnetic Resonance (ssNMR) spectrum characterized by resonances (δc) at about 23.35 ppm, about 124.43 ppm, about 126.78 ppm, about 127.42 ppm, and about 136.47 ppm.

In some embodiments, crystalline Form 1 of Compound I has an X-ray powder diffraction (XRPD) pattern with peaks at 5.2±0.2° 2-Theta, 9.0±0.2° 2-Theta, 14.4±0.2° 2-Theta, and 17.7±0.2° 2-Theta, as measured using Cu (Kα) radiation; and a Solid State $^{13}$Carbon Nuclear Magnetic Resonance (ssNMR) spectrum characterized by resonances (δc) at about 23.35 ppm, about 124.43 ppm, about 126.78 ppm, about 127.42 ppm, and about 136.47 ppm; and a Differential Scanning calorimetry (DSC) thermogram with three endothermic events having: an onset at about 198.5° C. and a peak at about 200.4° C.; an onset at about 204.8° C. and a peak at about 205.8° C.; and an onset at about 213.9° C. and a peak at about 216.3° C.

In some embodiments, crystalline Form 1 of Compound I has an X-ray powder diffraction (XRPD) pattern substantially the same as shown in FIG. 1, as measured using Cu (Kα) radiation.

Figure 2:
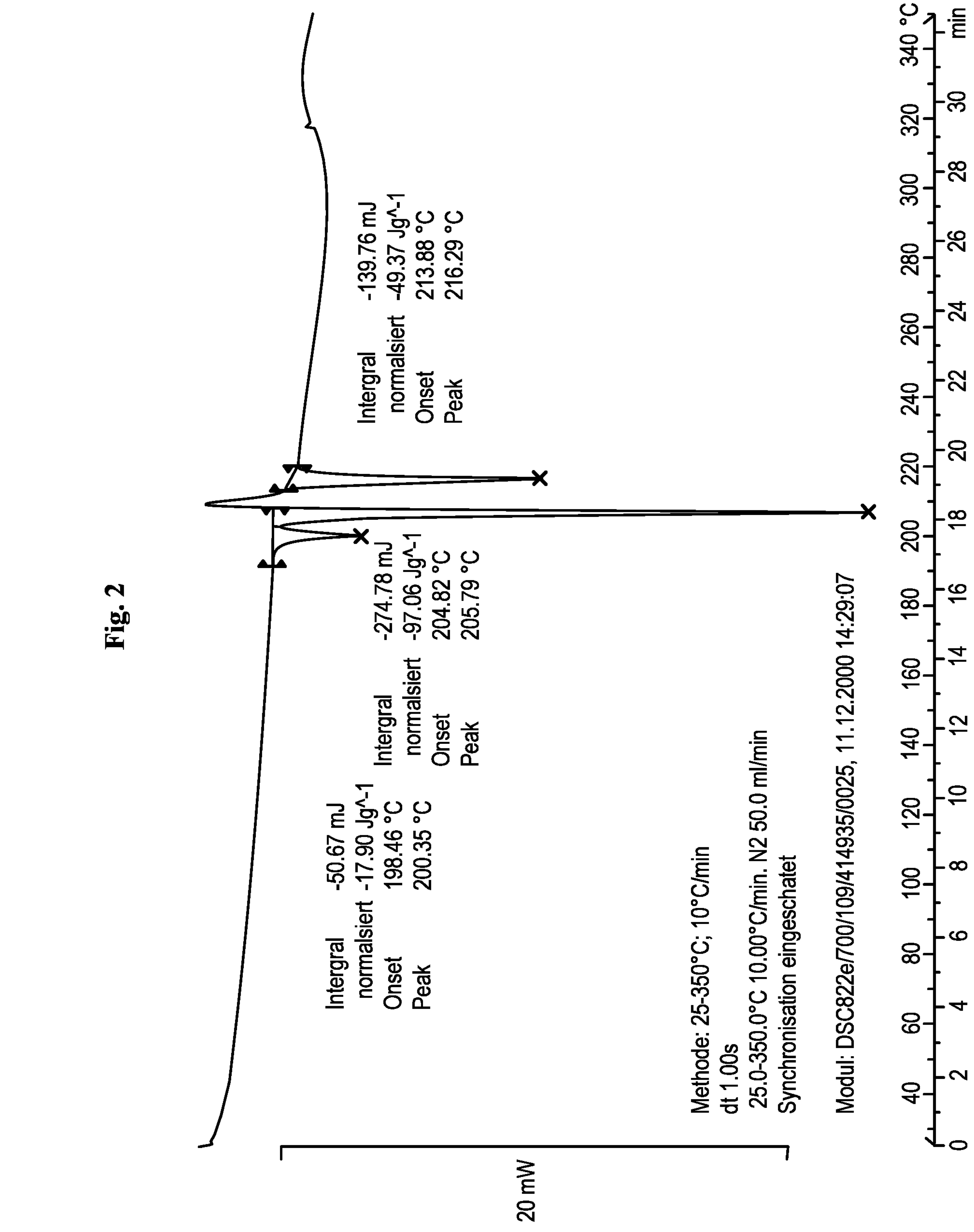
FIG. 2 shows the Differential Scanning calorimetry (DSC) thermogram of Form 1.

In some embodiments, crystalline Form 1 of Compound I has an X-ray powder diffraction (XRPD) pattern substantially the same as shown in FIG. 1, as measured using Cu (Kα) radiation; and a Differential Scanning calorimetry (DSC) thermogram substantially the same as shown in FIG. 2.

In some embodiments, crystalline Form 1 of Compound I has an X-ray powder diffraction (XRPD) pattern substantially the same as shown in FIG. 1, as measured using Cu (Kα) radiation; and a Fourier Transform IR Spectroscopy (FTIR) pattern with a peak at about 1739.6 $cm^{-1}$. In some embodiments, crystalline Form 1 of Compound I has an X-ray powder diffraction (XRPD) pattern substantially the same as shown in FIG. 1, as measured using Cu (Kα) radiation; and a Fourier Transform IR Spectroscopy (FTIR) pattern with a peak at about 1739.6 $cm^{-1}$; and a Differential Scanning calorimetry (DSC) thermogram substantially the same as shown in FIG. 2.

In some embodiments, crystalline Form 1 of Compound I has an X-ray powder diffraction (XRPD) pattern substantially the same as shown in FIG. 1, as measured using Cu (Kα) radiation; and a Solid State $^{13}$Carbon Nuclear Magnetic Resonance (ssNMR) spectrum substantially the same as shown in FIG. 4. In some embodiments, crystalline Form 1 of Compound I has an X-ray powder diffraction (XRPD) pattern substantially the same as shown in FIG. 1, as measured using Cu (Kα) radiation; and a Solid State $^{13}$Carbon Nuclear Magnetic Resonance (ssNMR) spectrum substantially the same as shown in FIG. 4; and a Differential Scanning calorimetry (DSC) thermogram substantially the same as shown in FIG. 2.

In some embodiments, crystalline Form 1 of Compound I is characterized as having a Solid State $^{13}$Carbon Nuclear Magnetic Resonance (ssNMR) spectrum substantially the same as shown in FIG. 4. In some embodiments, crystalline Form 1 of Compound I is characterized as having a Solid State $^{13}$Carbon Nuclear Magnetic Resonance (ssNMR) spectrum substantially the same as shown in FIG. 4; and a Fourier Transform IR Spectroscopy (FTIR) pattern with a peak at about 1739.6 $cm^{-1}$. In some embodiments, crystalline Form 1 of Compound I is characterized as having a Solid State $^{13}$Carbon Nuclear Magnetic Resonance (ssNMR) spectrum substantially the same as shown in FIG. 4; and a Differential Scanning calorimetry (DSC) thermogram substantially the same as shown in FIG. 2.

In some embodiments, crystalline Form 1 of Compound I is characterized as having a Solid State $^{13}$Carbon Nuclear Magnetic Resonance (ssNMR) spectrum characterized by resonances (δc) at about 23.35 ppm, about 124.43 ppm, about 126.78 ppm, about 127.42 ppm, and about 136.47 ppm.

In some embodiments, crystalline Form 1 of Compound I is characterized as having a Solid State $^{13}$Carbon Nuclear Magnetic Resonance (ssNMR) spectrum characterized by resonances (δc) at about 23.35 ppm, about 124.43 ppm, about 126.78 ppm, about 127.42 ppm, and about 136.47 ppm; and a Differential Scanning calorimetry (DSC) thermogram substantially the same as shown in FIG. 2.

In some embodiments, crystalline Form 1 of Compound I is characterized as having a Solid State $^{13}$Carbon Nuclear Magnetic Resonance (ssNMR) spectrum characterized by resonances (δc) at about 23.35 ppm, about 124.43 ppm, about 126.78 ppm, about 127.42 ppm, and about 136.47 ppm; and a Fourier Transform IR Spectroscopy (FTIR) pattern with a peak at about 1739.6 $cm^{-1}$.

In some embodiments, crystalline Form 1 of Compound I is characterized as having a Fourier Transform IR Spectroscopy (FTIR) pattern with a peak at about 1739.6 $cm^{-1}$. In some embodiments, crystalline Form 1 of Compound I is characterized as having a Fourier Transform IR Spectroscopy (FTIR) pattern with a peak at about 1739.6 $cm^{-1}$; and a Differential Scanning Calorimetry (DSC) thermogram substantially the same as shown in FIG. 2.

In some embodiments, crystalline Form 1 of Compound I is characterized as having a Fourier Transform IR Spectroscopy (FTIR) pattern with a peak at about 1739.6 $cm^{-1}$; and a Differential Scanning calorimetry (DSC) thermogram with three endothermic events having: an onset at about 198.5° C. and a peak at about 200.4° C.; an onset at about 204.8° C. and a peak at about 205.8° C.; and an onset at about 213.9° C. and a peak at about 216.3° C.

In some embodiments, crystalline Form 1 of Compound I has a DSC thermogram substantially the same as shown in FIG. 2. In some embodiments, crystalline Form 1 has a DSC thermogram with one or more endothermic events having: an onset at about 198.5° C. and a peak at about 200.4° C.; an onset at about 204.8° C. and a peak at about 205.8° C.; and/or an onset at about 213.9° C. and a peak at about 216.3° C. In some embodiments, crystalline Form 1 has a DSC thermogram with three endothermic events having: an onset at about 198.5° C. and a peak at about 200.4° C.; an onset at about 204.8° C. and a peak at about 205.8° C.; and an onset at about 213.9° C. and a peak at about 216.3° C.

Figure 3:
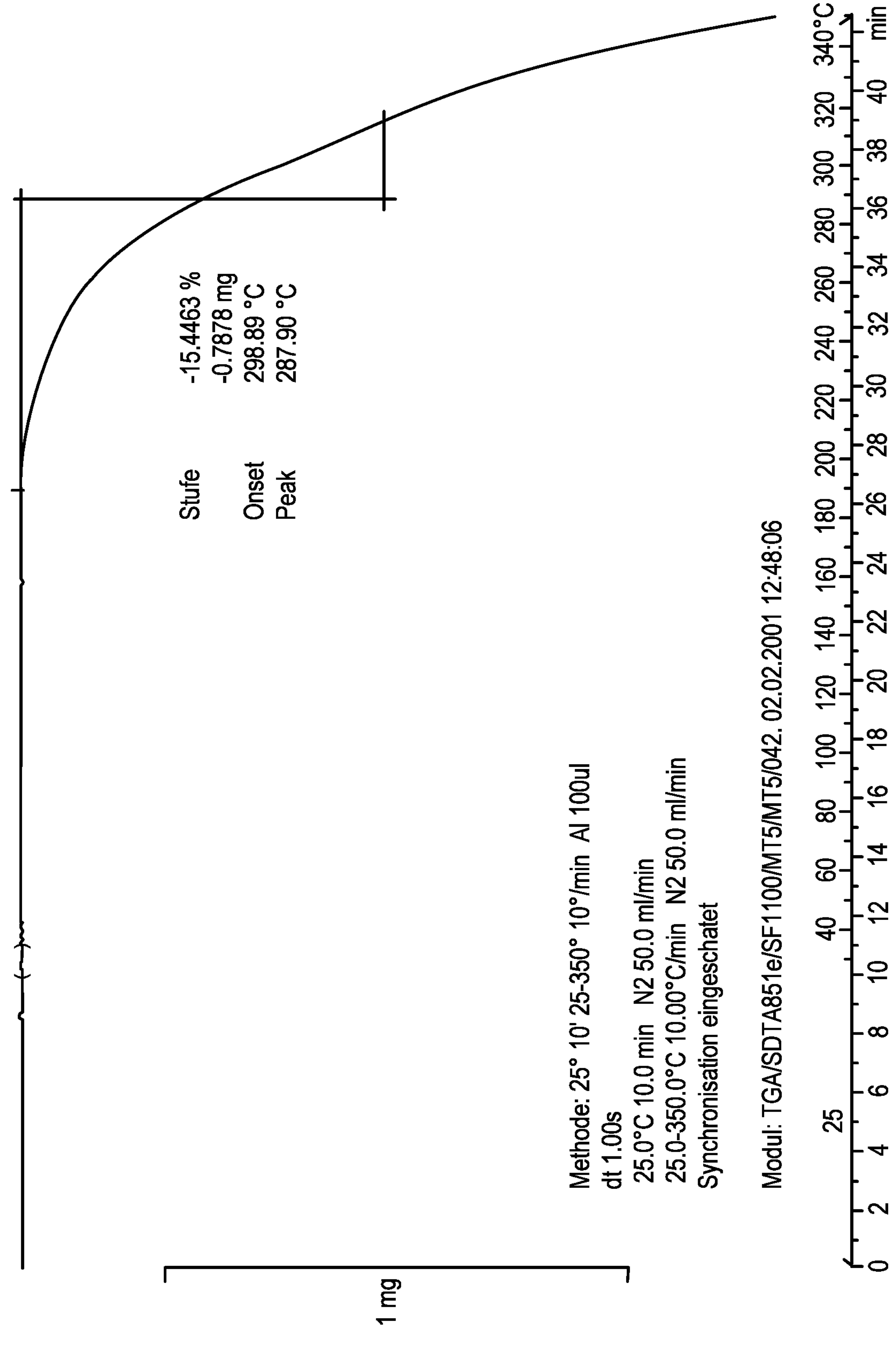
FIG. 3 shows the Thermogravimetric Analysis (TGA) pattern of Form 1.

In some embodiments, crystalline Form 1 of Compound I has a TGA pattern substantially the same as shown in FIG. 3. In some embodiments, crystalline Form 1 has a TGA pattern with a 15.4% w/w loss from about 287.9° C. to about 298.9° C. In some embodiments, crystalline Form 1 has a TGA pattern with less than 1% weight loss up to 200° C.

In some embodiments, crystalline Form 1 of Compound I has no reversible water uptake (~-0.1% w/w) between 0 and 95% Relative Humidity (RH). In some embodiments, crystalline Form 1 of Compound I has no reversible water uptake between 0 and 95% Relative Humidity (RH). In some embodiments, crystalline Form 1 of Compound I has <1% w/w reversible water uptake between 0 and 95% Relative Humidity (RH). In some embodiments, crystalline Form 1 of Compound I has ~-0.1% w/w reversible water uptake between 0 and 95% Relative Humidity (RH).

In some embodiments, crystalline Form 1 of Compound I has an FTIR spectrum with a peak at about 1739.6 $cm^{-1}$.

In some embodiments, crystalline Form 1 of Compound I has an unchanged FTIR after storage at 75% RH and 80° C. over 7 days.

In some embodiments, crystalline Form 1 of Compound I has a crystal structure characterized by atomic coordinates substantially as in Table 2; wherein the measurement of the crystal structure is carried out at 293 K. In some embodiments, crystalline Form 1 has a crystal structure characterized by unit cell parameters substantially equal to: a=6.521 (6) Å; b=10.548(9) Å; c=17.453(15) Å; α=104.080(16)°; β=92.430(16)°; γ=101.081(17)°; and having a triclinic space group=P1 (Z=2); wherein the measurement of the crystal structure is carried out at 293 K. In some embodiments, crystalline Form 1 has a crystal structure characterized by unit cell parameters substantially equal to: a=6.521(6) Å; b=10.548(9) Å; c=17.453(15) Å; α=104.080(16)°; β=92.430(16)°; γ=101.081(17)°; and having a triclinic space group=P1 (Z=2); wherein the measurement of the crystal structure is carried out at 293 K and is characterized by atomic coordinates substantially as in Table 2.

In some embodiments, crystalline Form 1 of Compound I has a ssNMR spectrum substantially the same as shown in FIG. 4. In some embodiments, crystalline Form 1 has a ssNMR spectrum characterized by resonances (δc) at 23.35, 124.43, 126.78, 127.42, and 136.47 ppm. In some embodiments, crystalline Form 1 has a ssNMR spectrum further characterized by resonances (δc) at 54.41, 65.40, 138.94, 142.61, 148.68, 152.19, and 174.59 ppm. In some embodiments, crystalline Form 1 has a ssNMR spectrum characterized by resonances (δc) at 23.35, 36.40, 44.12, 45.70, 54.41, 65.40, 71.58, 110.97, 114.45, 121.00, 124.43, 126.78, 127.42, 131.27, 136.47, 138.94, 142.61, 148.68, 152.19, 172.07, and 174.59 ppm.

In some embodiments, crystalline Form 1 of Compound I converts to crystalline Form 2 when slurried in solvent at a temperature of 60° C. or above. In some embodiments, crystalline Form 1 converts to crystalline Form 2 when slurried in MEK or 1-pentanol at a temperature of 60° C. or 70° C. In some embodiments, form conversion is determined by FTIR.

In some embodiments, crystalline Form 1 of Compound I is anhydrous.

Crystalline Form 2 of Compound I

Figure 5:
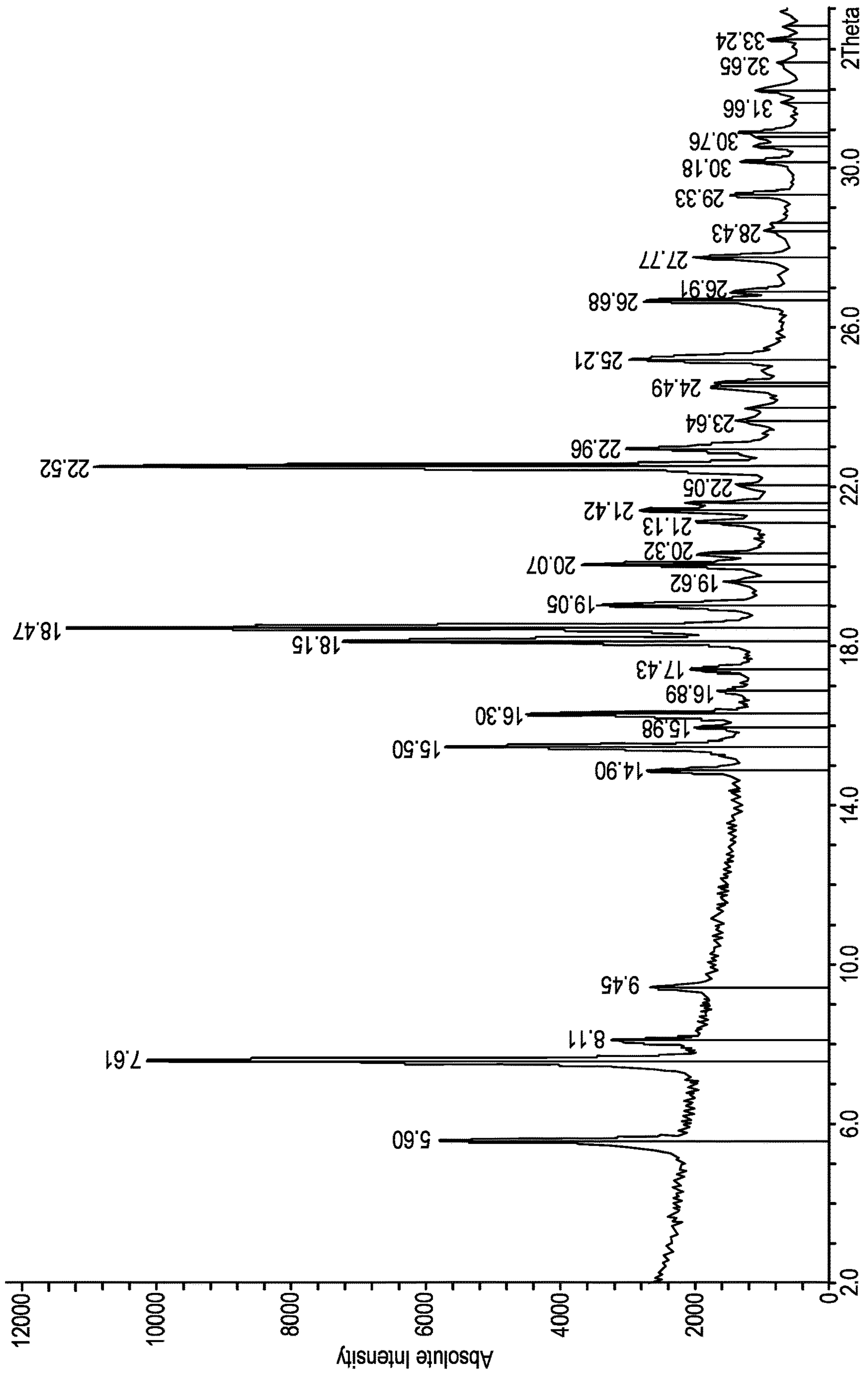
FIG. 5 shows the X-ray powder diffraction (XRPD) pattern of Form 2.

Also provided herein is crystalline Form 2 of Compound I. Some embodiments provide a composition comprising crystalline Form 2 of Compound I. In some embodiments, crystalline Form 2 of Compound I is characterized as having:

- an X-ray powder diffraction (XRPD) pattern substantially the same as shown in FIG. 5, as measured using Cu (Kα) radiation;
- an X-ray powder diffraction (XRPD) pattern with peaks at 5.6±0.2° 2-Theta, 7.6±0.2° 2-Theta, 9.4±0.2° 2-Theta, 15.5±0.2° 2-Theta, and 16.3±0.2° 2-Theta, as measured using Cu (Kα) radiation;
- a Fourier Transform IR Spectroscopy (FTIR) pattern with a peak at about 1731.7 $cm^{-1}$;
- unit cell parameters substantially equal to the following at 293 K:

| | |
|---|---|
| Crystal System | orthorhombic |
| Space Group | Pbca; Z = 8 |
| a (Å) | 6.2823(10) |
| b (Å) | 23.285(4) |
| c (Å) | 31.614(6) |
| α (°) | 90.00° |
| β (°) | 90.00° |
| γ (°) | 90.00° |
| V (Å$^3$) | 4624.5(14) |
| Calculated Density (Mg/m$^3$) | 1.280 |
| Unique Reflections | 4163 |

Figure 7:
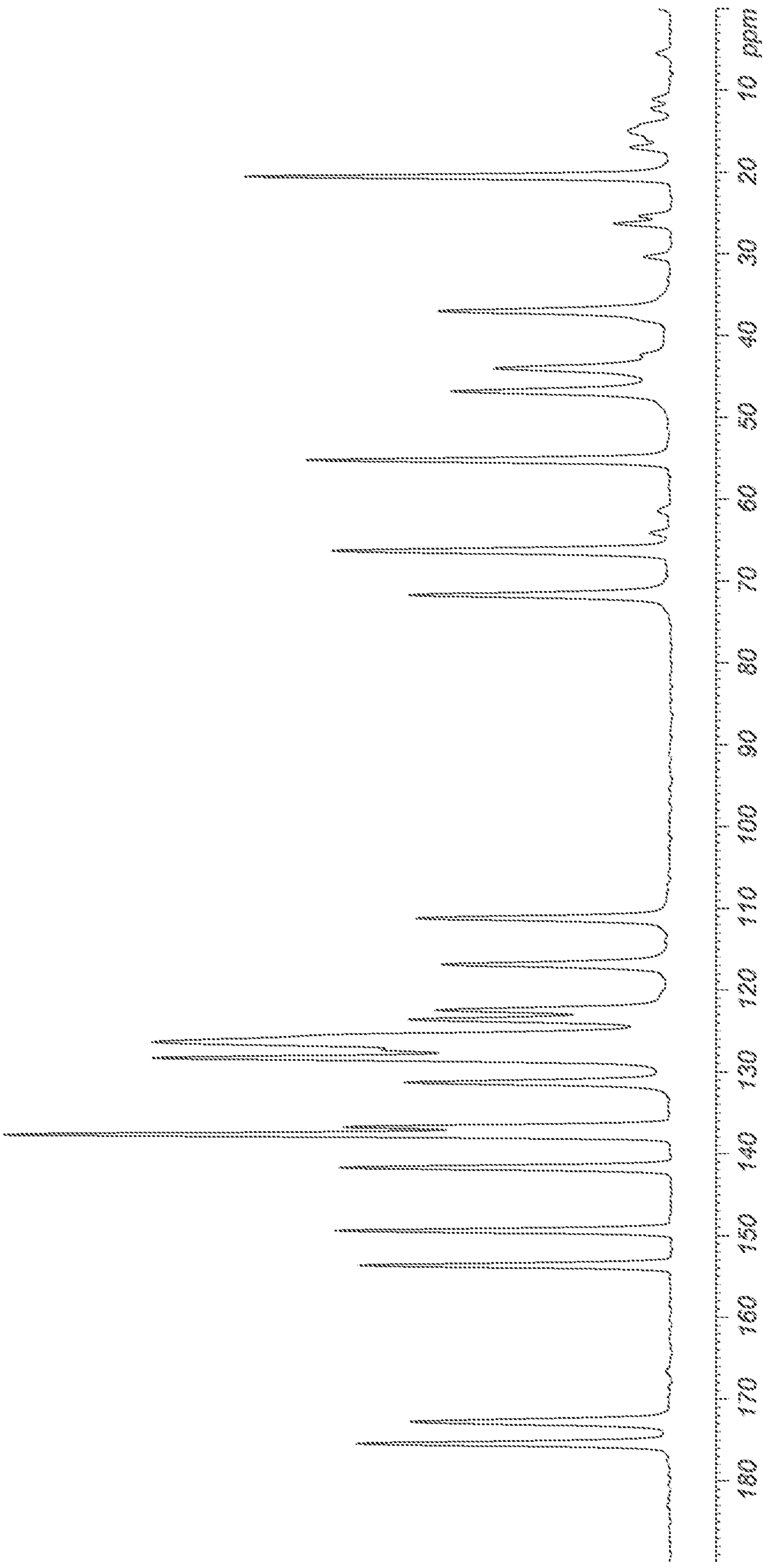
FIG. 7 shows the Solid State $^{13}$Carbon NMR Spectrum of Form 2.

- a Solid State $^{13}$Carbon Nuclear Magnetic Resonance (ssNMR) spectrum substantially the same as shown in FIG. 7;
- a Solid State $^{13}$Carbon Nuclear Magnetic Resonance (ssNMR) spectrum characterized by resonances (δc) at 20.59, 126.39, 128.34, and 137.69 ppm; or
- combinations thereof.

In some embodiments, crystalline Form 2 of Compound I is characterized as having an X-ray powder diffraction (XRPD) pattern substantially the same as shown in FIG. 5, as measured using Cu (Kα) radiation.

In some embodiments, crystalline Form 2 of Compound I is characterized as having an XRPD pattern substantially the same as shown in FIG. 5, as measured using Cu (Kα) radiation; and a Fourier Transform IR Spectroscopy (FTIR) pattern with a peak at about 1731.7 $cm^{-1}$.

In some embodiments, crystalline Form 2 of Compound I is characterized as having an XRPD pattern substantially the same as shown in FIG. 5, as measured using Cu (Kα) radiation; and a Solid State $^{13}$Carbon Nuclear Magnetic Resonance (ssNMR) spectrum substantially the same as shown in FIG. 7.

Figure 6:
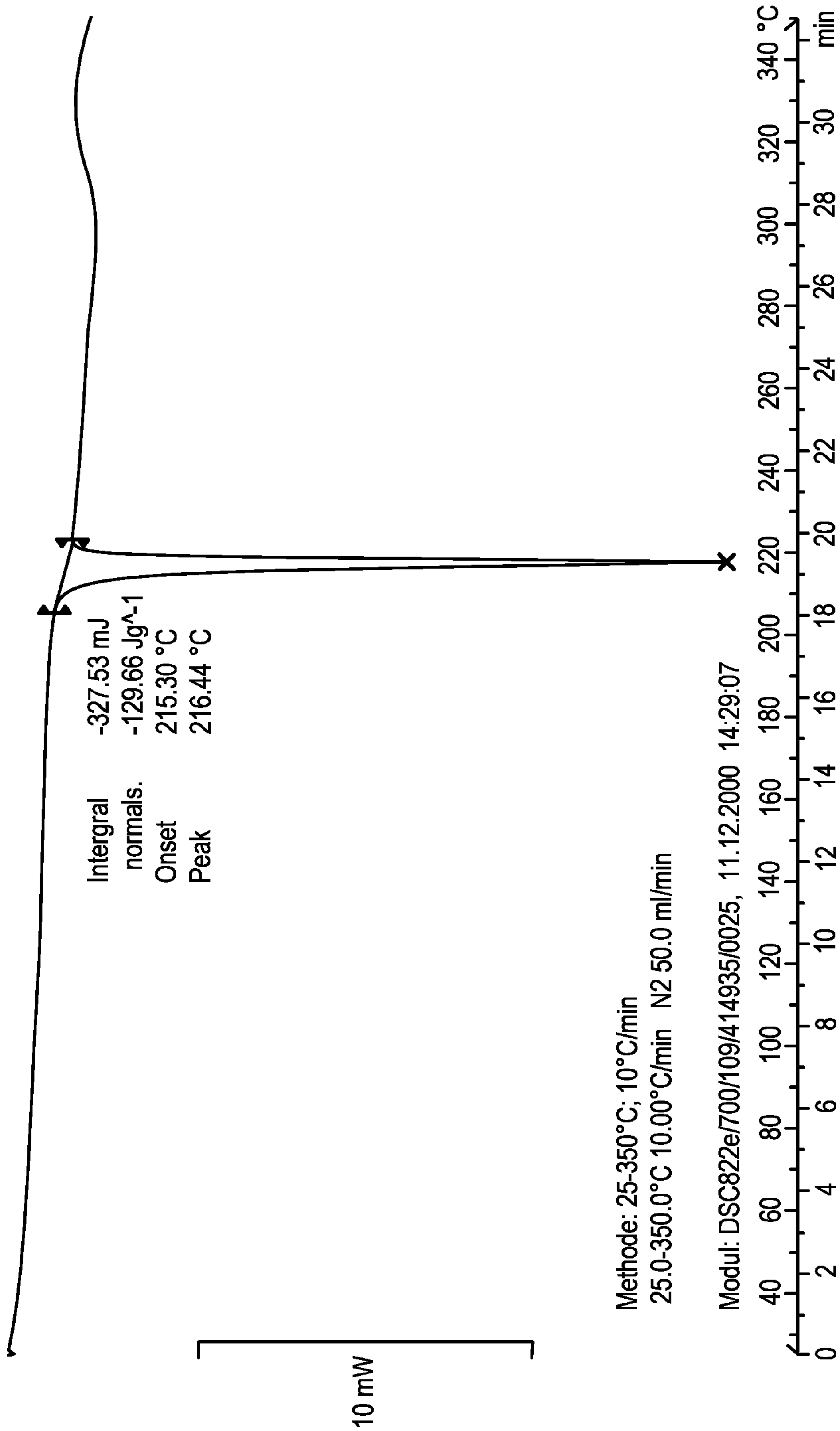
FIG. 6 shows the Differential Scanning calorimetry (DSC) thermogram of Form 2.

In some embodiments, crystalline Form 2 of Compound I is characterized as having an XRPD pattern substantially the same as shown in FIG. 5, as measured using Cu (Kα) radiation; and a Differential Scanning calorimetry (DSC) thermogram substantially the same as shown in FIG. 6.

In some embodiments, crystalline Form 2 of Compound I is characterized as having an X-ray powder diffraction (XRPD) pattern with peaks at 5.6±0.2° 2-Theta, 7.6±0.2° 2-Theta, 9.4±0.2° 2-Theta, 15.5±0.2° 2-Theta, and 16.3±0.2° 2-Theta, as measured using Cu (Kα) radiation.

In some embodiments, crystalline Form 2 of Compound I is characterized as having an XRPD pattern with peaks at 5.6±0.2° 2-Theta, 7.6±0.2° 2-Theta, 9.4±0.2° 2-Theta, 15.5±0.2° 2-Theta, and 16.3±0.2° 2-Theta, as measured using Cu (Kα) radiation; and a Differential Scanning calorimetry (DSC) thermogram with an endothermic event having an onset at about 215.3° C. and a peak at about 216.4° C.

In some embodiments, crystalline Form 2 of Compound I is characterized as having an XRPD pattern with peaks at 5.6±0.2° 2-Theta, 7.6±0.2° 2-Theta, 9.4±0.2° 2-Theta, 15.5±0.2° 2-Theta, and 16.3±0.2° 2-Theta, as measured using Cu (Kα) radiation; and a Fourier Transform IR Spectroscopy (FTIR) pattern with a peak at about 1731.7 $cm^{-1}$.

In some embodiments, crystalline Form 2 of Compound I is characterized as having an XRPD pattern with peaks at 5.6±0.2° 2-Theta, 7.6±0.2° 2-Theta, 9.4±0.2° 2-Theta, 15.5±0.2° 2-Theta, and 16.3±0.2° 2-Theta, as measured using Cu (Kα) radiation; and a Solid State $^{13}$Carbon Nuclear Magnetic Resonance (ssNMR) spectrum characterized by resonances (δc) at 20.59, 126.39, 128.34, and 137.69 ppm.

In some embodiments, crystalline Form 2 of Compound I is characterized as having a Solid State $^{13}$Carbon Nuclear Magnetic Resonance (ssNMR) spectrum substantially the same as shown in FIG. 7.

In some embodiments, crystalline Form 2 of Compound I is characterized as having a Solid State $^{13}$Carbon Nuclear Magnetic Resonance (ssNMR) spectrum substantially the same as shown in FIG. 7; and a Fourier Transform IR Spectroscopy (FTIR) pattern with a peak at about 1731.7 $cm^{-1}$.

In some embodiments, crystalline Form 2 of Compound I is characterized as having a Solid State $^{13}$Carbon Nuclear Magnetic Resonance (ssNMR) spectrum characterized by resonances (δc) at 20.59, 126.39, 128.34, and 137.69 ppm.

In some embodiments, crystalline Form 2 of Compound I is characterized as having a Solid State $^{13}$Carbon Nuclear Magnetic Resonance (ssNMR) spectrum characterized by resonances (δc) at 20.59, 126.39, 128.34, and 137.69 ppm; and a Differential Scanning calorimetry (DSC) thermogram with an endothermic event having an onset at about 215.3° C. and a peak at about 216.4° C. In some embodiments, crystalline Form 2 of Compound I is characterized as having a Solid State $^{13}$Carbon Nuclear Magnetic Resonance (ssNMR) spectrum characterized by resonances (δc) at 20.59, 126.39, 128.34, and 137.69 ppm; and a Fourier Transform IR Spectroscopy (FTIR) pattern with a peak at about 1731.7 $cm^{-1}$.

In some embodiments, crystalline Form 2 of Compound I is characterized as having a Fourier Transform IR Spectroscopy (FTIR) pattern with a peak at about 1731.7 $cm^{-1}$.

In some embodiments, crystalline Form 2 has a TGA pattern with less than 1% weight loss up to 200° C. In some embodiments, crystalline Form 2 of Compound I has a DSC thermogram substantially the same as shown in FIG. 6. In some embodiments, crystalline Form 2 has a DSC thermogram with an endothermic event having an onset at about 215.3° C. and a peak at about 216.4° C.

In some embodiments, crystalline Form 2 of Compound I has an FTIR spectrum with a peak at about 1731.7 $cm^{-1}$. In some embodiments, crystalline Form 2 of Compound I has an unchanged FTIR after storage at 75% RH and 80° C. over 7 days.

In some embodiments, crystalline Form 2 of Compound I has a crystal structure characterized by atomic coordinates substantially as in Table 4; wherein the measurement of the crystal structure is carried out at 293 K. In some embodiments, crystalline Form 2 has a crystal structure characterized by unit cell parameters substantially equal to: a=6.2823 (10) Å; b=23.285(4) Å; c=31.614(6) Å; α=90.00°; β=90.00°; γ=90.00°; and having an orthorhombic space group=Pbca (Z=8); wherein the measurement of the crystal structure is carried out at 293 K.

In some embodiments, crystalline Form 2 of Compound I has a ssNMR spectrum substantially the same as shown in FIG. 7. In some embodiments, crystalline Form 2 has a ssNMR spectrum characterized by resonances (δc) at 20.59, 126.39, 128.34, and 137.69 ppm. In some embodiments, crystalline Form 2 has a ssNMR spectrum further characterized by resonances (δc) at 55.25, 66.34, 136.78, 141.73, 149.44, 153.68, and 175.49 ppm. In some embodiments, crystalline Form 2 has a ssNMR spectrum characterized by resonances (δc) at 20.59, 37.04, 44.03, 46.84, 55.25, 66.34, 71.74, 111.25, 116.90, 122.48, 123.63, 126.39, 128.34, 131.33, 136.78, 137.69, 141.73, 149.44, 153.68, 172.82, and 175.49 ppm.

In some embodiments, crystalline Form 2 of Compound I converts to crystalline Form 1 when slurried in solvent at a temperature of 50° C. or below. In some embodiments, crystalline Form 2 converts to crystalline Form 1 when slurried in MEK or methanol at a temperature of 40° C. or 50° C. In some embodiments, crystalline Form 2 converts to crystalline Form 1 when slurried in MEK at room temperature (~25° C.). In some embodiments, form conversion is determined by FTIR.

Crystalline Form 3 of Compound I

Figure 10:
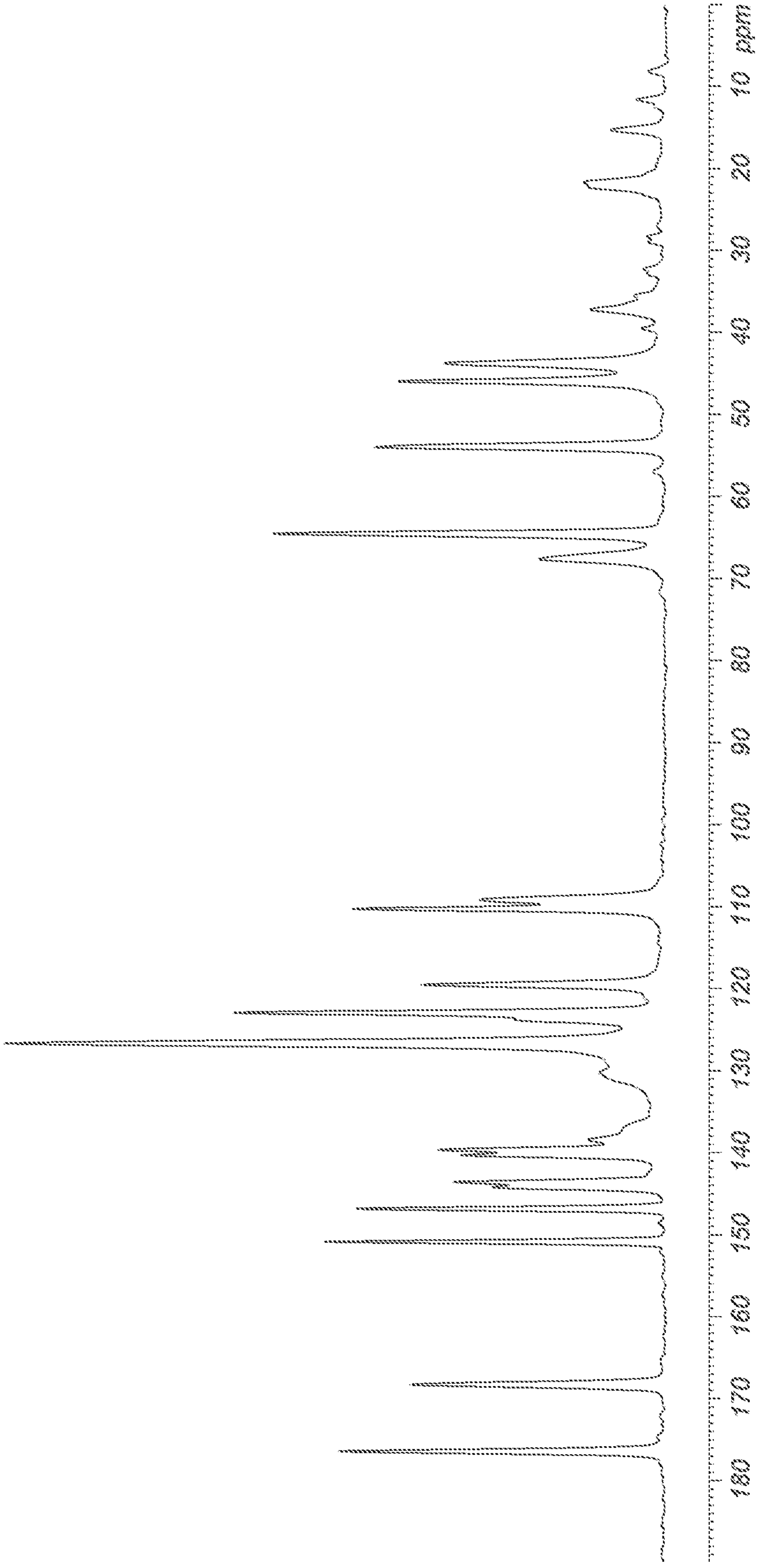
FIG. 10 shows the Solid State $^{13}$Carbon NMR Spectrum of Form 3.

Also provided herein is the crystalline Form 3 of Compound I. Some embodiments provide a composition comprising crystalline Form 3 of Compound I. In some embodiments, crystalline Form 3 of Compound I is characterized as having: an X-ray powder diffraction (XRPD) pattern substantially the same as shown in FIG. 8, as measured using Cu (Kα) radiation; an X-ray powder diffraction (XRPD) pattern with peaks at 4.2±0.2° 2-Theta, 6.8±0.2° 2-Theta, 15.1±0.2° 2-Theta, 25.0±0.2° 2-Theta, 25.5±0.2° 2-Theta, and 26.4±0.2° 2-Theta, as measured using Cu (Kα) radiation; a Fourier Transform IR Spectroscopy (FTIR) pattern with a peak at about 1722.0 $cm^{-1}$; a Solid State $^{13}$Carbon Nuclear Magnetic Resonance (ssNMR) spectrum substantially the same as shown in FIG. 10; a Solid State $^{13}$Carbon Nuclear Magnetic Resonance (ssNMR) spectrum characterized by resonances (δc) at 64.56, 67.67, 122.99, and 126.71 ppm; or combinations thereof.

Figure 8:
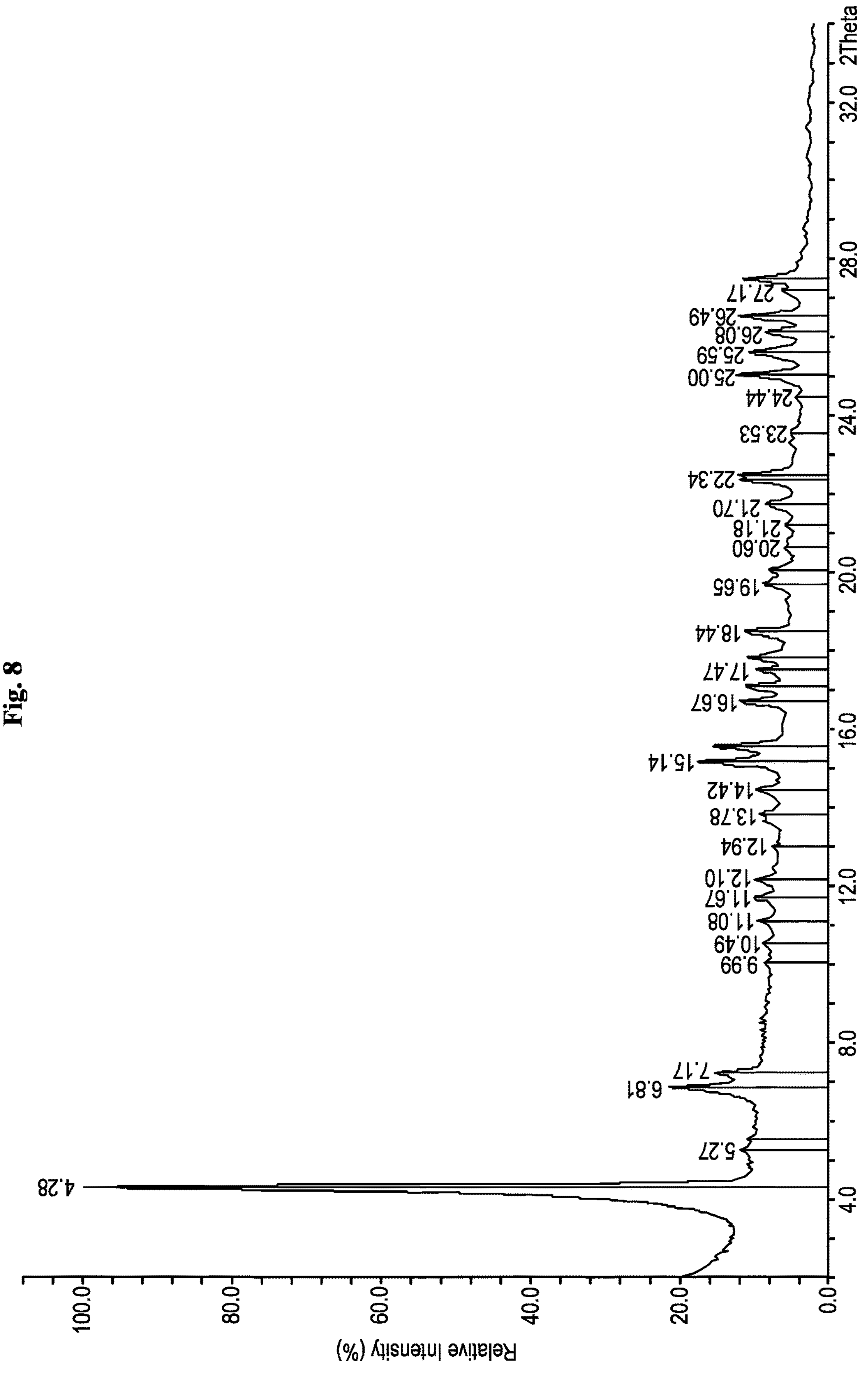
FIG. 8 shows the X-ray powder diffraction (XRPD) pattern of Form 3.

In some embodiments, crystalline Form 3 of Compound I is characterized as having an X-ray powder diffraction (XRPD) pattern substantially the same as shown in FIG. 8, as measured using Cu (Kα) radiation.

Figure 11:
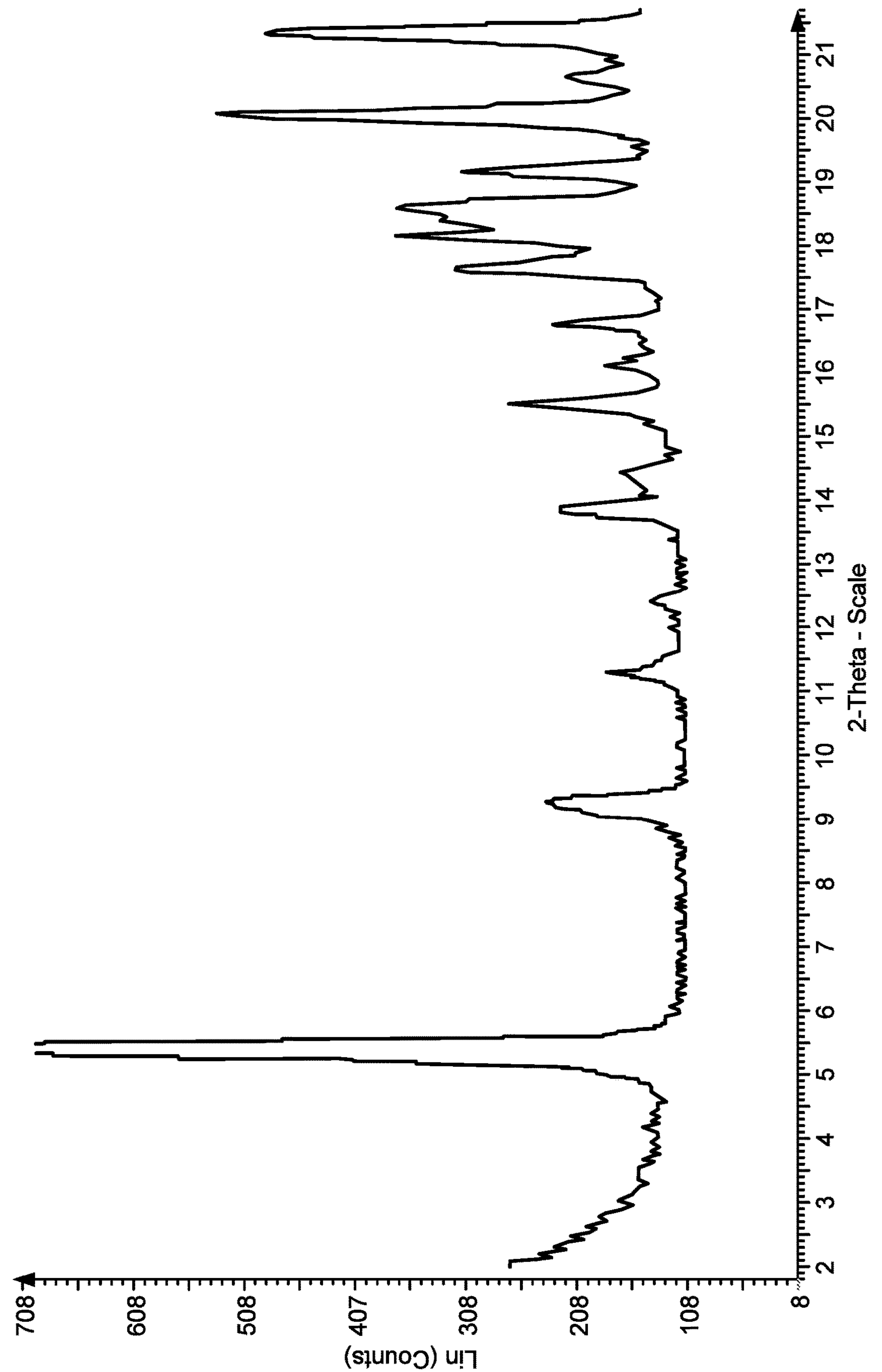
FIG. 11 shows the X-ray powder diffraction (XRPD) pattern of Form 4.

In some embodiments, crystalline Form 3 of Compound I is characterized as having an XRPD pattern substantially the same as shown in FIG. 8, as measured using Cu (Kα) radiation; and a Differential Scanning calorimetry (DSC) thermogram substantially the same as shown in FIG. 11.

In some embodiments, crystalline Form 3 of Compound I is characterized as having an XRPD pattern substantially the same as shown in FIG. 8, as measured using Cu (Kα) radiation; and a Fourier Transform IR Spectroscopy (FTIR) pattern with a peak at about 1722.0 $cm^{-1}$.

In some embodiments, crystalline Form 3 of Compound I is characterized as having an X-ray powder diffraction (XRPD) pattern with peaks at 4.2±0.2° 2-Theta, 6.8±0.2° 2-Theta, 15.1±0.2° 2-Theta, 25.0±0.2° 2-Theta, 25.5±0.2° 2-Theta, and 26.4±0.2° 2-Theta, as measured using Cu (Kα) radiation.

In some embodiments, crystalline Form 3 of Compound I is characterized as having an XRPD pattern with peaks at 4.2±0.2° 2-Theta, 6.8±0.2° 2-Theta, 15.1±0.2° 2-Theta, 25.0±0.2° 2-Theta, 25.5±0.2° 2-Theta, and 26.4±0.2° 2-Theta, as measured using Cu (Kα) radiation; and a Differential Scanning calorimetry (DSC) thermogram with one or more endothermic events having: an onset at about 204.2° C. and a peak at about 205.3° C.; and/or an onset at about 213.6° C. and a peak at about 215.8° C.

In some embodiments, crystalline Form 3 of Compound I is characterized as having an XRPD pattern with peaks at 4.2±0.2° 2-Theta, 6.8±0.2° 2-Theta, 15.1±0.2° 2-Theta, 25.0±0.2° 2-Theta, 25.5±0.2° 2-Theta, and 26.4±0.2° 2-Theta, as measured using Cu (Kα) radiation; and a Fourier Transform IR Spectroscopy (FTIR) pattern with a peak at about 1722.0 $cm^{-1}$. In some embodiments, crystalline Form 3 of Compound I is characterized as having a Fourier Transform IR Spectroscopy (FTIR) pattern with a peak at about 1722.0 $cm^{-1}$.

In some embodiments, crystalline Form 3 of Compound I is characterized as having a Solid State $^{13}$Carbon Nuclear Magnetic Resonance (ssNMR) spectrum substantially the same as shown in FIG. 10.

Figure 9:
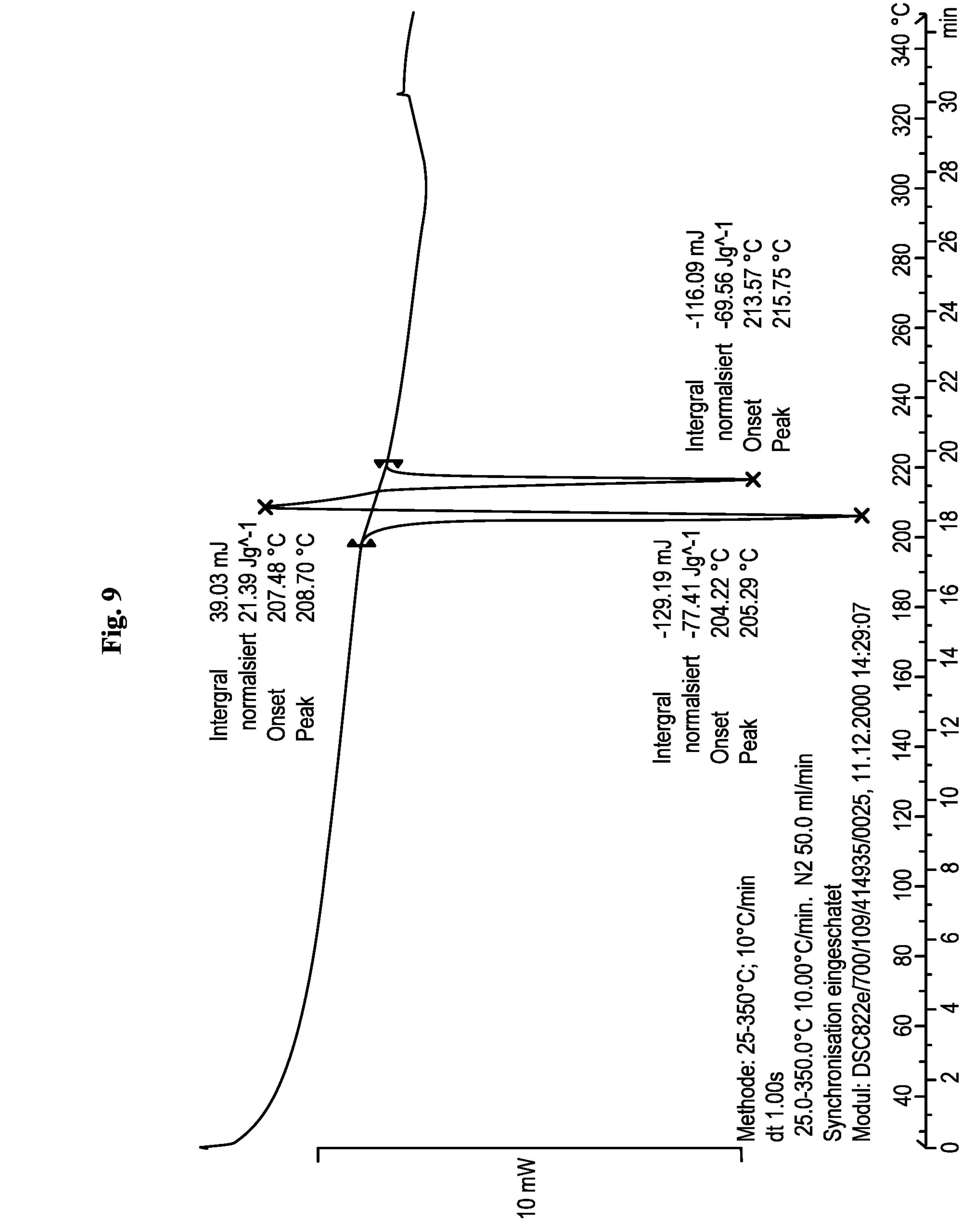
FIG. 9 shows the Differential Scanning calorimetry (DSC) thermogram of Form 3.

In some embodiments, crystalline Form 3 of Compound I is characterized as having a Solid State $^{13}$Carbon Nuclear Magnetic Resonance (ssNMR) spectrum characterized by resonances (δc) at 64.56, 67.67, 122.99, and 126.71 ppm. In some embodiments, crystalline Form 3 has a TGA pattern with less than 1% weight loss up to 200° C. In some embodiments, crystalline Form 3 of Compound I has a DSC thermogram substantially the same as shown in FIG. 9. In some embodiments, crystalline Form 3 has a DSC thermogram with one or more endothermic events having: an onset at about 204.2° C. and a peak at about 205.3° C.; and/or an onset at about 213.6° C. and a peak at about 215.8° C. In some embodiments, crystalline Form 3 has a DSC thermogram with two endothermic events having: an onset at about 204.2° C. and a peak at about 205.3° C.; and an onset at about 213.6° C. and a peak at about 215.8° C. In some embodiments, crystalline Form 3 has an FTIR spectrum with a peak at about 1722.0 $cm^{-1}$. In some embodiments, crystalline Form 3 of Compound I has an unchanged FTIR after storage at 75% RH and 80° C. over 7 days.

In some embodiments, crystalline Form 3 of Compound I has a ssNMR spectrum substantially the same as shown in FIG. 10. In some embodiments, crystalline Form 3 has a ssNMR spectrum characterized by resonances (δc) at 64.56, 67.67, 122.99, and 126.71 ppm. In some embodiments, crystalline Form 3 has a ssNMR spectrum further characterized by resonances (δc) at 110.33, 146.87, 150.90, and 176.47 ppm. In some embodiments, crystalline Form 3 has a ssNMR spectrum characterized by resonances (δc) at 43.81, 46.00, 54.01, 64.56, 67.67, 109.22, 110.33, 119.58, 122.99, 126.71, 139.68, 140.34, 143.63, 144.25, 146.87, 150.90, 168.32, and 176.47 ppm. In some embodiments, crystalline Form 3 has a ssNMR spectrum characterized by resonances (δc) at 21.72, 22.23, 43.81, 46.00, 54.01, 64.56, 67.67, 109.22, 110.33, 119.58, 122.99, 126.71, 130.28, 138.46, 139.68, 140.34, 143.63, 144.25, 146.87, 150.90, 168.32, and 176.47 ppm.

In some embodiments, crystalline Form 3 of Compound I converts to crystalline Form 1 when slurried in solvent at room temperature (~25° C.). In some embodiments, crystalline Form 3 converts to crystalline Form 1 when slurried in methanol, MEK, methyl-THF, or ethyl acetate at room temperature (~25° C.). In some embodiments, form conversion is determined by FTIR.

Crystalline Form 4 of Compound I

Figure 13:
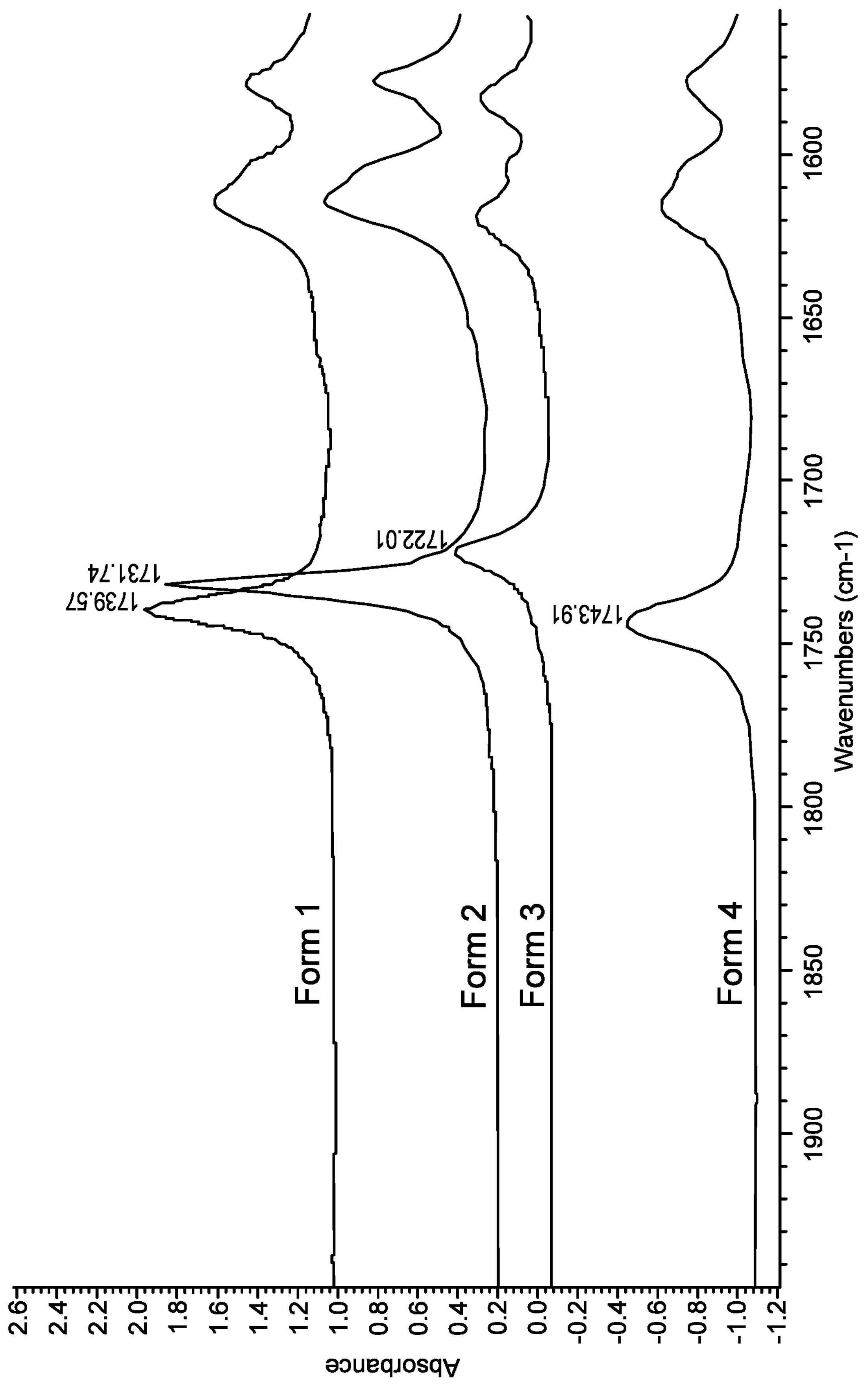
FIG. 13 shows the Fourier Transform IR Spectroscopy (FTIR) pattern overlay of Forms 1, 2, 3, and 4.

Also provided herein is the crystalline Form 4 of Compound I. Some embodiments provide a composition comprising crystalline Form 4 of Compound I. In some embodiments, crystalline Form 4 of Compound I is characterized as having: an X-ray powder diffraction (XRPD) pattern substantially the same as shown in FIG. 11; a Differential Scanning calorimetry (DSC) thermogram substantially the same as shown in FIG. 13; a Fourier Transform IR Spectroscopy (FTIR) pattern with a peak at about 1743.9 $cm^{-1}$; or combinations thereof.

Figure 12:
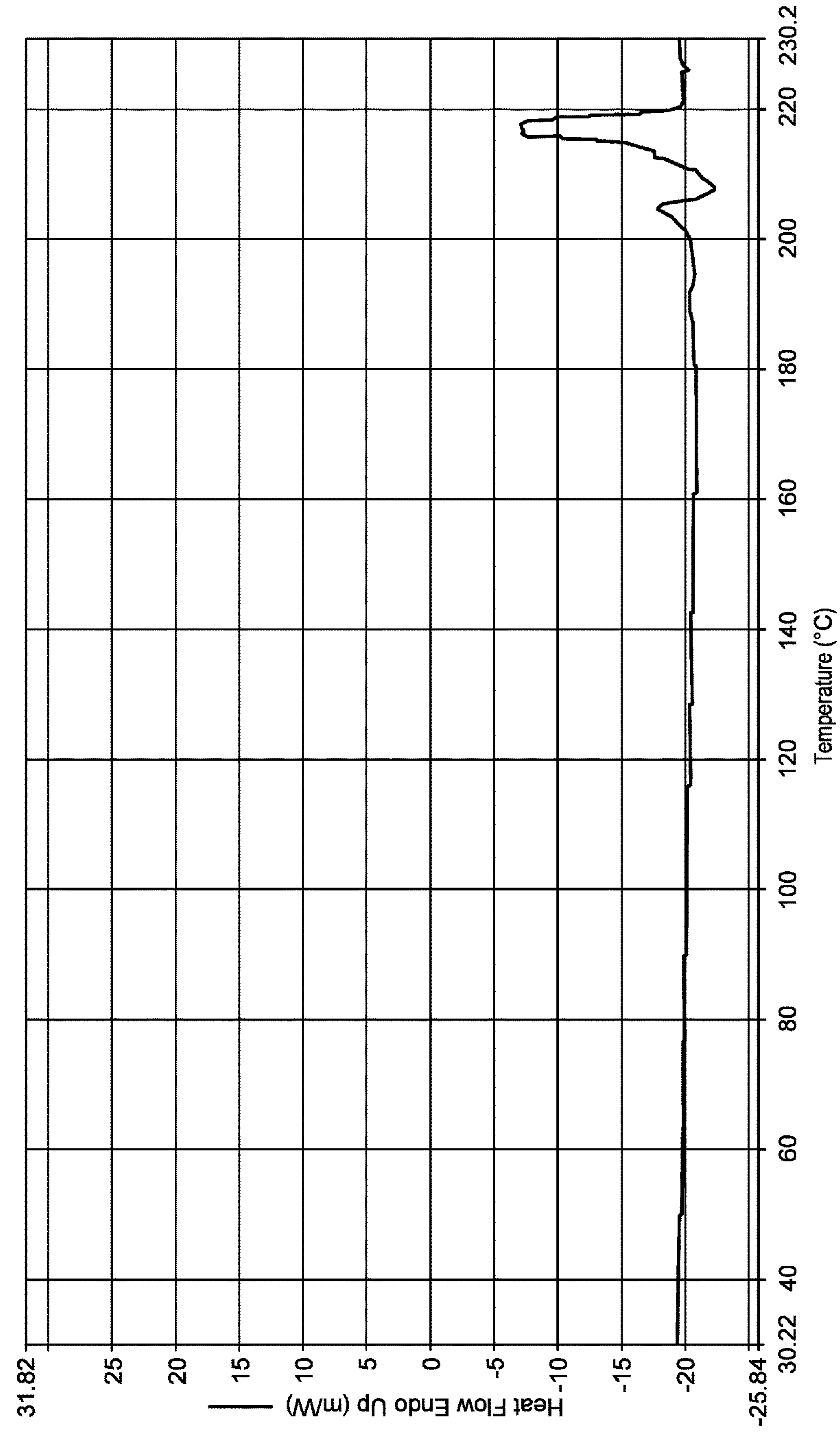
FIG. 12 shows the Differential Scanning calorimetry (DSC) thermogram of Form 4.

In some embodiments, crystalline Form 4 of Compound I has an XRPD pattern substantially the same as shown in FIG. 11. In some embodiments, crystalline Form 4 of Compound I has a DSC thermogram substantially the same as shown in FIG. 12. In some embodiments, crystalline Form 4 has an FTIR spectrum with a peak at about 1743.9 $cm^{-1}$. In some embodiments, crystalline Form 4 has a TGA pattern with less than 1% weight loss up to 200° C.

Amorphous Phase of Compound I

Figure 14:
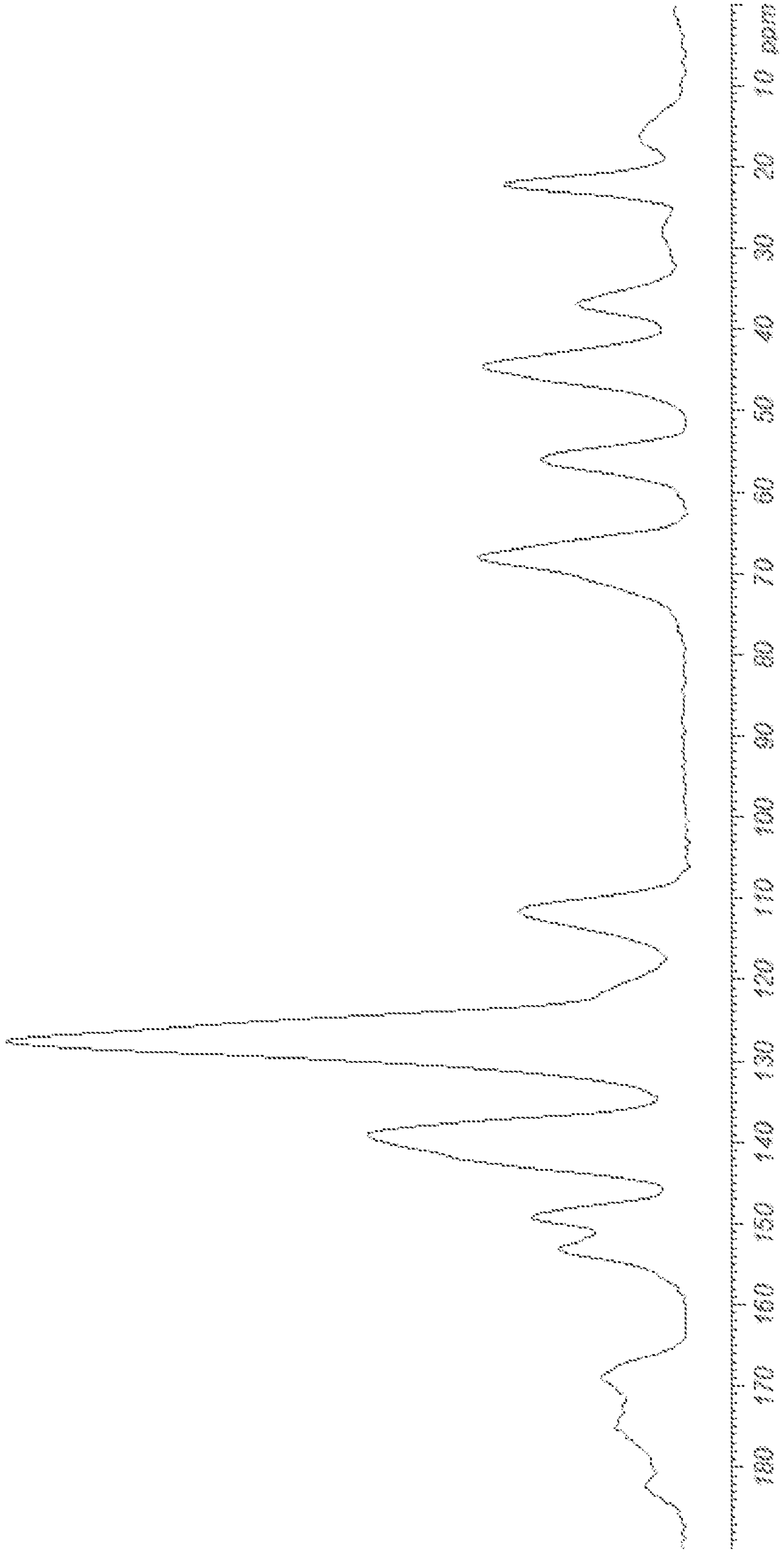
FIG. 14 shows the Solid State $^{13}$Carbon NMR Spectrum of Amorphous Form.

Also provided herein is the amorphous phase of Compound I. Some embodiments provide a composition comprising the amorphous phase of Compound I. In some embodiments, the amorphous phase of Compound I is characterized as having an XRPD pattern showing a lack of crystallinity. In some embodiments, the amorphous phase of Compound I is characterized as having a Solid State $^{13}$Carbon Nuclear Magnetic Resonance (ssNMR) spectrum substantially the same as shown in FIG. 14.

Described herein is a pharmaceutical composition of Compound I substantially free of impurities. In some embodiments, the pharmaceutical composition is substantially free of Compound I impurities. In some embodiments, the pharmaceutical composition comprises less than about 1% w/w of Compound I impurities. In some embodiments, the pharmaceutical composition comprises less than about 1% w/w, less than about 0.75% w/w, less than about 0.50% w/w, less than about 0.25% w/w, less than about 0.20% w/w, less than about 0.15% w/w, less than about 0.10% w/w, or less than about 0.05% w/w of Compound I impurities. In some embodiments, the amount of Compound I impurities is undetectable. In some embodiments, the amount of Compound I impurities is undetectable by NMR, HPLC, or the like.

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zürich:Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviors. Also, because the salt-forming molecule can be in equilibrium with a neutral form, passage through biological membranes can be adjusted.

In some embodiments, pharmaceutically acceptable salts of Compound I are obtained by reacting Compound I with a base. In some embodiments, the base is an inorganic base. In such situations, the acidic proton of Compound I is replaced by a metal ion, e.g., lithium, sodium, potassium, magnesium, or calcium. Acceptable inorganic bases used to form salts with Compound I include, but are not limited to, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, or magnesium salt. In some embodiments, described herein is the sodium salt of Compound I.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

Unless otherwise stated, the following terms used in this application have the definitions given below. The use of the term “including” as well as other forms, such as “include”, “includes,” and “included,” is not limiting. The section headings used herein are for organizational purposes only and are not to be construed as limiting the subject matter described.

The term “acceptable” with respect to a formulation, composition or ingredient, as used herein, means having no persistent detrimental effect on the general health of the subject being treated.

The term “modulate” as used herein, means to interact with a target either directly or indirectly so as to alter the activity of the target, including, by way of example only, to enhance the activity of the target, to inhibit the activity of the target, to limit the activity of the target, or to extend the activity of the target.

The term “modulator” as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an agonist.

The terms “administer,” “administering”, “administration,” and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms “co-administration” or the like, as used herein, are meant to encompass administration of the selected therapeutic agents to a single patient, and are intended to include treatment regimens in which the agents are administered by the same or different route of administration or at the same or different time.

The terms “effective amount” or “therapeutically effective amount,” as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an “effective amount” for therapeutic uses is the amount of the composition comprising a compound as disclosed herein required to provide a clinically significant decrease in disease symptoms. An appropriate “effective” amount in any individual case is optionally determined using techniques, such as a dose escalation study.

The terms “enhance” or “enhancing,” as used herein, means to increase or prolong either in potency or duration a desired effect. Thus, in regard to enhancing the effect of therapeutic agents, the term “enhancing” refers to the ability to increase or prolong, either in potency or duration, the effect of other therapeutic agents on a system. An “enhancing-effective amount,” as used herein, refers to an amount adequate to enhance the effect of another therapeutic agent in a desired system.

The term “subject” or “patient” encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms “treat,” “treating” or “treatment,” as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be effected by any method that enables delivery of the compounds to the site of action.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added.

It should be understood that in addition to the ingredients particularly mentioned above, the compounds and compositions described herein may include other agents conventional in the art having regard to the type of formulation in question, for example those suitable for oral administration may include flavoring agents.

Methods of Dosing and Treatment Regimens

In one embodiment, the compounds disclosed herein, or a pharmaceutically acceptable salt thereof, are used in the preparation of medicaments for the treatment of diseases or conditions in a mammal that would benefit from modulation of $LPA_1$ receptor activity. Methods for treating any of the diseases or conditions described herein in a mammal in need of such treatment, involves administration of pharmaceutical compositions that include at least one compound disclosed herein or a pharmaceutically acceptable salt thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 25 mg-1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound disclosed herein, or a pharmaceutically acceptable salt thereof, described herein are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

In any of the aforementioned aspects are further embodiments in which the effective amount of the compound disclosed herein, or a pharmaceutically acceptable salt thereof, is: (a) systemically administered to the mammal; and/or (b) administered orally to the mammal.

In some embodiments, compound I, or a pharmaceutically acceptable salt thereof, is administered is dose selected from about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, and about 400 mg. In some embodiments, the dose is administered once a day. In some embodiments, the dose is administered twice a day.

Provided is a method of treating systemic sclerosis in a patient in need thereof, comprising: administering to the patient a therapeutically effective amount of Compound I, or a pharmaceutically acceptable salt thereof, for a dosing period of at least about 24 consecutive weeks.

Also provided is a method for reducing fibrosis in a cell or tissue, the method comprising contacting the cell or tissue with Compound I, or a pharmaceutically acceptable salt thereof, in an amount and for a time sufficient to decrease or inhibit the fibrosis.

In certain embodiments, the systemic sclerosis is chosen from limited cutaneous systemic sclerosis, diffuse cutaneous systemic sclerosis, and systemic sclerosis sine scleroderma.

In certain embodiments, the systemic sclerosis is limited cutaneous systemic sclerosis.

In certain embodiments, the systemic sclerosis is systemic sclerosis sine scleroderma.

In certain embodiments, the systemic sclerosis is diffuse cutaneous systemic sclerosis.

In certain embodiments, the systemic sclerosis is early diffuse cutaneous systemic sclerosis (i.e., wherein it has been less than 5 years from first non-Raynaud's phenomenon sign or symptom in the subject.)

In certain embodiments, the dosing period is at least 36 weeks, such as at least 37, 38, 39, 40, 41, 42, 43, 44, 45, 46, 47, 48, 49, 50, or 51 weeks. In certain embodiments, the dosing period is at least 1 year (52 weeks), such as at least 2, at least 3, or at least 4 years. In certain embodiments, the compound is administered chronically.

In certain embodiments, Compound I, or a pharmaceutically acceptable salt thereof, is administered orally.

In certain embodiments, 300 mg (on a free acid equivalent weight basis) of Compound I, or a pharmaceutically acceptable salt thereof, is administered twice daily.

In certain embodiments, 300 mg (on a free acid equivalent weight basis) of Compound I, or a pharmaceutically acceptable salt thereof, is administered once daily.

In certain embodiments, treatment with Compound I, or a pharmaceutically acceptable salt thereof, results in an improvement in forced vital capacity (FVC) %.

In certain embodiments, treatment with Compound I, or a pharmaceutically acceptable salt thereof, results in an improvement in HAQ-DI. HAQ-DI is 0-3 scale measuring eight domains of daily functioning (dressing, arising, eating, walking, hygiene, reach, grip, and common daily activities. A score of 3 represents severe disability and a score of 0 represents no disability. A minimum clinically important difference for systemic sclerosis has been suggested to be ≥0.14. See, Sultan et al. (2004) Rheumatology 43:472-8, which is incorporated herein by reference for all purposes.

In certain embodiments, treatment with Compound I, or a pharmaceutically acceptable salt thereof, results in an improvement in MDGA. The Physician Global Assessment (MDGA) is an 11-point Likert scale ranging from 0 to 10 (0=excellent to 10=extremely poor) on which the physician rates the subject's overall health over the past week. There is also a 5-point scale (from 1 to 5; 1=much better to 5=much worse) on which the physician rates the subject's overall scleroderma condition compared to the last clinic visit.

In certain embodiments, treatment with Compound I, or a pharmaceutically acceptable salt thereof, results in an improvement in PTGA. The Physician Global Assessment (PTGA) is an 11-point Likert scale ranging from 0 to 10 (0=excellent to 10=extremely poor) on which the subject rates his/her overall health and illness-related pain level over the past week and how much the skin involvement due to scleroderma has interfered with daily activity and how rapidly the skin disease has been progressing over the past month. There is also a 5-point Likert scale (from 1 to 5; 1=much better to 5=much worse) on which the subject rates overall scleroderma skin involvement compared to the last clinic visit.

In certain embodiments, treatment with Compound I, or a pharmaceutically acceptable salt thereof, results in an improvement in the Physical Effects subscale of the SSPRO-18. The Scleroderma Skin Patient-reported Outcome Instrument (SSPRO-18), developed through concept elicitation in patients with diffuse cutaneous systemic sclerosis (dcSSc) and limited cutaneous systemic sclerosis (lcSSC) based on three focus groups, is an 18-item, patient-reported outcome instrument that specifically assesses skin-related quality of life in patients with systemic sclerosis (SSc). The SSPRO-18 comprises 4 major conceptual constructs—physical effects, emotional effects, physical limitations, and social effects—and has reproducibility and high internal consistency. This instrument reflects how subjects feel and function from several different health perspectives.

In certain embodiments, treatment with Compound I, or a pharmaceutically acceptable salt thereof, results in an improvement in the Physical Limitations subscale of the SSPRO-18.

In certain embodiments, treatment with Compound I, or a pharmaceutically acceptable salt thereof, results in an mRSS decrease of ≥5 points and 25% from Baseline. The Modified Rodnan Skin Score (mRSS) is a validated method for estimating skin thickening. Seventeen different body areas are scored as normal (0), mild thickening (1), moderate thickening (2) and severe thickening (3), with a maximum score of 51.

In certain embodiments, treatment with Compound I, or a pharmaceutically acceptable salt thereof, results in a CRISS score of greater or equal to 0.60. See, Khanna et al. (2016) Arthritis Rheumatol. 68(2):299-311, which is incorporated by reference in its entirety for all purposes. Subjects will be evaluated using the American College of Rheumatology-Composite Response Index in Systemic Sclerosis (CRISS), an outcome measure for dcSSc. The CRISS includes core items that assess change in 2 prominent manifestations of early dcSSc (skin and ILD), functional disability (HAQ-DI) and patient and physician global assessments. In addition, the score captures a clinically meaningful worsening of internal organ involvement requiring treatment.

In certain embodiments, treatment with Compound I, or a pharmaceutically acceptable salt thereof, results in a reduction in skin fibrosis as measured by mRSS change of ≥5.

In certain embodiments, treatment with Compound I, or a pharmaceutically acceptable salt thereof, results in an improvement in HAQ-DI of ≥0.14. In certain embodiments, treatment with Compound I, or a pharmaceutically acceptable salt thereof, results in an improvement in HAQ-DI of about 0.14 and 0.3.

In certain embodiments, treatment with Compound I, or a pharmaceutically acceptable salt thereof, results in an improvement in ≥3 of 5 core measures from Baseline: ≥20% in mRSS, ≥20% in HAQ-DI, ≥20% in PTGA, ≥20% in MDGA and ≥5% for FVC % predicted.

In some embodiments, the severity of idiopathic pulmonary fibrosis is assessed by evaluating symptoms, pulmonary function tests, exercise capacity, lung structure using CT scans and the use of the questionnaires.

Pulmonary Function Tests (PFTs) are an important tool in assessing IPF severity. The easiest test to perform is spirometry and involves a maximal expiration through a mouthpiece followed by a maximal inspiration. The result is the Forced Vital Capacity (FVC). This is the amount of air that is exhaled starting from a maximal inhalation. Results are compared to age, gender and race matched normals. Results are displayed as a volume of air as well as a percent predicted. Normal is about 80% predicted or greater. There are no single agreed upon cut-offs for staging IPF by FVC but many clinicians use the following: mild IPF is about >75% predicted FVC, moderate IPF is about 50-75% predicted FVC, severe IPF is about 25-49% predicted FVC, and very severe IPF is about <25% predicted FVC. More important than the specific value of the FVC is the change in FVC over time. A decline in FVC of >5-10% is associated with an increased risk of death.

In some embodiments, administration of Compound I, or a pharmaceutically acceptable salt thereof, to a human with lung fibrosis increases the FVC of the human. In some embodiments, Compound I, or a pharmaceutically acceptable salt thereof, increases the FVC of a human with lung fibrosis by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, or more than 100%.

Diffusion capacity is another type of pulmonary function test. It is a measure of the way in which gas exchanges across the lungs. The results are reported as percent predicted. Lower values indicate more advanced disease. Values less than 40% are associated with worse survival. Declines in diffusing capacity are also associated with worse outcomes. Diffusing capacity of the lungs for carbon monoxide (DLCO) determines how much oxygen travels from the alveoli of the lungs to the blood stream.

In some embodiments, administration of Compound I, or a pharmaceutically acceptable salt thereof, to a human with lung fibrosis increases the DLCO. In some embodiments, Compound I, or a pharmaceutically acceptable salt thereof, increases the DLCO of a human with lung fibrosis by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, or more than 100%.

The six-minute walk test measures exercise capacity (distance walked, oxygen saturation during exercise and heart rate and blood pressure).

High resolution CT scanning provides an assessment of the structural extent of fibrosis—how much fibrosis is present. More advanced radiographic fibrosis is associated with worse outcomes. Over time, increased extent of fibrosis is also associated with less good outcomes.

Other factors associated with a worse prognosis include advanced age, gender, heavy prior smoking history, being underweight, development of pulmonary hypertension and exacerbations of your underlying disease. IPF patients are also at increased risk for developing lung cancer, which has a powerful impact on prognosis.

Questionnaires are used to measure patient-reported outcome (PRO) assessments, and include: the Living with IPF questionnaire (L-IPF), the King's Brief Interstitial Lung Disease questionnaire (K-BILD), the Leicester Cough Questionnaire (LCQ), and the SF-12 Health Survey (SF-12).

The Living with IPF (L-IPF) is a validated questionnaire that assesses symptoms, disease impacts and health-related quality of life in subjects with IPF. This questionnaire comprises 2 modules: a 15-item symptom module with 3 domains (dyspnea, cough and energy), all with a 24-hour recall, and a 20-item impacts module with 1-week recall. All items in both modules have response options in a 5-point (0-4) numerical rating scale format.

The King's Brief Interstitial Lung Disease Questionnaire (K-BILD) is a self-completed health status questionnaire comprising 15 items and a 7-point Likert response scale that was developed and validated specifically for patients with IPF. This questionnaire has 3 domains: psychological, breathlessness and activities and chest symptoms. The K-BILD domains and total score range from 0 to 100; 100 represents best health status. In some embodiments, administration of Compound I, or a pharmaceutically acceptable salt thereof, to a human with lung fibrosis results in a increase in the K-BILD score. In some embodiments, the K-BILD score increases by at least 1 unit, at least 2 units, at least 3 unit, at least 4 units, at least 5 unit, at least 6 units, at least 7 unit, at least 8 units, at least 9 unit, at least 10 units, at least 11 unit, at least 12 units, or more than 12 units.

The Leicester Cough Questionnaire (LCQ) is a patient-reported questionnaire evaluating the impact of cough on quality of life. The LCQ comprises 19 items and takes 5 to 10 minutes to complete. Each item assesses symptoms or the impact of symptoms over the last 2 weeks on a 7-point Likert scale. Scores in 3 domains (physical, psychological and social) are calculated as a mean for each domain (range: 1 to 7). A total score (range: 3 to 21) is also calculated by summing the domain scores. Higher scores indicate better quality of life. In some embodiments, administration of Compound I, or a pharmaceutically acceptable salt thereof, to a human with lung fibrosis results in a increase in the LCQ score. In some embodiments, the LCQ score increases by at least 1 unit, at least 2 units, at least 3 unit, at least 4 units, at least 5 unit, at least 6 units, at least 7 unit, at least 8 units, at least 9 unit, at least 10 units, at least 11 unit, at least 12 units, or more than 12 units.

The SF-12 Health Survey (SF-12) is a 12-item survey used to assess general health-related quality of life. The SF-12 items are scored to generate a physical component score (PCS) and mental component score (MCS) from the subject's perspective. The SF-12 examines 8 domains of health outcomes, including physical functioning, role-physical, bodily pain, general health, vitality, social functioning, role-emotional and mental health. The SF-12 is a shorter version of the SF-36, which has accepted validity for use in subjects with IPF [Swigris et al., Respir Med. 2010; 104: 296-304; Tomioka et al., Intern Med. 2007; 46:1533-42] and is 1 of 4 questionnaires used in the IPF Prospective Outcomes (IPF-PRO), an ongoing observational US registry of patients with confirmed IPF that records patient-reported outcomes.

In some embodiments, Compound I, or a pharmaceutically acceptable salt thereof, is used to slow the decline in lung function in a human with lung fibrosis. In some embodiments, Compound I, or a pharmaceutically acceptable salt thereof, is used to reduce the frequency of disease exacerbations in a human with lung fibrosis. In some embodiments, Compound I, or a pharmaceutically acceptable salt thereof, is used to improve survival in a human with lung fibrosis. In some embodiments, Compound I, or a pharmaceutically acceptable salt thereof, is used to slow the decline in lung function, reduce the frequency of exacerbations, and improve survival in a human with lung fibrosis.

As the normal lung is replaced by scar tissue, the lung's ability to exchange gas and deliver oxygen into the blood is impaired. If enough of the lung is involved, this can result in low oxygen levels in the blood. This is referred to as hypoxemia or hypoxia. Blood oxygen levels are measured in two ways.

Noninvasive oxygen measurements are made with a pulse oximeter. The pulse oximeter reads a saturation that measures the percentage of hemoglobin that is carrying oxygen. Normal values are between 96-100%.

A more accurate way to measure the amount of oxygen in blood is with an arterial blood gas. This requires sticking a needle into the artery in your wrist and removing a few milliliters of blood. The oxygen tension is then directly measured.

In some embodiments, oxygen is administered to the human when saturations are less than 88-89% either at rest, with activity or when sleeping. Resting oxygen saturations are generally higher than exercise oxygen saturations. Sleeping oxygen saturations are usually in between.

Oxygen is delivered from tanks or concentrators via nasal cannula. Usual flow rates start at 2 liters per minute but may be increased as needed. Advanced delivery systems such as oximizer pendants can improve oxygen delivery for patients that require high flow rates.

Combination Treatments

In certain instances, it is appropriate or beneficial to administer Compound I, or a pharmaceutically acceptable salt thereof, in combination with one or more other therapeutic agents selected from an immunosuppressant (e.g., methotrexate, azathioprine, cyclosporine, mycophenolate mofetil, and cyclophosphamide), T-cell-directed therapy (e.g., halofuginone, basiliximab, alemtuzumab, abatacept, rapamycin), B-cell directed therapy (e.g., rituximab), autologous hematopoietic stem cell transplantation, a chemokine ligand receptor antagonist (e.g., an agent that targets the CXCL12/CSCR4 axis (e.g., AMD3100)), a DNA methylation inhibitor (5-azacytidine), a histone deacetylase inhibitor (e.g., trichostatin A), a statin (e.g., atorvastatin, simvastatin, pravastatin), an endothelin receptor antagonist (e.g., bosentan), a phosphodiesterase type V inhibitor (e.g., sildenafil) a prostacyclin analog (e.g., trepostinil), an inhibitor of cytokine synthesis and/or signaling (e.g., imatinib mesylate, rosiglitazone, rapamycin, anti-transforming growth factor beta 1 (anti-TGFβ1) antibody, mycophenolate mofetil, an anti-IL-6 antibody (e.g., tocilizumab)), corticosteroids, non-steroidal anti-inflammatory drugs, light therapy, and blood pressure medications (e.g., ACE inhibitors).

In some embodiments, gastro-esophageal reflux disease (GERD) plays a role in the development progression of IPF. In some embodiments, acid suppressing therapy is coadministered with Compound I, or a pharmaceutically acceptable salt thereof. Acid suppressing therapy includes, but is not limited to, H2 Blockers (e.g. cimetidine, famotidine, lafutidine, nizatidine, ranitidine, roxatidine, tiotidine) and proton pump inhibitors (e.g. omeprazole).

In some embodiments, a vaccination against pneumonia is coadministered with Compound I, or a pharmaceutically acceptable salt thereof. Suitable vaccines include, but are not limited to, polysaccharide vaccines and conjugated vaccines. The polysaccharide vaccine most commonly used today (PneumoVax) consists of purified polysaccharides from 23 serotypes (1, 2, 3, 4, 5, 6b, 7F, 8,9N, 9V, 10A, 11A, 12F, 14, 15B, 17F, 18C, 19F, 19A, 20, 22F, 23F, and 33F). Conjugated vaccines consist of capsular polysaccharides covalently bound to the diphtheria toxoid CRM197. An example of a conjugated vaccine is Prevnar 13. PneumoVax is given as 2 doses separated by at least 5 years and separated from Prevnar by at least one year. Prevnar is given as a one-time dose.

In some embodiments, pulmonary rehabilitation is performed in combination with the administered of Compound I, or a pharmaceutically acceptable salt thereof. Pulmonary rehabilitation is a structured exercise program that focuses on both aerobic and strength training.

In some embodiments, one or more cough suppression medications are coadministered with Compound I, or a pharmaceutically acceptable salt thereof. Cough can be one of the most vexing symptoms of IPF. Treatments for cough include, but are not limited to, expectorants, antitussives, cough suppressants, antihistamines, decongestants, steroids, benzonatate, honey and sugar syrups.

Expectorants include, but are not limited to, acetylcysteine and guaifenesin.

Antitussives, or cough suppressants, include, but are not limited to, codeine, pholcodine, dextromethorphan, noscapine, and butamirate.

Antihistamines include, but are not limited to, mepyramine (pyrilamine), antazoline, diphenhydramine, carbinoxamine, doxylamine, clemastine, dimenhydrinate, pheniramine, chlorphenamine (chlorpheniramine), dexchlorpheniramine, brompheniramine, triprolidine, cetirizine, cyclizine, chlorcyclizine, hydroxyzine, meclizine, loratadine, desloratidine, promethazine, alimemazine (trimeprazine), cyproheptadine, azatadine, ketotifen, acrivastine, astemizole, cetirizine, mizolastine, terfenadine, azelastine, levocabastine, olopatadine, levocetirizine, fexofenadine.

Decongestants include, but are not limited to, ephedrine.

Steroids, include, but are not limited to, betamethasone, prednisone, alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone/prednisolone, rimexolone, tixocortol, triamcinolone, and ulobetasol.

In some embodiments, honey or sugar syrups soften the coughing.

In yet another embodiment described herein, Compound I, or a pharmaceutically acceptable salt thereof, is coadministered with at least one agent used in the treatment of respiratory conditions. Agents used in the treatment of respiratory conditions include, but are not limited to, bronchodilators (e.g., sympathomimetic agents and xanthine derivatives), leukotriene receptor antagonists, leukotriene formation inhibitors, leukotriene modulators, nasal decongestants, respiratory enzymes, lung surfactants, antihistamines (e.g., mepyramine (pyrilamine), antazoline, diphenhydramine, carbinoxamine, doxylamine, clemastine, dimenhydrinate, pheniramine, chlorphenamine (chlorpheniramine), dexchlorpheniramine, brompheniramine, triprolidine, cetirizine, cyclizine, chlorcyclizine, hydroxyzine, meclizine, loratadine, desloratidine, promethazine, alimemazine (trimeprazine), cyproheptadine, azatadine, ketotifen, acrivastine, astemizole, cetirizine, mizolastine, terfenadine, azelastine, levocabastine, olopatadine, levocetirizine, fexofenadine), mucolytics, corticosteroids, anticholinergics, antitussives, analgesics, expectorants, albuterol, ephedrine, epinephrine, fomoterol, metaproterenol, terbutaline, budesonide, ciclesonide, dexamethasone, flunisolide, fluticasone propionate, triamcinolone acetonide, ipratropium bromide, pseudoephedrine, theophylline, montelukast, zafirlukast, ambrisentan, bosentan, enrasentan, sitaxsentan, tezosentan, iloprost, treprostinil, pirfenidone, nintedanib, and 5-LO inhibitors.

In a specific embodiment described herein, Compound I, or a pharmaceutically acceptable salt thereof, is coadministered with at least one anti-inflammatory agent. In certain embodiments, Compound I, or a pharmaceutically acceptable salt thereof, is coadministered with at least one additional agent selected from, but not limited to, epinephrine, isoproterenol, orciprenaline, bronchodilators, glucocorticoids, leukotriene modifiers, mast-cell stabilizers, xanthines, anticholinergics, β-2 agonists, or 5-LO inhibitors. β-2 agonists include, but are not limited to, short-acting β-2 agonists (e.g., salbutamol (albuterol), levalbuterol, terbutaline, pirbuterol, procaterol, metaproterenol, fenoterol and bitolterol mesylate) and long-acting β-2 agonists (e.g., salmeterol, formoterol, bambuterol and clenbuterol). Glucocorticoids include, but are not limited to, beclometasone, budesonide, ciclesonide, fluticasone and mometasone. Anticholinergics include, but are not limited to, ipratropium and tiotropium. Mast cell stabilizers include, but are not limited to, cromoglicate and nedocromil. Xanthines include, but are not limited to, amminophylline, theobromine and theophylline. Leukotriene antagonists include, but are not limited to, montelukast, tomelukast, pranlukast and zafirlukast. 5-LO inhibitors include, but are not limited to, zileuton.

In one aspect, Compound I, or a pharmaceutically acceptable salt thereof, is coadministered with one or more agents used to treat used to treat asthma, including, but not limited to: combination inhalers (fluticasone and salmeterol oral inhalation (e.g. Advair)); inhaled Beta-2 agonists (albuterol inhaler; albuterol nebulizer solution; formoterol; isoproterenol oral inhalation; levalbuterol; metaproterenol inhalation; pirbuterol acetate oral inhalation; salmeterol aerosol inhalation; salmeterol powder inhalation; terbutaline inhaler);

inhaled corticosteroids (beclomethasone oral inhalation; budesonide inhalation solution; budesonide inhaler; flunisolide oral inhalation; fluticasone inhalation aerosol; fluticasone powder for oral inhalation; mometasone inhalation powder; triamcinolone oral inhalation); leukotriene modifiers (montelukast; zafirlukast; zileuton); mast cell stabilizers (cromolyn inhaler; nedocromil oral inhalation); monoclonal antibodies (omalizumab); oral Beta-2 agonists (albuterol oral syrup; albuterol oral tablets; metaproterenol; terbutaline); bronchodilator (aminophylline; oxtriphylline; theophylline).

In one aspect, Compound I, or a pharmaceutically acceptable salt thereof, is coadministered with one or more agents used to treat chronic obstructive pulmonary disease (COPD), including, but not limited to: anticholinergics (ipratropium bromide oral inhalation); combination Inhalers (albuterol and ipratropium (e.g. Combivent, DuoNeb); fluticasone and salmeterol oral inhalation (e.g. Advair)); corticosteroids (dexamethasone tablets; fludrocortisone acetate; hydrocortisone tablets; methylprednisolone; prednisolone liquid; prednisone oral; triamcinolone oral); inhaled Beta-2 Agonists (albuterol inhaler; albuterol nebulizer solution; formoterol; isoproterenol oral inhalation; levalbuterol; metaproterenol inhalation; pirbuterol acetate oral inhalation; salmeterol aerosol inhalation; salmeterol powder inhalation; terbutaline inhaler); inhaled Corticosteroids (beclomethasone oral inhalation; budesonide inhalation solution; budesonide inhaler; flunisolide oral inhalation; fluticasone inhalation aerosol; fluticasone powder for oral inhalation; triamcinolone oral inhalation); mukolytics (guaifenesin); oral Beta-2 agonists (albuterol oral syrup; albuterol oral tablets; metaproterenol; terbutaline); bronchodilator (aminophylline; oxtriphylline; theophylline).

In some embodiments, Compound I, or a pharmaceutically acceptable salt thereof, is administered in combination with a cough suppression medication, a corticosteroid, an immunosuppressant, N-acetyl cysteine (NAC), an anti-fibrotic therapeutic agent, or combinations thereof. In some embodiments, Compound I, or a pharmaceutically acceptable salt thereof, is administered in combination with N-acetyl cysteine, a corticosteroid, an immunosuppressant, pirfenidone, nintedanib, imatinib, a tyrosine kinase inhibitor, PBI-4050, recombinant pentraxin-2/SAP (PRM-151), aerosol IFN-γ, an inhibitor of CTGF activity, a LPA receptor antagonist, an autotaxin inhibitor, a galectin-3 inhibitor (GB0139, GB1211), a LOXL2 inhibitor (GB2064, PAT1251), tipelukast, an integrin antagonist, a PI3K inhibitor, a JNK inhibitor, a ROCK inhibitor, an anti-IL-13 compound, a CCL2 antagonist, a CCR2 antagonist, an anti-CD20 compound, an anticoagulant, a collagen V treatment, an ASK1 inhibitor, a B-cell activating factor inhibitior (belimumamb), a Rho-associated coiled-cil kinase 2 (Rock2) inhibitor (belumosudil), a NO-independent soluble guanylate cyclase (sGC) activator (riociguat, cinaciguat, vericiguat, ataciguat, nelociguat, lificiguat), a prostanoid (epoprostenol, treprostinil, iloprost), a non-prostanoid prostacyclin (IP) receptor agonist (ralnepag, selexipag), endothelin receptor antagonist (sitaxentan, ambrisentan, macitentan, bosentan), phosphodiesterase type 5 inhibitor (sildenafil, tadalafil), a transforming growth factor beta 1 antagonist, a PDE-4b inhibitor, or combinations thereof.

In one embodiment, Compound I, or a pharmaceutically acceptable salt thereof, is coadministered with inhaled corticosteroids. In some embodiments, low doses of prednisone are coadministered with Compound I, or a pharmaceutically acceptable salt thereof.

In some embodiments, an immunosuppresant is coadministered with Compound I, or a pharmaceutically acceptable salt thereof. Immunosuppresants include, but are not limited to, prednisone and azathioprine.

In some embodiments, N-acetyl cysteine (NAC) is coadministered with Compound I, or a pharmaceutically acceptable salt thereof.

In some embodiments, Compound I, or a pharmaceutically acceptable salt thereof, is used in combination with pirfenidone and/or nintedanib. Additional therapeutic agents are contemplated in combination with Compound I, or a pharmaceutically acceptable salt thereof, include imatinab and other tyrosine kinase inhibitors, PBI-4050, recombinant pentraxin-2/SAP (PRM-151), aerosol IFN-γ, inhibitors of CTGF activity (FG-3019), autotaxin inhibitors (GLPG-1690, PAT-409), galectin-3 inhibitors (TD 139; GB0139; GB1211), LOXL2 Inhibitors (GB2064; PAT1251; PXS-5382), SSAO inhibitos (PXS-4728), Tipelukast (MN-001), integrin antagonists (STX-100/BG00011, GSK3008348), PI3K inhibitirs (GSK2126458), JNK inhibitors (CC-90001), ROCK inhibitors (KD025), anti-IL-13 compounds (Tralokinumab, Lebrikizumab, QAX-576), CCL2 antagonists (CNTO888), CCR2 antagonists (Cenicriviroc), anti-CD20 compounds (Rituximab), anticoagulants (Dabigatran), collagen V treatments (IW001) and ASK1 inhibitors (GS4997).

In some embodiments, Compound I, or a pharmaceutically acceptable salt thereof, is used in combination with imatinib.

In some embodiments, Compound I, or a pharmaceutically acceptable salt thereof, is used in combination with pirfenidone. In some embodiments, pirfenidone is coadminstered with Compound I, or a pharmaceutically acceptable salt thereof, up to a maximum daily dose of 2,403 mg.

In some embodiments, Compound I, or a pharmaceutically acceptable salt thereof, is used in combination with nintedanib. In some embodiments, nintedanib is coadminstered with Compound I, or a pharmaceutically acceptable salt thereof, up to a maximum daily dose of 300 mg.

EXAMPLES

The following examples are provided for illustrative purposes only and not to limit the scope of the claims provided herein.

Example 1: Preparation of 2-(4-methoxy-3-(3-methylphenethoxy)benzamido)-2,3-dihydro-1H-indene-2-carboxylic acid (Compound I)

The preparation of Compound I has been previously described (see, WO 2009/135590, U.S. Pat. Nos. 8,362,073, 8,445,530, 8,802,720, 9,328,071, each of which is incorporated by reference in its entirety)._Previously described preparations of Compound I provided Form 2.

Example 2: Preparation of 2-(4-methoxy-3-(3-methylphenethoxy)benzamido)-2,3-dihydro-1H-indene-2-carboxylic acid (Compound I, Form 1)

Compound I (Form 2) was suspended in THF (a minimal amount of THF was used (5 v/w)) and stirred at about 22° C. for about 5 to about 7 days. The vessel or cake was not washed with any further solvent. Compound I (Form 1) was obtained. Coversion of Form 2 to Form 1 did not occur for about two to four days.

Example 3: Alternative Preparation of 2-(4-methoxy-3-(3-methylphenethoxy)benzamido)-2,3-dihydro-1H-indene-2-carboxylic acid (Compound I, Form 1)

An alternative preparation of Compound I is described here.

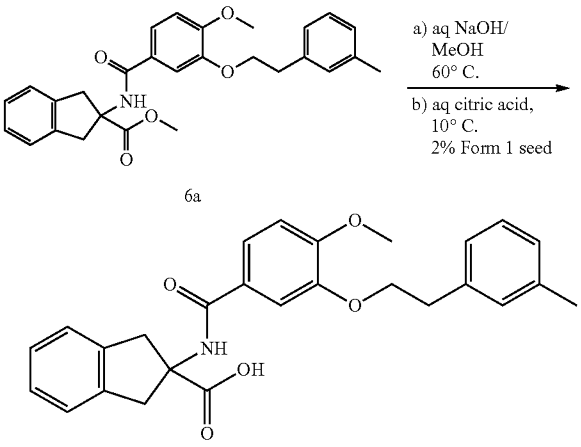

6a

Compound I a) Saponification: Methyl 2-(4-methoxy-3-(3-methylphenethoxy)benzamido)-2,3-dihydro-1H-indene-2-carboxylate (6a, 10 g, 22 mmol, 1 eq) was dissolved in methanol (164 mL, 1.64 vol) and was heated to 50° C. with stirring. Aqueous NaOH (1 M, 26 mL, 1.21 eq) was added to the stirred solution over 30 min followed by water (3 mL, 0.3 vol). The reaction was stirred at 60° C. for 3 h, at which point LCMS showed complete reaction of 6a. The reaction mixture was cooled to 20° C. and filtered to remove insoluble material. The pH of the resultant solution was 13.2.

b) Acidification/Crystallization: The solution was acidified with 1 M citric acid (aq) to pH 7.5. The solution was seeded with crystals of Form 1 (2% by mass), cooled to 10° C. over 3 hrs, and was kept at 10° C. for 1 hr. The resulting suspension was filtered and solids were washed with 1:1 water:methanol (2×5 vol) followed by methanol (2×5 vol). The solid was dried in a vacuum oven at 40° C. to yield Compound I (9.2 g, 95%, Form 1 by XRPD).

Example 4: X-Ray Powder Diffraction (XRPD)

Although the following diffractometers were used, other types of diffractometers could be used. Furthermore, other wavelengths could be used and converted to the Cu Kα. In some embodiments, Synchrotron Radiation X-Ray Powder Diffraction (SR-XRPD) can be used to characterize the crystalline forms.

"Characteristic peaks", to the extent they exist, are a subset of observed peaks and are used to differentiate one crystalline polymorph from another crystalline polymorph (polymorphs being crystalline forms having the same chemical composition). Characteristic peaks are determined by evaluating which observed peaks, if any, are present in one crystalline polymorph of a compound against all other known crystalline polymorphs of that compound to within ±0.2° 2-Theta.

STOE Stadi-P Transmission Diffractometer

X-ray powder diffractions were performed with STOE Stadi-P transmission diffractometers using Cu—$K\alpha_1$ radiation. Linear position sensitive detectors were used for capillary measurements and for samples in flat preparation, while image plate position sensitive detectors (IP-PSDs) were used for temperature-resolved XRPD, humidity-resolved XRPD and for robot samples in 96-well plates. The measured data was visualized and evaluated with the Software WinXPOW V2.12.

The 2-Theta peak values that are provided for the XRPD are within ±0.2° 2-Theta.

Characterization of Solid-State Forms of Compound I

The X-Ray powder diffraction pattern for crystalline Form 1 of Compound I is displayed in FIG. 1. The X-Ray powder diffraction pattern for crystalline Form 2 of Compound I is displayed in FIG. 5. The X-Ray powder diffraction pattern for crystalline Form 3 of Compound I is displayed in FIG. 8. The X-Ray powder diffraction pattern for crystalline Form 4 of Compound I is displayed in FIG. 11.

Characterization of Crystalline Form 1 of Compound I

The X-Ray powder diffraction pattern for crystalline Form 1 of Compound I is displayed in FIG. 1. Characteristic XRPD peaks include: 5.2±0.2° 2-Theta, 9.0±0.2° 2-Theta, 14.4±0.2° 2-Theta, and 17.7±0.2° 2-Theta.

Characterization of Crystalline Form 2 of Compound I

The X-Ray powder diffraction pattern for crystalline Form 2 of Compound I is displayed in FIG. 5. Characteristic XRPD peaks include: 5.6±0.2° 2-Theta, 7.6±0.2° 2-Theta, 8.1±0.2° 2-Theta, 9.4±0.2° 2-Theta, 14.9±0.2° 2-Theta, and 16.3±0.2° 2-Theta.

Characterization of Crystalline Form 3 of Compound I

The X-Ray powder diffraction pattern for crystalline Form 3 of Compound I is displayed in FIG. 8. Characteristic XRPD peaks include: 4.2±0.2° 2-Theta, 6.8±0.2° 2-Theta, 15.1±0.2° 2-Theta, 25.0±0.2° 2-Theta, 25.5±0.2° 2-Theta, and 26.4±0.2° 2-Theta.

In some embodiments, measurements on independently prepared samples on different instruments may lead to variability which is greater than±0.2° 2-Theta. Independently prepared samples of crystalline Forms 1 and 2 were characterized on three additional diffractometers.

Malvern Panalytical Empyrean Diffractometer

Instrument: Malvern Panalytical

Type: Empyrean with a Pixcel 1D Detector, a Copper XRD tube, a theta-theta goniometer and a sample changer.

Characterization of Crystalline Form 1 of Compound I

Figure 15:
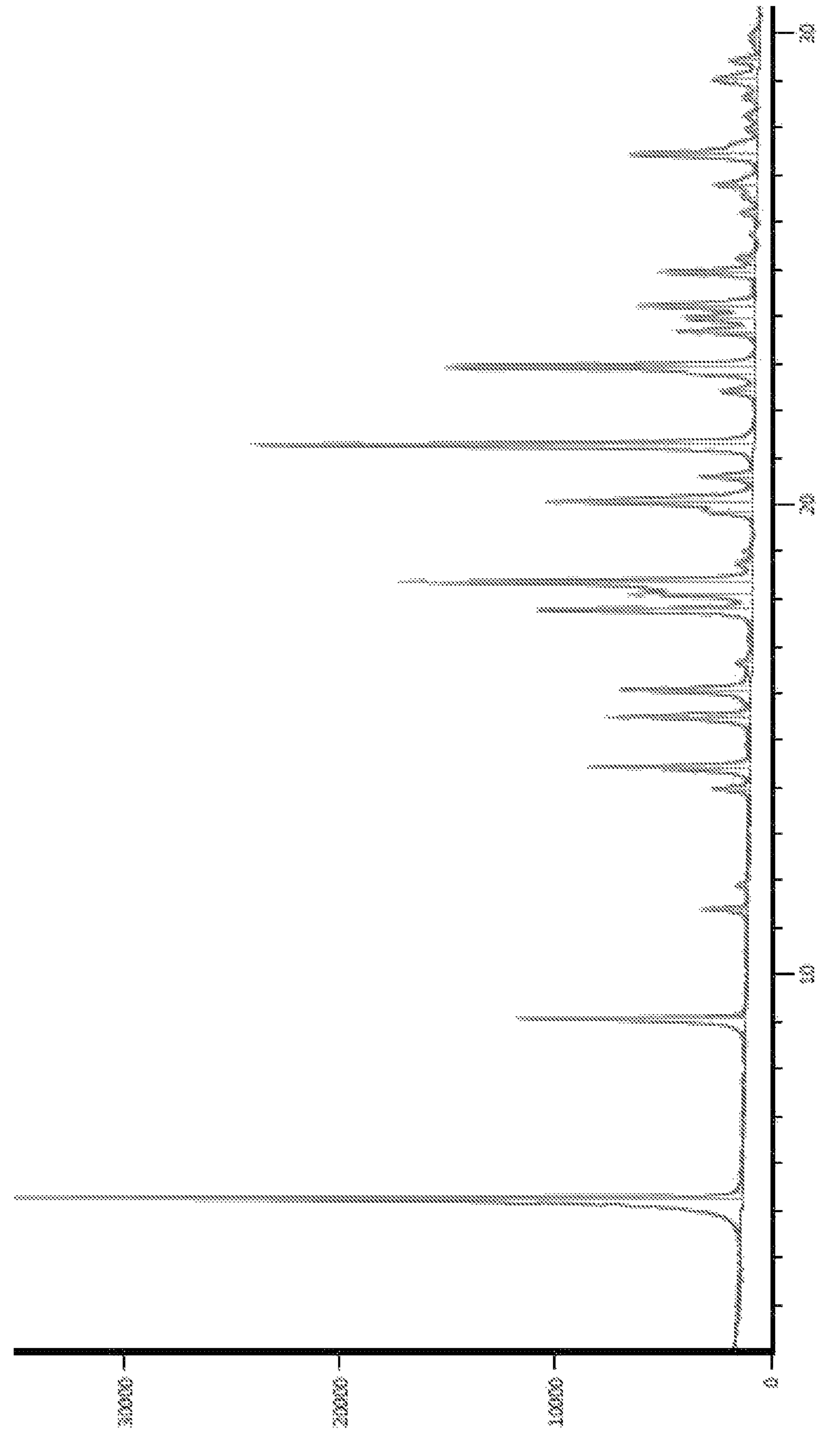
FIG. 15 shows the XRPD pattern of Form 1 obtained with the Malvern Panalytical Empyrean diffractometer.

The X-Ray powder diffraction pattern for crystalline Form 1 of Compound I is displayed in FIG. 15. Characteristic XRPD peaks include: 5.2±0.2° 2-Theta, 9.0±0.2° 2-Theta, 14.4±0.2° 2-Theta, and 17.7±0.2° 2-Theta.

Characterization of Crystalline Form 2 of Compound I

Figure 16:
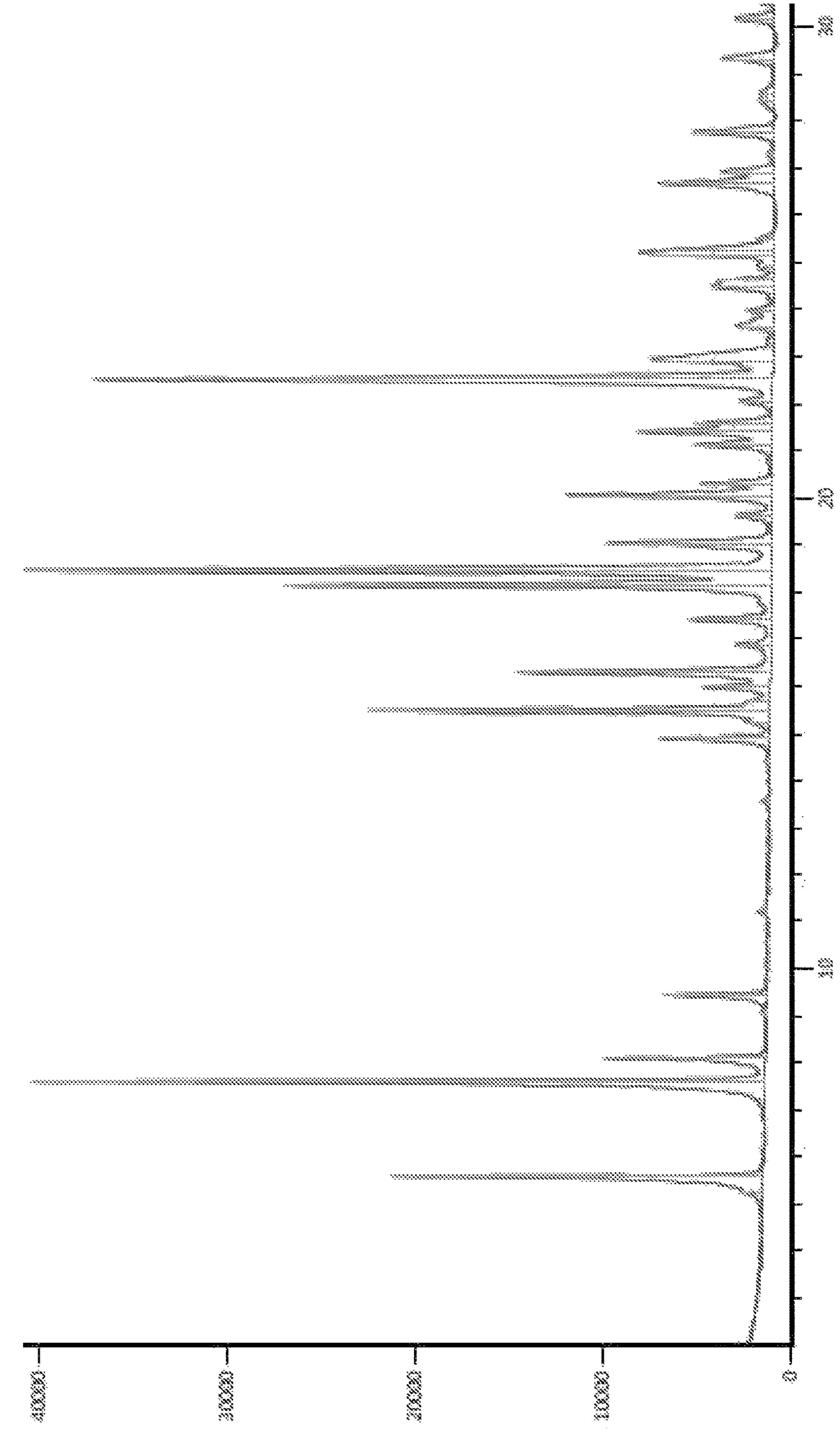
FIG. 16 shows the XRPD pattern of Form 2 obtained with the Malvern Panalytical Empyrean diffractometer.

The X-Ray powder diffraction pattern for crystalline Form 2 of Compound I is displayed in FIG. 16. Characteristic XRPD peaks include: 5.6±0.2° 2-Theta, 7.6±0.2° 2-Theta, 8.1±0.2° 2-Theta, 9.4±0.2° 2-Theta, 14.8±0.2° 2-Theta, and 16.2±0.2° 2-Theta.

Stoe Stadi P, G.52.SYS.S072

Equipment and Measurement Parameters

| | |
|---|---|
| Diffractometer: | Stoe Stadi P, G.52.SYS.S072 |
| Sample holders: | Stoe transmission sample holder, sample between two acetate foils with a 0.4 mm metal washer in between |
| Evaluation software: | WinXPOW by Stoe |

-continued

| The X-ray diffraction pattern was recorded with the following instrumental parameters: | |
|---|---|
| Radiation: | Cu Kα1; 40 kV, 40 mA |
| Collimator: | 0.5 × 10 mm |
| Detector: | Mythen1K |
| Detector distance: | resulting to 0.01°(2θ) intrinsic resolution |
| Monochromator: | Ge, curved monochromator |
| Sample rotation | 1 rps |
| Scan range: | at least 2-40°(2θ) |
| Step size: | 0.020°(2q) |
| Detector Step time: | 48 s |
| Detector step: | 1°(2q) |

Figure 17:
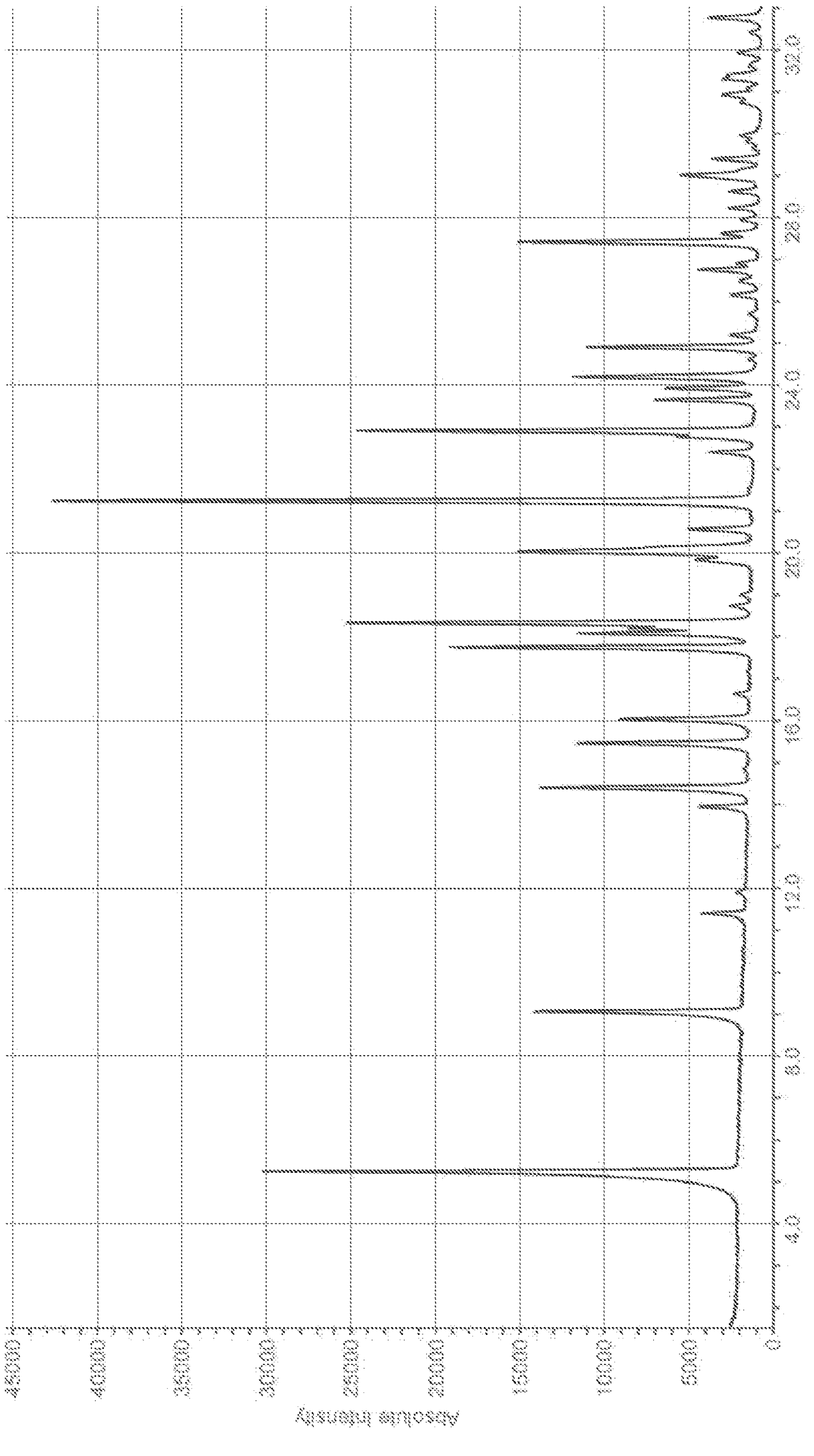
FIG. 17 shows the XRPD pattern of Form 1 obtained with the Stoe Stadi P, G.52.SYS.S072 diffractometer.

Sample preparation: The cylindrical volume determined by the washer and the two sheets of foil was slightly overfilled with a small quantity of the sample and then smoothed with two glass slides to obtain a disk of powder. This specimen was then secured into a Ni-coated metal sample holder Characterization of Crystalline Form 1 of Compound I The X-Ray powder diffraction pattern for crystalline Form 1 of Compound I is displayed in FIG. 17. Characteristic XRPD peaks include: 5.2±0.2° 2-Theta, 9.0±0.2° 2-Theta, 14.4±0.2° 2-Theta, and 17.7±0.2° 2-Theta.

Characterization of Crystalline Form 2 of Compound I

Figure 18:
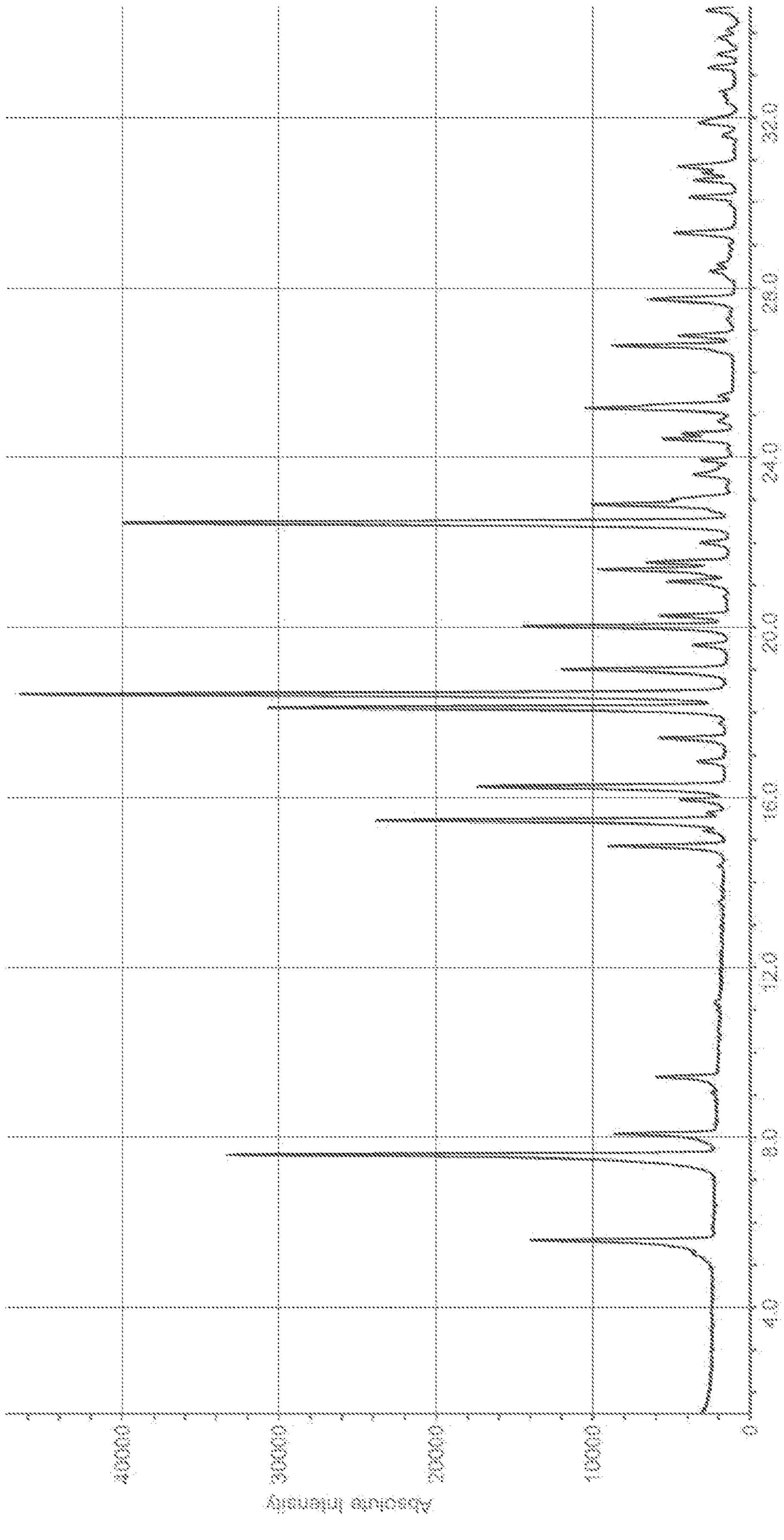
FIG. 18 shows the XRPD pattern of Form 2 obtained with the Stoe Stadi P, G.52.SYS.S072 diffractometer.
Figure 19:
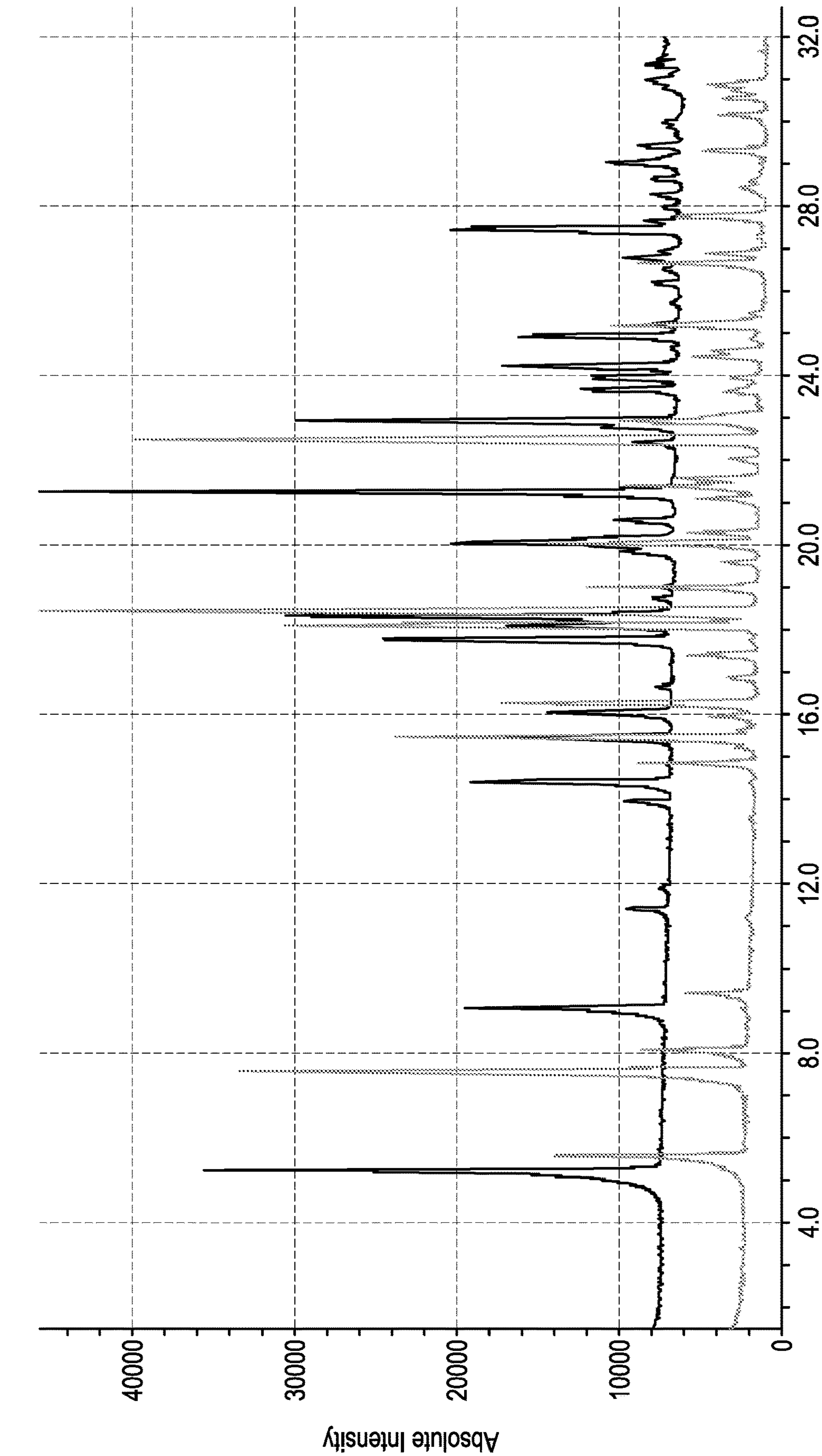
FIG. 19 shows an overlay of the XRPD patterns of Form 1 (top XRPD) Form 2 (bottom XRPD) obtained with the Stoe Stadi P, G.52.SYS.S072 diffractometer.

The X-Ray powder diffraction pattern for crystalline Form 2 of Compound I is displayed in FIG. 18. Characteristic XRPD peaks include: 5.5±0.2° 2-Theta, 7.5±0.2° 2-Theta, 8.0±0.2° 2-Theta, 9.4±0.2° 2-Theta, 14.8±0.2° 2-Theta, and 16.2±0.2° 2-Theta.

Figure 21:
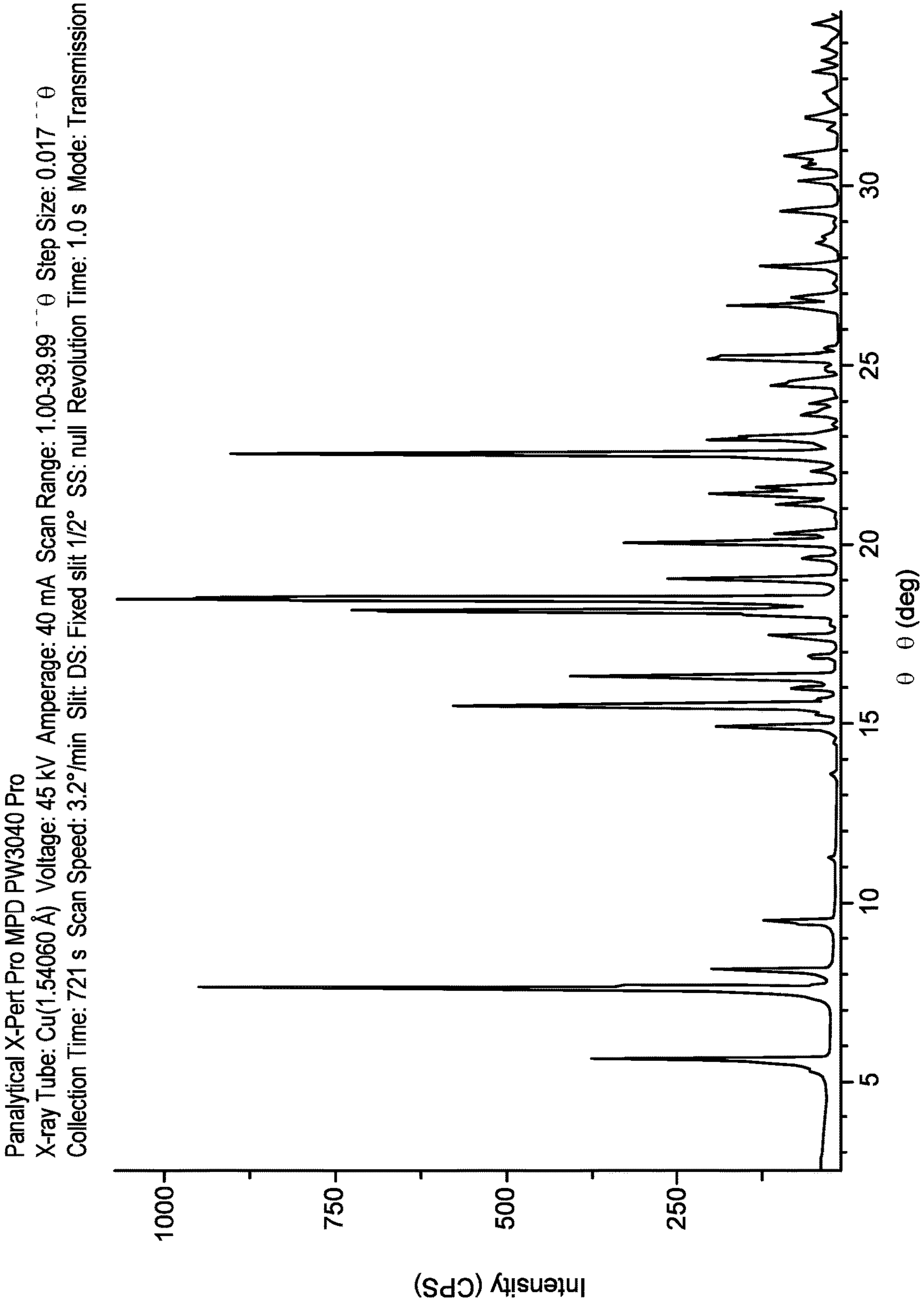
FIG. 21 shows the XRPD pattern of Form 2 obtained with the PANalytical X'Pert PRO MPD diffractometer.

An overlay of the XRPD of Form 1 (top spectra) and Form 2 (bottom spectra) is displayed in FIG. 21.

PANalytical X'Pert PRO MPD Diffractometer

X-Ray Powder Diffractometry (XRPD, transmission mode): XRPD patterns were collected with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. A specimen of the sample was sandwiched between 3-μm-thick films and analyzed in transmission geometry. Prior to the analysis, a silicon specimen (NIST SRM 640f) was analyzed to verify the observed position of the Si 111 peak is consistent with the NIST-certified position. A beam-stop, short antiscatter extension, and antiscatter knife edge were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 5.5.

X-ray Powder Diffraction Peak Identification Process: Rounding algorithms were used to round each peak to the nearest 0.1° or 0.01° 2Θ, depending upon the instrument used to collect the data and/or the inherent peak resolution. The location of the peaks along the x-axis (°2-Theta) in both the figures and the tables were determined using TRIADS® v2.1.1 software and rounded to one or two significant figures after the decimal point based upon the above criteria. Peak position variabilities are given to within±0.2° 2-Theta based upon recommendations outlined in the USP discussion of variability in x-ray powder diffraction (USP-NF 2021, Issue 2, <941>, *Characterization of Crystalline and Partially Crystalline Solids by X-Ray Powder Diffraction* (*XRPD*), 1_GUID-14EBB55E-0D24-45A1-A84F-FE4DCAAEE3E8_1_en-US, official prior to 2013). In some embodiments, measurements on independently prepared samples on different instruments may lead to variability which is greater than ±0.2° 2-Theta. For d-space listings, the wavelength used to calculate d-spacings was 1.5405929 Å, the Cu—Kα1 wavelength (Phys. Rev. A56(6) 4554-4568 (1997)).

Characterization of Crystalline Form 1 of Compound I

Figure 20:
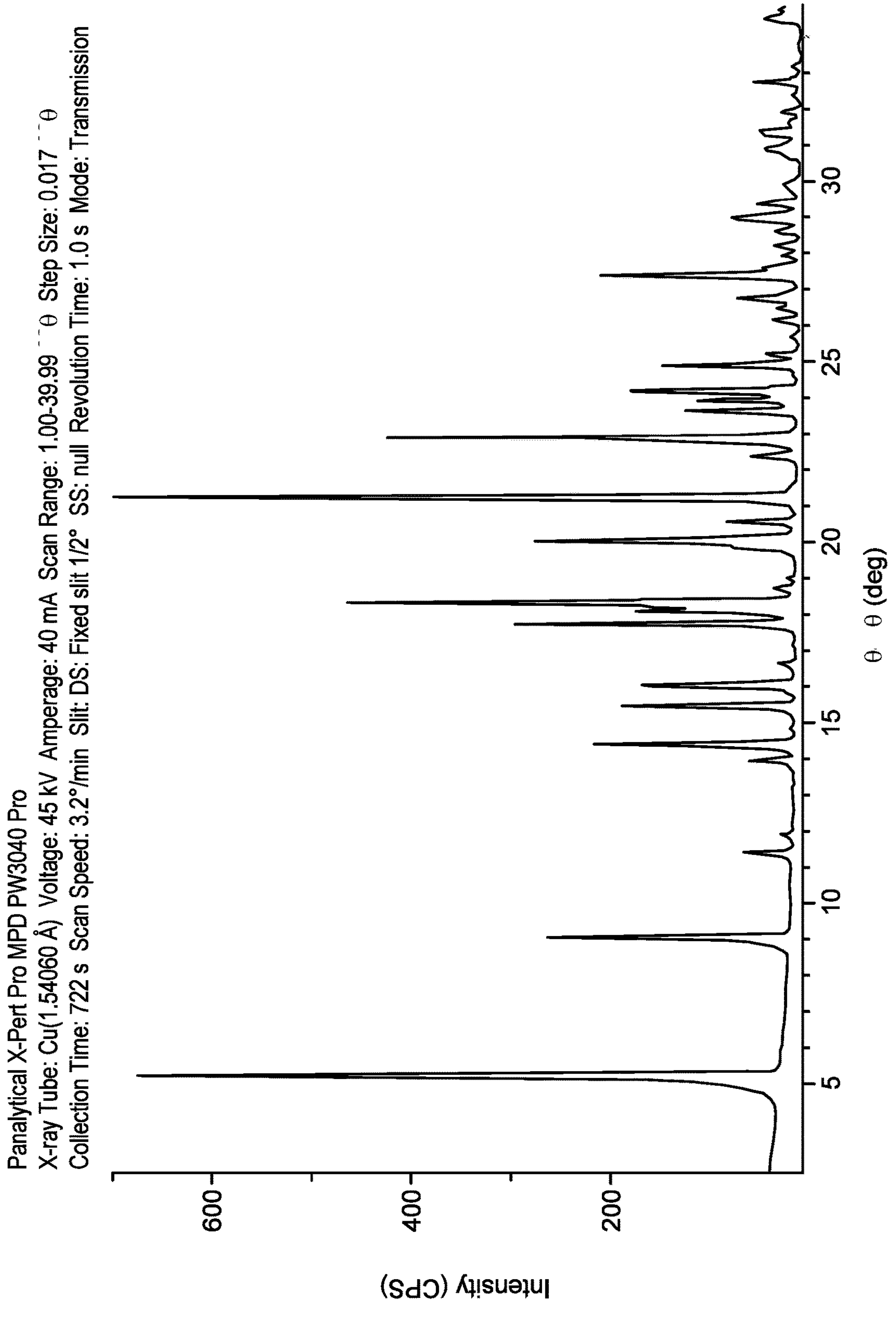
FIG. 20 shows the XRPD pattern of Form 1 obtained with the PANalytical X'Pert PRO MPD diffractometer.

The X-Ray powder diffraction pattern for crystalline Form 1 of Compound I is displayed in FIG. 20. Characteristic XRPD peaks include: 5.2±0.2° 2-Theta, 9.0±0.2° 2-Theta, 14.4±0.2° 2-Theta, and 17.7±0.2° 2-Theta.

Characterization of Crystalline Form 2 of Compound I

The X-Ray powder diffraction pattern for crystalline Form 2 of Compound I is displayed in FIG. 21. Characteristic XRPD peaks include: 5.5±0.2° 2-Theta, 7.5±0.2° 2-Theta, 8.0±0.2° 2-Theta, 9.4±0.2° 2-Theta, 14.8±0.2° 2-Theta, and 16.2±0.2° 2-Theta.

XRPD Limit Test Method with PANalytical X'Pert PRO MPD Diffractometer

Figure 22:
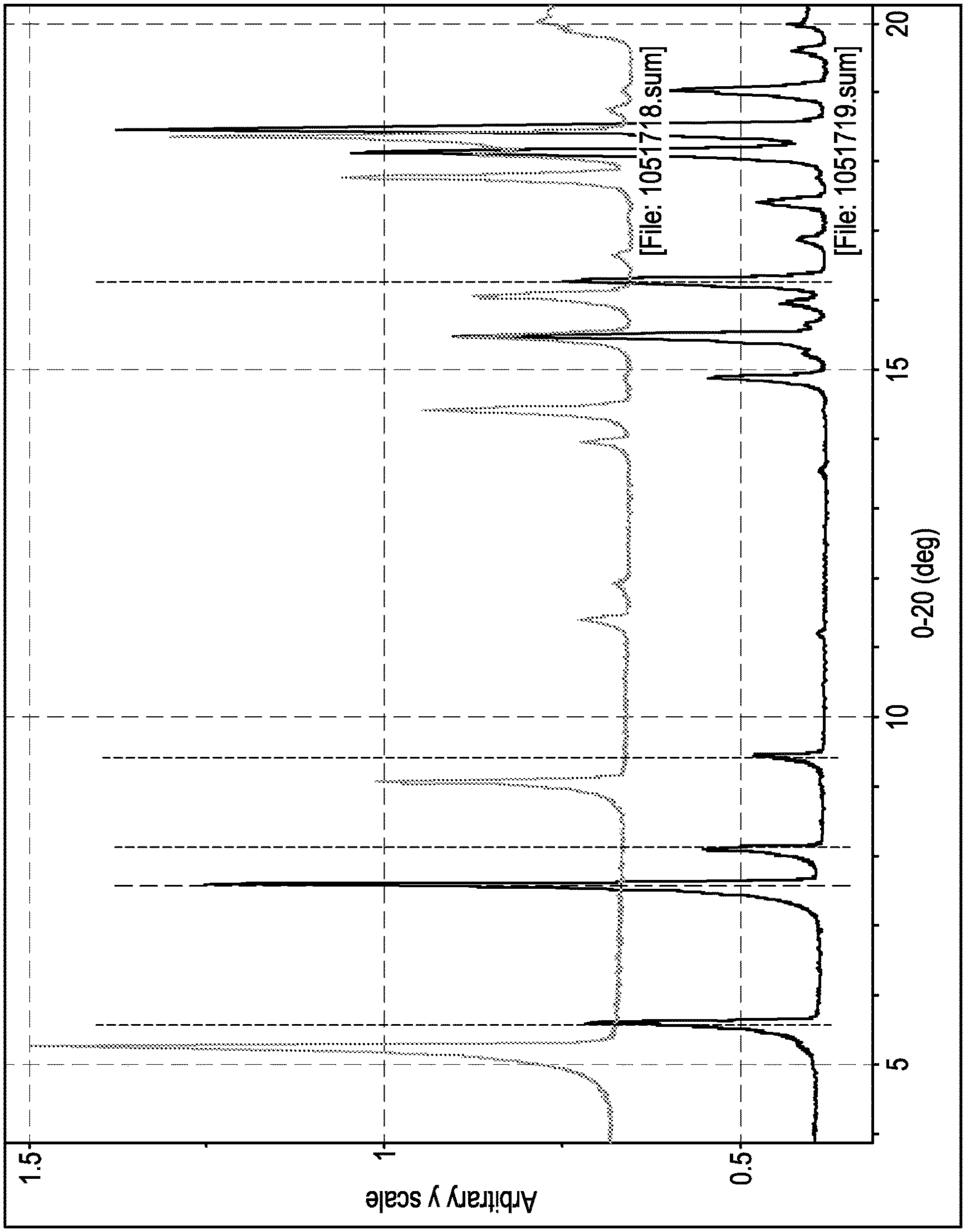
FIG. 22 shows a comparison of XRPD patterns of forms 1 (top XRPD) and 2 (bottom XRPD), highlighting the Form 2 peaks used for the quantification of Form 2 in Form 1.

A non-limiting method development of an XRPD limit test for determining Form 2 in Form 1 drug substance is described. Specificity, the ability to unequivocally assess the analyte in the presence of components that may be expected to be present, was assessed by comparing XRPD patterns of forms 1 and 2. Specificity of Form 2 is good in the Form 1 drug substance as several peaks highlighted in FIG. 22 can be used for the quantification of Form 2 (bottom spectra) in Form 1 (top spectra).

Calibration Models Generation: Calibration standards containing 0-10% Form 2 in Form 1 were prepared by geometrically mixing components without any extra sample handling.

| Form 2 mg | Form 1 mg | Form 2 % | Form 1 % | XRPD |
|---|---|---|---|---|
| 0.0000 | 100.0240 | 0.00 | 100.00 | 1054814 |
| 1.0260 | 98.9810 | 1.03 | 98.97 | 1054212 |
| 1.9830 | 98.0325 | 1.98 | 98.02 | 1054213 |
| 2.9730 | 96.9775 | 2.97 | 97.03 | 1054214 |
| 5.0255 | 94.9725 | 5.03 | 94.97 | 1054215 |
| 6.0170 | 93.9960 | 6.02 | 93.98 | 1054216 |
| 7.9800 | 92.0045 | 7.98 | 92.02 | 1054811 |
| 9.0410 | 90.9795 | 9.04 | 90.96 | 1054812 |
| 9.9990 | 90.0040 | 10.00 | 90.00 | 1054813 |

Figure 23:
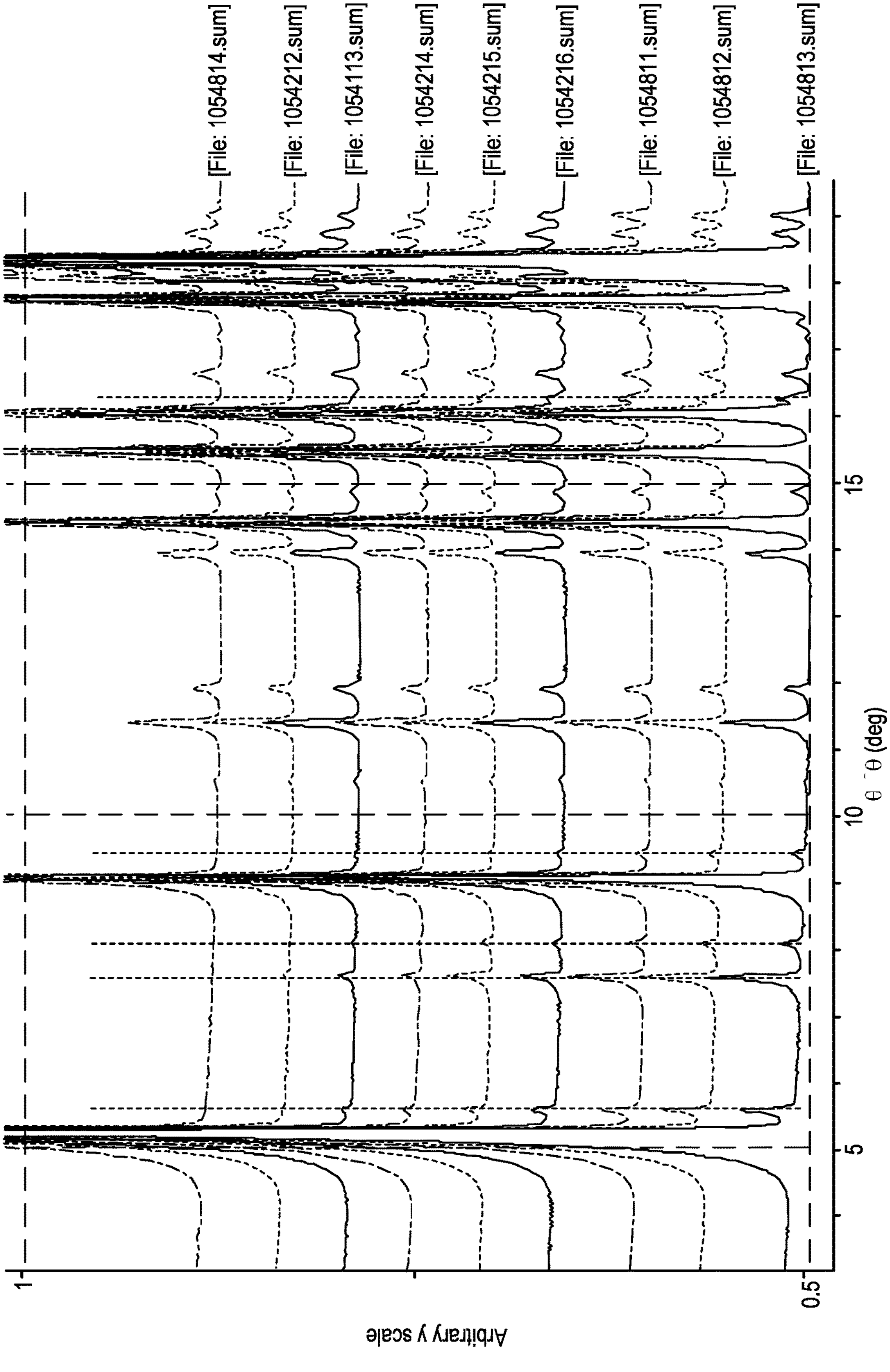
FIG. 23 shows XRPD overlays of the calibration standards used in the development of an XRPD limit test for determining Form 2 in Form 1 drug substance.

XRPD overlays of the calibration standards are shown in FIG. 23. Peaks unique to Form 2 were highlighted (with dotted lines) and showed good linearity based on visual assessment.

A spreadsheet was developed to calculate the areas of peaks approximately at 5.6°, 7.6°, and 8.1° which are normalized to the total peak area in the range of 4.0-25.5°.

Figure 24:
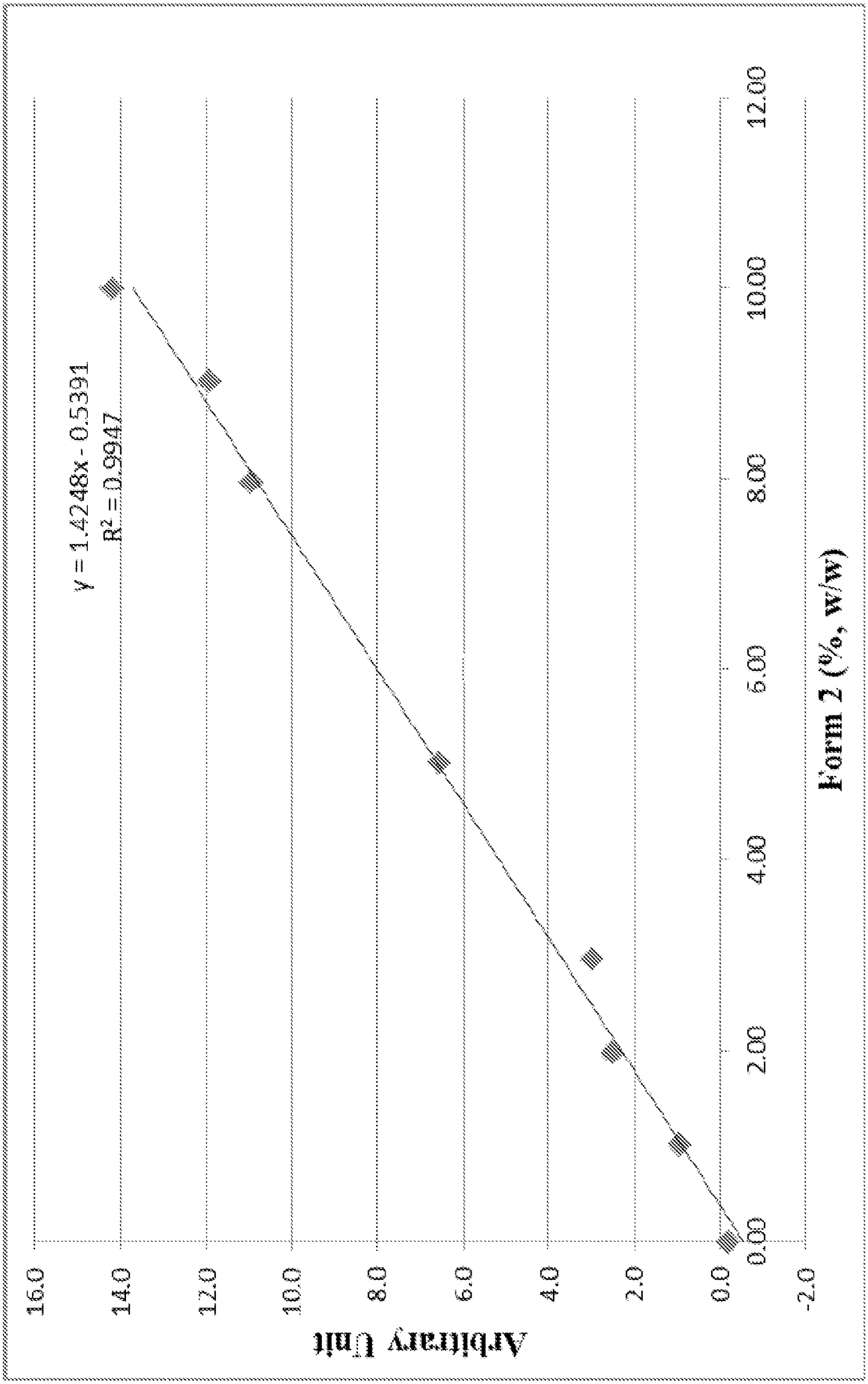
FIG. 24 shows the calibration curve used in the development of an XRPD limit test for determining Form 2 in Form 1 drug substance.

The calibration curve is shown in FIG. 24. Regression statistics along with the limit of detection (LOD) and limit of quantification (LOQ) are summarized below.

| Regression Statistics | |
|---|---|
| Multiple R | 0.9974 |
| R Square | 0.9947 |
| Adjusted R Square | 0.9938 |
| Standard Error | 0.4316 |
| Observations | 8 |

| ANOVA | | | | | |
|---|---|---|---|---|---|
| | df | SS | MS | F | Significance F |
| Regression | 1 | 210.54 | 210.54 | 1130.43 | 4.60825E−08 |
| Residual | 6 | 1.12 | 0.19 | | |
| Total | 7 | 211.66 | | | |

| | Coefficients | Standard Error | t Stat | P-value | Lower 95% | Upper 95% |
|---|---|---|---|---|---|---|
| Intercept | −0.54 | 0.25 | −2.13 | 0.08 | −1.16 | 0.08 |
| X Variable 1 | 1.42 | 0.04 | 33.62 | 4.6082E−08 | 1.32 | 1.53 |

LOD and LOQ were calculated using the following equations:

$$LOD=(3.3\times\sigma)/S$$

$$LOQ=(10\times\sigma)/S$$

where σ is the standard error of linear regression and S is the slope of the calibration curve. The LOD and LOQ were calculated to be 1.0% and 2.8% (w/total), respectively.

Example 5: Differential Scanning calorimetry (DSC)

9.1 Mettler DSC822e

DSC measurements are performed with a Mettler DSC822e (module DSC822e/700/109/414935/0025). 40 μl Al-crucibles with sealed lid and pinhole are used. All measurements are carried out in a nitrogen gas flow of 50 mL/min and typical heating rate of 10° C./min. The measured data is evaluated via the software STARe V8.10.

9.2 Perkin Elmer Diamond DSC

DSC scans were obtained using a Perkin Elmer Diamond DSC. The samples were encapsulated in aluminum pans that were pierced to allow for residual solvent to be released. Scans were obtained at 10° C./min from 25-240° C. The system was calibrated with indium (MP 156.6° C.) and tin (MP 231.9° C.) prior to use.

Characterization of Solid State Forms of Compound I

The DSC thermogram for crystalline Form 1 of Compound I is displayed in FIG. 2.

The DSC thermogram for crystalline Form 2 of Compound I is displayed in FIG. 6.

The DSC thermogram for crystalline Form 3 of Compound I is displayed in FIG. 9.

The DSC thermogram for crystalline Form 4 of Compound I is displayed in FIG. 12.

Differential Scanning calorimetry (DSC) thermogram thermal events for the solid state forms are as described in the following table:

| Solid State Form | DSC Thermal Events |
|---|---|
| Form 1 | three endothermic events having: an onset at about 198.5° C. and a peak at about 200.4° C.; an onset at about 204.8° C. and a peak at about 205.8° C.; and an onset at about 213.9° C. and a peak at about 216.3° C. |
| Form 2 | endothermic event having an onset at about 215.3° C. and a peak at about 216.4° C. |

-continued

| Solid State Form | DSC Thermal Events |
|---|---|
| Form 3 | two endothermic events having: an onset at about 204.2° C. and a peak at about 205.3° C.; and an onset at about 213.6° C. and a peak at about 215.8° C. |

Example 6: Thermogravimetric Analysis (TGA)

Method 10.1: Mettler TGA851e

The thermogravimetric analyses are performed with a Mettler TGA851e (module TGA/SDTA851e/SF1100/042). 100 μl Al-crucibles with sealed lid and hole are used and the measurements are performed in a nitrogen gas flow of 50 mL/min. The measured data is evaluated via the software STARe V8.10.

Method 10.2: Perkin Elmer Pyris System

TGA was obtained on either a Perkin Elmer Pyris System. The samples were run from 25-200° C. at 10° C./min. Accuracy of the system was verified using barium chloride dihydrate.

Characterization of Solid State Forms of Compound I

The TGA pattern for crystalline Form 1 of Compound I is displayed in FIG. 3.

Thermogravimetric Analysis (TGA) patterns for the solid state forms are as described in the following table:

| Solid State Form | TGA Pattern |
|---|---|
| Form 1 | method 10.1: 15.4% w/w loss from about 287.9° C. to about 298.9° C.; method 10.2: TGA pattern (up to 200° C.) showed less than 1% weight loss |
| Form 2 | TGA pattern (up to 200° C.) showed less than 1% weight loss |
| Form 3 | TGA pattern (up to 200° C.) showed less than 1% weight loss |
| Form 4 | TGA pattern (up to 200° C.) showed less than 1% weight loss |

Example 7: Dynamic Vapor Sorption (DVS)

Moisture sorption/desorption isotherms are recorded on a DVS-1 from SURFACE MEASUREMENT SYSTEMS. Two cycles are run at 25° C., in which the Relative Humidity (RH) is stepped from 0 to 95% and back to 0%. The data is evaluated with the software DVSWin V. 2.15.

Reversible water uptake for Form 1 of Compound I as determined by DVS is less than 1% (~−0.1% w/w between 0 and 95% RH).

Example 8: Fourier Transform Infrared (FTIR) Spectroscopy

Nicolet Magna 750 system was used to collect FTIR of the different solid state forms of Compound I. Samples were prepared at 1% concentration in KBr and compressed at 10,000 lbs.

The partial Fourier Transform Infrared (FTIR) pattern overlay for crystalline Forms 1, 2, 3, and 4 of Compound I is displayed in FIG. 13. The FTIR spectrum for Crystalline Form 1 has a peak at about 1739.6 $cm^{-1}$. The FTIR spectrum for Crystalline Form 2 has a peak at about 1731.7 $cm^{-1}$. The FTIR spectrum for Crystalline Form 3 has a peak at about 1722.0 $cm^{-1}$. The FTIR spectrum for Crystalline Form 4 has a peak at about 1743.9 $cm^{-1}$.

Example 9: Fourier Transform Raman Spectroscopy

Raman spectra were acquired on a Raman module interfaced to a Nicolet 6700 IR spectrophotometer (Thermo Nicolet) equipped with an indium gallium arsenide (InGaAs) detector. Wavelength verification was performed using sulfur and cyclohexane. Each sample was prepared for analysis by placing the sample into a 13 mm diameter stainless steel cup and leveling the material. A Thermo Nicolet Step-and-Repeat accessory was used to spin the cup during data acquisition. Three spectra were collected for each sample from outer to inner rings of the sample cup. Approximately 0.5 W of Nd:YVO4 laser power (1064 nm excitation wavelength) was used to irradiate the sample. Each spectrum consists of 512 co-added scans with a spectral resolution of 2 $cm^{-1}$. The three spectra for each sample were averaged using Omnic v7.2 (ThermoElectron).

Raman peak position variabilities are given to within±2 $cm^{-1}$, based on the observed sharpness of the peaks picked and acquisition of data using a 1 $cm^{-1}$ data point spacing (2 $cm^{-1}$ resolution). The peak picking was performed using OMNIC software, version 7.2, Thermo Electron Corporation. Observed Peaks include all Raman peaks for a given form, with the exclusion of very weak intensity peaks and broad peaks with poorly defined maxima.

Figure 25:
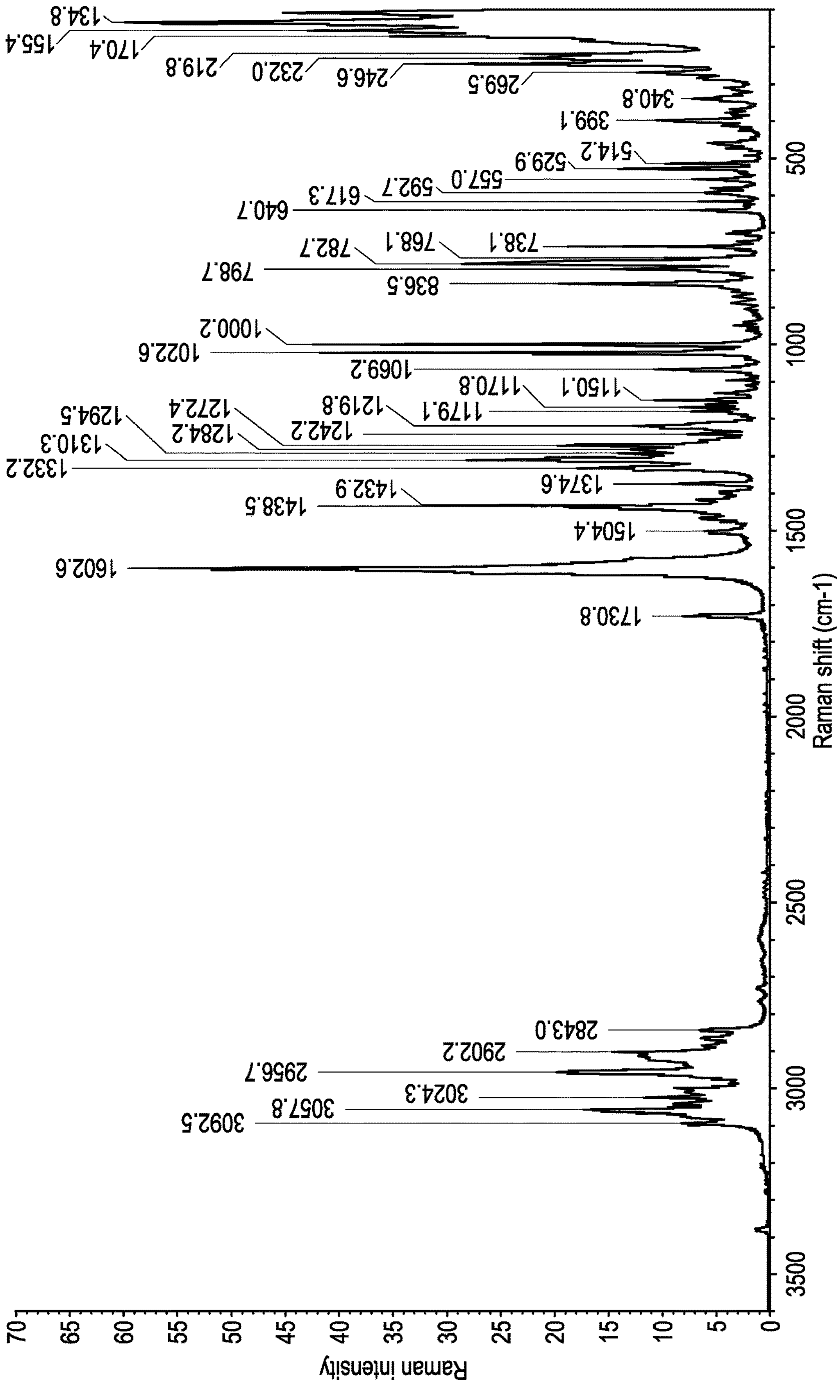
FIG. 25 shows the Raman spectrum for Form 1.

The Raman spectrum for Form 1 is displayed in FIG. 25.

Figure 26:
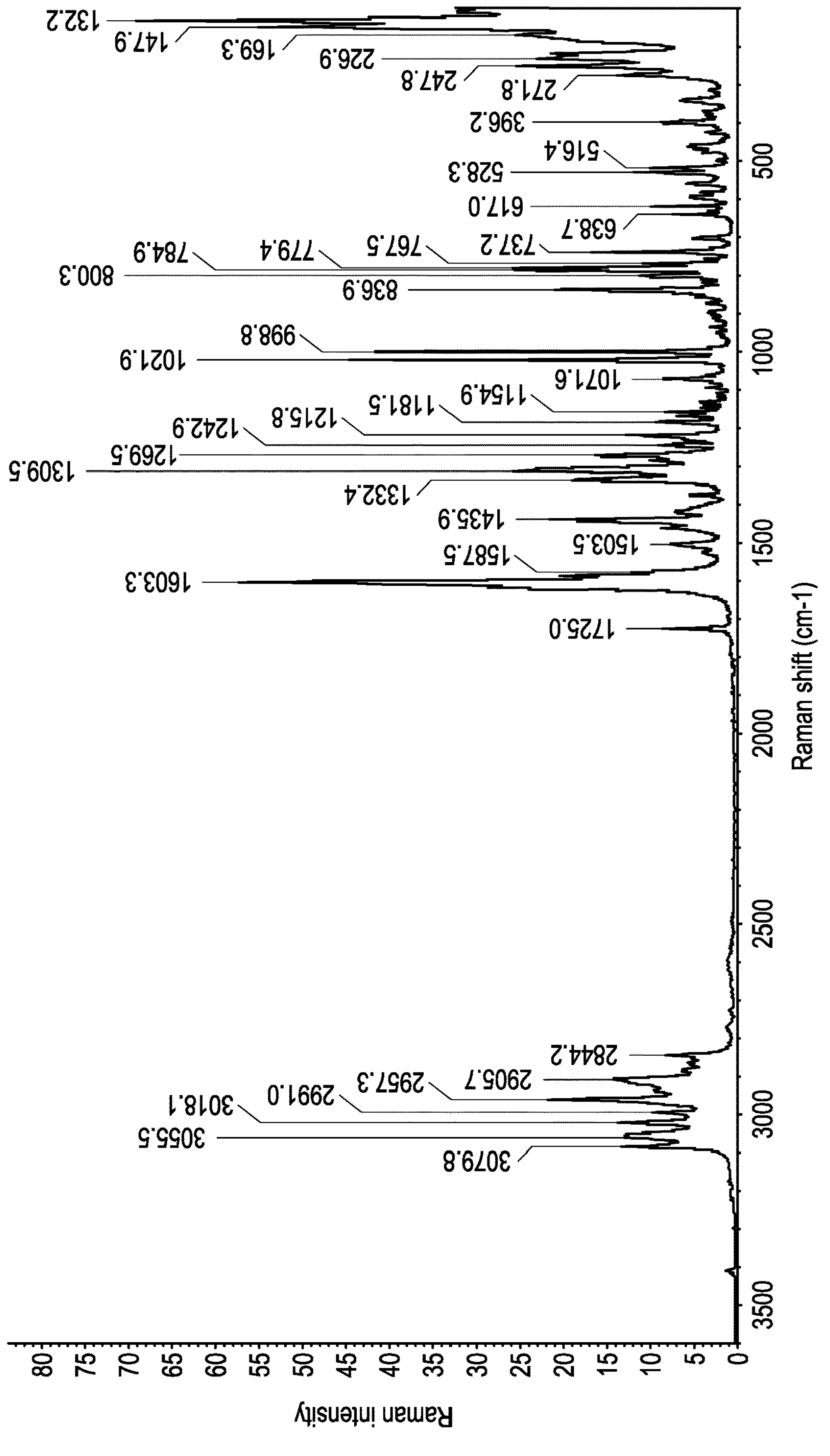
FIG. 26 shows the Raman spectrum for Form 2.

The Raman spectrum for Form 2 is displayed in FIG. 26.

Example 10: Solid State Nuclear Magnetic Resonance (ssNMR) Spectroscopy

All spectra were acquired using a Bruker DRX500 spectrometer, equipped with a 11.7 Tesla magnet and a 4 mm diameter solid-state probe. The following parameters were employed:

| | |
|---|---|
| Observation nucleus | $^{13}C$ |
| Observation frequency | 125.77 MHz |
| Complex data points | 2716 zero-filled to 4096 |
| Spectral width | 34.0 kHz |
| Acquisition time | 40 ms |
| Number of dummy transients | 2 |
| Number of transients | 2048 |
| Relaxation delay | 11.0 s for Form 1 |
| | 20.0 s for Form 2 |
| | 12.0 s for Form 3 |
| | 11.0 s for Amorphous |
| Contact time | 5.0 ms for Form 1 |
| | 3.0 ms for Form 2 |
| | 2.0 ms for Form 3 |
| | 3.0 ms for Amorphous |
| π/2 proton pulse length | 2.9 μs |
| $^{1}H$ decoupling | TPPM-15 |
| Sample rotation rate | 14.0 kHz |
| Temperature | Ambient |

All spectra are referenced indirectly with respect to tetramethylsilane using the high frequency signal of adamantane. All samples were packed into 4 mm OD rotors constructed of zirconia, fitted with a Kel-F drive cap. A Gaussian convolution was applied to the free induction decay prior to Fourier transformation; GB=0.035 and LB=−10.0 Hz.

Characterization of Crystalline Form 1 of Compound I

The ssNMR spectrum for crystalline Form 1 of Compound I is displayed in FIG. 4. Resonances that are characteristic of Form 1 are listed below:

δc/ppm: 23.35, 36.40, 44.12, 45.70, 54.41, 65.40, 71.58, 110.97, 114.45, 121.00, 124.43, 126.78, 127.42, 131.27, 136.47, 138.94, 142.61, 148.68, 152.19, 172.07, 174.59

Characterization of Crystalline Form 2 of Compound I

The ssNMR spectrum for crystalline Form 2 of Compound I is displayed in FIG. 7. Resonances that are characteristic of Form 2 are listed below:

δc/ppm: 20.59, 37.04, 44.03, 46.84, 55.25, 66.34, 71.74, 111.25, 116.90, 122.48, 123.63, 126.39, 128.34, 131.33, 136.78, 137.69, 141.73, 149.44, 153.68, 172.82, 175.49

Characterization of Crystalline Form 3 of Compound I

The ssNMR spectrum for crystalline Form 3 of Compound I is displayed in FIG. 10. Resonances that are characteristic of Form 3 are listed below:

δc/ppm: 21.72#, 22.23#, 43.81, 46.00, 54.01, 64.56, 67.67, 109.22, 110.33, 119.58, 122.99, 126.71, 130.28#, 138.46#, 139.68, 140.34, 143.63, 144.25, 146.87, 150.90, 168.32, 176.47 broadened or split signals whose shape or chemical shift may vary.

Characterization of Amorphous Form of Compound I

The ssNMR spectrum for amorphous form of Compound I is displayed in FIG. 14.

Example 11: Stability of Solid State Forms

The physical stability of Forms 1, 2, and 3 was investigated at 80° C./75% RH in order to determine if interconversion was observed. The samples were examined by FTIR after stressing 1 week in open glass vials.

No changes in the FTIR spectrums were observed for any of the forms, suggesting that these forms are relatively stable in the solid state.

Example 12: Solubility Studies

The solubility of the different polymorphs was determined at pH 7.4 in phosphate buffer at 25° C. Samples were analyzed as a function of time for each form to determine the equilibrium values. The residual solids from each sample were analyzed to verify that the form was unchanged during the experiment. The concentration (mg/mL) versus time data is listed below for each form:

| | 1 hr | 2 hr | 3 hr | 24 hr |
|---|---|---|---|---|
| Form 1 | 0.042 | 0.041 | 0.042 | 0.042 |
| Form 2 | 0.034 | 0.039 | 0.043 | 0.057* |
| Form 3 | 0.083 | 0.093 | 0.095 | 0.097 |
| Form 4 | 0.079 | 0.089 | 0.105 | 0.102 |

*additional time point confirmed equilibrium

The equilibrium solubility values at 24 hours show Forms 3 and 4 to be more than double the solubility for Form 1. The 24 hour result for Form 2 was more than 30% greater than Form 1.

It should be noted that analysis of the residual solids showed no polymorphic conversion during the course of the experiments. The data for Forms 3 and 4 are equivalent within experimental error.

Example 13: Single Crystal X-Ray Diffraction (SCXRD) of Crystalline Form 1 of Compound I Crystallization of Compound I from propyl acetate yielded a crystal—$0.5*0.04*0.02\ mm^3$ in size—which was sealed in a Lindemann-glass capillary. X-ray diffraction data were collected on a Bruker/AXS three circle diffractometer, equipped with a SMART APEX area-detector, a low temperature device (model LT 2) and a molybdenum-$K_\alpha$, rotating anode generator, operated at 50 kV/120 mA and adjusted to a fine-focus of $0.5\times5\ mm^2$. Data frames were collected using the program package SMART V 5.628 (Bruker AXS, 2001), applying ω—scans with step widths of 0.3° and an exposure time of 60 seconds. Data processing with the program SAINT+Release 6.45 (Bruker AXS, 2003) yielded 6452 reflections ($\vartheta_{min}=2.04$, $\vartheta_{max}=28.06$; $-8<h<8$, $-7<k<13$, $-22<l<22$) of which 4753 reflections were unique ($R_{int}=0.0829$, $R_\sigma=0.2353$). Refinement of the cell parameters was performed using 720 reflections. The phase problem was solved with direct methods by the XS module of SHELXTL 6.14 (Bruker AXS, 2000).

The structure was refined by least-squares methods (minimization of $(F_o^2-F_c^2)^2$) using the XL module of SHELXTL 6.14 (Bruker AXS, 2000). The positions of all H atoms were experimentally determined from a difference Fourier synthesis map, $S_{goodness\ of\ fit}=0.780$, $R_{all\ data}=0.2189$ ($R_{obs.\ data}=0.0536$ for 1479 reflections with $|F_{obs}|>4\sigma$, $wR2_{all\ data}=0.1080$, $wR2_{obs.\ data}=0.0759$). The largest unassigned peaks in the difference map correspond to −0.193 versus +0.162 electrons per $Å^3$. The average estimated standard deviation (e.s.d.) of a C—C bond is 0.005 Å, that of an O—C bond 0.004 Å, that of an N—C bond 0.004 Å and that of a C—H bond 0.03 Å. The average e.s.d. of C—C—C bond angles is 0.4 and that of C—C—C—C torsion angles 0.5°.

The crystal structure of Crystalline Form 1 of Compound I was determined at 293 K and a summary of the structural data can be found in Table 1 and Table 2.

TABLE 1

Crystal Data of Compound I (Form 1) at 293K

| | |
|---|---|
| Crystal System | triclinic |
| Space Group | P-1; Z = 2 |
| a (Å) | 6.521(6) |
| b (Å) | 10.548(9) |
| c (Å) | 17.453(15) |
| α (°) | 104.080(16) |
| β (°) | 92.430(16) |
| γ (°) | 101.081(17) |
| V ($Å^3$) | 1137.6(17) |
| Calculated Density ($Mg/m^3$) | 1.301 |
| Unique Reflections | 4753 |
| Model Quality | $R_{obs.\ data}$ = 5.36% |

TABLE 2

Atomic coordinates and equivalent isotropic displacement parameters [Å] for Compound I (Form 1) at 293K

| | x | Y | z | U(eq)* |
|---|---|---|---|---|
| O01 | 0.5030(4) | 0.4696(2) | −0.24147(13) | 0.0519(8) |
| O02 | 0.1244(4) | 0.3734(2) | −0.21202(13) | 0.0517(7) |

TABLE 2-continued

Atomic coordinates and equivalent isotropic displacement parameters [Å] for Compound I (Form 1) at 293K

| | x | Y | z | U(eq)* |
|---|---|---|---|---|
| O03 | 0.8430(4) | 0.7934(2) | 0.03104(13) | 0.0437(7) |
| O04 | 0.8283(4) | 1.0809(2) | 0.02552(15) | 0.0441(7) |
| O05 | 1.0255(4) | 1.1365(3) | 0.14238(14) | 0.0665(9) |
| N01 | 0.5633(5) | 0.8827(3) | 0.06678(19) | 0.0418(9) |
| C01 | 1.0831(7) | 0.5910(4) | −0.3552(2) | 0.0543(12) |
| C02 | 1.2317(7) | 0.6751(5) | −0.3842(3) | 0.0661(14) |
| C03 | 1.1721(8) | 0.7334(5) | −0.4423(3) | 0.0654(15) |
| C04 | 0.9651(7) | 0.7091(4) | −0.4737(2) | 0.0557(12) |
| C05 | 0.9012(14) | 0.7688(9) | −0.5392(4) | 0.092(2) |
| C06 | 0.8190(7) | 0.6242(4) | −0.4438(2) | 0.0516(12) |
| C07 | 0.8725(6) | 0.5657(4) | −0.3858(2) | 0.0435(10) |
| C08 | 0.7044(8) | 0.4798(5) | −0.3518(2) | 0.0552(13) |
| C09 | 0.6788(7) | 0.5492(4) | −0.2681(2) | 0.0478(12) |
| C10 | 0.4477(6) | 0.5258(4) | −0.1675(2) | 0.0403(10) |
| C11 | 0.2397(6) | 0.4736(3) | −0.1521(2) | 0.0438(10) |
| C12 | −0.0778(7) | 0.3071(5) | −0.1940(3) | 0.0548(12) |
| C13 | 0.1733(7) | 0.5270(4) | −0.0805(2) | 0.0531(12) |
| C14 | 0.3017(6) | 0.6301(4) | −0.0243(2) | 0.0515(12) |
| C15 | 0.5061(5) | 0.6793(3) | −0.0386(2) | 0.0379(10) |
| C16 | 0.5770(6) | 0.6257(4) | −0.1102(2) | 0.0400(10) |
| C17 | 0.6506(6) | 0.7874(4) | 0.0212(2) | 0.0388(10) |
| C18 | 0.6849(5) | 0.9914(3) | 0.1310(2) | 0.0361(9) |
| C19 | 0.7593(6) | 0.9353(5) | 0.1986(2) | 0.0432(11) |
| C20 | 0.5965(5) | 0.9512(3) | 0.2570(2) | 0.0402(10) |
| C21 | 0.5709(7) | 0.8992(5) | 0.3221(3) | 0.0529(12) |
| C22 | 0.4184(7) | 0.9324(5) | 0.3719(3) | 0.0613(13) |
| C23 | 0.2946(8) | 1.0159(5) | 0.3560(3) | 0.0607(14) |
| C24 | 0.3156(6) | 1.0695(4) | 0.2899(2) | 0.0468(11) |
| C25 | 0.4722(6) | 1.0356(3) | 0.2408(2) | 0.0378(10) |
| C26 | 0.5351(6) | 1.0837(4) | 0.1691(2) | 0.0405(10) |
| C27 | 0.8654(6) | 1.0758(4) | 0.1007(2) | 0.0429(10) |
| H1 | 0.448(4) | 0.886(3) | 0.0505(17) | 0.025(11) |
| H4 | 0.953(7) | 1.131(4) | 0.016(2) | 0.112(18) |
| H01 | 1.122(4) | 0.543(3) | −0.3064(17) | 0.050(10) |
| H02 | 1.390(6) | 0.700(3) | −0.357(2) | 0.089(14) |
| H03 | 1.276(5) | 0.791(3) | −0.4616(18) | 0.061(12) |
| H051 | 0.924(8) | 0.726(5) | −0.582(3) | 0.12(3) |
| H052 | 0.999(10) | 0.857(6) | −0.534(4) | 0.24(4) |
| H053 | 0.776(7) | 0.777(5) | −0.536(3) | 0.13(3) |
| H06 | 0.680(5) | 0.607(3) | −0.4665(17) | 0.041(11) |
| H081 | 0.745(5) | 0.392(3) | −0.3537(19) | 0.062(14) |
| H082 | 0.571(5) | 0.446(3) | −0.3879(18) | 0.064(12) |
| H091 | 0.647(5) | 0.645(3) | −0.2638(17) | 0.052(12) |
| H092 | 0.815(5) | 0.570(3) | −0.2255(19) | 0.073(12) |
| H121 | −0.175(6) | 0.376(4) | −0.183(2) | 0.086(15) |
| H122 | −0.130(5) | 0.245(3) | −0.244(2) | 0.079(14) |
| H123 | −0.054(6) | 0.267(4) | −0.136(3) | 0.131(18) |
| H13 | 0.035(5) | 0.500(3) | −0.073(2) | 0.076(14) |
| H14 | 0.256(4) | 0.664(3) | 0.0241(17) | 0.044(11) |
| H16 | 0.716(4) | 0.667(2) | −0.1171(14) | 0.025(9) |
| H191 | 0.750(4) | 0.844(3) | 0.1739(17) | 0.041(11) |
| H192 | 0.902(5) | 0.999(3) | 0.2276(15) | 0.043(9) |
| H21 | 0.651(5) | 0.842(3) | 0.3281(19) | 0.047(13) |
| H22 | 0.399(5) | 0.900(3) | 0.426(2) | 0.085(13) |
| H23 | 0.181(6) | 1.031(4) | 0.385(2) | 0.082(15) |
| H24 | 0.227(5) | 1.130(3) | 0.2714(17) | 0.047(11) |
| H261 | 0.611(5) | 1.188(3) | 0.1875(16) | 0.051(10) |
| H262 | 0.427(5) | 1.084(3) | 0.1328(17) | 0.051(12) |

*U(eq) is defined as one third of the trace of the orthogonalized Uij tensor.

Example 14: Single Crystal X-Ray Diffraction (SCXRD) of Crystalline Form 2 of Compound I Crystallization of Compound I from N-methyl-2-pyrrolidone/methanol yielded a crystal—$0.6*0.2*0.2\ mm^3$ in size—which was sealed in a Lindemann-glass capillary. X-ray diffraction data were collected on a Bruker/AXS three circle diffractometer, equipped with a SMART APEX area-detector, a low temperature device (model LT 2) and a copper-$K_\alpha$ microfocus generator, operated at 45 kV/650 μA and a focusing beam Montel multilayer optic with an image focus spot diameter of ~250 μm (Wiesmann et al., 2007).

Data frames were collected using the program package SMART V 5.628 (Bruker AXS, 2001), applying ω—scans with step widths of 0.3° and an exposure time of 5 seconds. Data processing with the program SAINT+Release 6.45 (Bruker AXS, 2003) yielded 23571 reflections ($\vartheta_{min}$=2.80, $\vartheta_{max}$=69.16; $-7<h<6$, $-28<k<26$, $-34<l<38$) of which 4163 reflections were unique ($R_{int}$=0.0242, $R_{\sigma}$=0.0190). Refinement of the cell parameters was performed using the 99 local cell parameter determinations observed during data integration. An empirical absorption correction has been applied using the program SADABS, a module of SAINT 6.45 (Bruker AXS, 2003). The phase problem was solved with direct methods by the XS module of SHELXTL 6.14 (Bruker AXS, 2000).

The structure was refined by least-squares methods (minimization of $(F_o^2-F_c^2)^2$) using the XL module of SHELXTL 6.14 (Bruker AXS, 2000). The positions of all H atoms were experimentally determined from a difference Fourier synthesis map, $S_{goodness\ of\ fit}$=1.039, $R_{all\ data}$=0.0490 ($R_{obs.\ data}$=0.0379 for 3283 reflections with $|F_{obs}|>4\sigma$, $wR2_{all\ data}$=0.1041, $wR2_{obs.\ data}$=0.0971). The largest unassigned peaks in the difference map correspond to −0.179 versus +0.185 electrons per $Å^3$. The average estimated standard deviation (e.s.d.) of a C—C bond is 0.002 Å, that of an O—C bond 0.002 Å, that of an N—C bond 0.002 Å and that of a C—H bond 0.02 Å. The average e.s.d. of C—C—C bond angles is 0.2 and that of C—C—C—C torsion angles 0.2°.

The crystal structure of Crystalline Form 2 of Compound I was determined at 293 K and a summary of the structural data can be found in Table 3 and Table 4.

TABLE 3

Crystal Data of Compound I (Form 2) at 293K

| | |
|---|---|
| Crystal System | orthorhombic |
| Space Group | Pbca; Z = 8 |
| a (Å) | 6.2823(10) |
| b (Å) | 23.285(4) |
| c (Å) | 31.614(6) |
| α (°) | 90.00° |
| β (°) | 90.00° |
| γ (°) | 90.00° |
| V ($Å^3$) | 4624.5(14) |
| Calculated Density ($Mg/m^3$) | 1.280 |
| Unique Reflections | 4163 |
| Model Quality | $R_{obs.\ data}$ = 3.79% |

TABLE 4

Atomic coordinates and equivalent isotropic displacement parameters [Å] for Compound I (Form 2) at 293K

| | x | Y | z | U(eq)* |
|---|---|---|---|---|
| O01 | 0.64153(19) | 0.50661(5) | 0.1851(3) | 0.0611(3) |
| O02 | 0.28437(18) | 0.45533(5) | 0.19955(3) | 0.0633(3) |
| O03 | 0.90062(15) | 0.41927(4) | 0.04333(3) | 0.0463(3) |
| O04 | 0.80055(16) | 0.50310(4) | −0.02774(3) | 0.0502(3) |
| O05 | 0.9886(2) | 0.44424(5) | −0.06867(4) | 0.0775(4) |
| N01 | 0.5874(2) | 0.41538(5) | 0.00862(4) | 0.0430(3) |
| C01 | 1.1636(3) | 0.63689(10) | 0.18246(6) | 0.0685(5) |
| C02 | 1.2638(4) | 0.68761(11) | 0.17096(6) | 0.0805(6) |
| C03 | 1.1664(4) | 0.73952(10) | 0.17789(6) | 0.0800(6) |
| C04 | 0.9689(3) | 0.74237(8) | 0.19659(6) | 0.0720(5) |
| C05 | 0.8583(8) | 0.79928(13) | 0.20384(14) | 0.1180(11) |
| C06 | 0.8710(3) | 0.69112(8) | 0.20812(5) | 0.0636(5) |
| C07 | 0.9644(3) | 0.63853(7) | 0.20097(5) | 0.0578(4) |
| C08 | 0.8452(4) | 0.58411(10) | 0.21203(6) | 0.0732(6) |
| C09 | 0.7850(3) | 0.55127(9) | 0.17367(5) | 0.0629(5) |
| C10 | 0.5684(2) | 0.47210(6) | 0.15318(4) | 0.0460(3) |

TABLE 4-continued

Atomic coordinates and equivalent isotropic displacement parameters [Å] for Compound I (Form 2) at 293K

| | x | Y | z | U(eq)* |
|---|---|---|---|---|
| C11 | 0.3731(2) | 0.44413(6) | 0.16110(4) | 0.0472(4) |
| C12 | 0.1001(3) | 0.42334(10) | 0.21130(7) | 0.0692(5) |
| C13 | 0.2878(3) | 0.40883(7) | 0.13037(5) | 0.0517(4) |
| C14 | 0.3910(2) | 0.40118(7) | 0.09210(5) | 0.0493(4) |
| C15 | 0.5845(2) | 0.42789(6) | 0.08447(4) | 0.0416(3) |
| C16 | 0.6729(2) | 0.46302(6) | 0.11559(4) | 0.0444(3) |
| C17 | 0.7039(2) | 0.42086(5) | 0.04418(4) | 0.0404(3) |
| C18 | 0.6857(2) | 0.40508(6) | −0.03269(4) | 0.0422(3) |
| C19 | 0.7875(3) | 0.34474(7) | −0.03372(5) | 0.0502(4) |
| C20 | 0.6175(2) | 0.30717(6) | −0.05197(4) | 0.0481(4) |
| C21 | 0.6098(4) | 0.24762(8) | −0.05344(6) | 0.0662(5) |
| C22 | 0.4395(4) | 0.22158(9) | −0.07369(6) | 0.0783(6) |
| C23 | 0.2804(4) | 0.25389(9) | −0.09190(6) | 0.0736(6) |
| C24 | 0.2872(3) | 0.31333(8) | −0.09077(5) | 0.0579(4) |
| C25 | 0.4573(2) | 0.33957(6) | −0.07050(4) | 0.0459(3) |
| C26 | 0.5073(3) | 0.40272(7) | −0.06663(5) | 0.0471(4) |
| C27 | 0.8436(2) | 0.45215(6) | −0.04449(5) | 0.0479(4) |
| H1 | 0.453(3) | 0.4252(7) | 0.0094(5) | 0.054(5) |
| H4 | 0.906(3) | 0.5274(9) | −0.0346(6) | 0.087(6) |
| H01 | 1.231(3) | 0.5999(10) | 0.1763(6) | 0.084(6) |
| H02 | 1.396(4) | 0.6848(9) | 0.1581(7) | 0.097(7) |
| H03 | 1.243(4) | 0.7768(10) | 0.1684(6) | 0.100(7) |
| H051 | 0.899(7) | 0.8235(19) | 0.1837(13) | 0.20(2) |
| H052 | 0.835(7) | 0.8063(18) | 0.2320(14) | 0.208(19) |
| H053 | 0.704(11) | 0.798(2) | 0.1966(18) | 0.28(3) |
| H06 | 0.731(3) | 0.6930(8) | 0.2207(6) | 0.076(6) |
| H081 | 0.719(4) | 0.5932(11) | 0.2274(8) | 0.121(9) |
| H082 | 0.919(3) | 0.5607(10) | 0.2329(7) | 0.096(7) |
| H091 | 0.733(3) | 0.5726(9) | 0.1502(7) | 0.086(6) |
| H092 | 0.923(4) | 0.5349(9) | 0.1618(7) | 0.103(7) |
| H121 | −0.019(4) | 0.4312(9) | 0.1902(7) | 0.092(7) |
| H122 | 0.063(3) | 0.4362(9) | 0.2379(7) | 0.092(7) |
| H123 | 0.136(3) | 0.3791(10) | 0.2109(6) | 0.090(6) |
| H13 | 0.158(3) | 0.3900(7) | 0.1360(5) | 0.059(5) |
| H14 | 0.332(3) | 0.3756(7) | 0.0716(5) | 0.054(4) |
| H16 | 0.803(2) | 0.4808(6) | 0.1100(4) | 0.046(4) |
| H191 | 0.835(3) | 0.3324(7) | −0.0053(5) | 0.060(5) |
| H192 | 0.912(3) | 0.3445(7) | −0.0524(5) | 0.065(5) |
| H21 | 0.717(3) | 0.2274(8) | −0.0407(6) | 0.072(6) |
| H22 | 0.433(3) | 0.1802(9) | −0.0748(6) | 0.083(6) |
| H23 | 0.157(3) | 0.2352(9) | −0.1048(6) | 0.090(6) |
| H24 | 0.174(3) | 0.3357(8) | −0.1036(6) | 0.070(5) |
| H261 | 0.566(2) | 0.4176(6) | −0.0943(5) | 0.058(4) |
| H262 | 0.385(3) | 0.4262(7) | −0.0586(5) | 0.053(4) |

*U(eq) is defined as one third of the trace of the orthogonalized Uij tensor

The experimentally determined powder diffraction pattern agrees with the one calculated from the crystal structure.

Example A-1: Tablet Formulations

Film-coated tablets containing 10 mg, 100 mg, 150 mg or 200 mg of Compound I and the following excipients: mannitol, microcrystalline cellulose, crospovidone, hypromellose, magnesium stearate, povidone, macrogol, titanium dioxide, sodium laurylsulfate, and docusate sodium were prepared.

Example B-1: Anti-Fibrotic Effects of Compound I

The activity of Compound I, a selective LPAR1 receptor antagonist, was evaluated in dermal fibroblasts from patients with systemic sclerosis and in several models of skin, kidney and heart fibrosis.

Two models of skin fibrosis were used to evaluate the effect of Compound I in comparison with imatinib mesylate, used as a reference. In the model of bleomycin-induced skin fibrosis, using a therapeutic protocol, Compound I at 50 mg/kg/day was able to reverse dermal thickness, myofibroblast differentiation and collagen content in mouse skin. The effect on these markers was comparable with the effects of imatinib. In tight skin (Tsk-1) mice which are heterozygous for a mutation in the fibrillin gene leading to overproduction of matrix proteins in the absence of inflammatory infiltrates, Compound I at 30 mg/kg/day was also able to inhibit the progression of skin fibrosis at a similar level than imatinib.

In addition to its effect on skin fibrosis, Compound I also improved kidney function in models of hypertension-induced or nephrotoxicity-induced renal failure, showed beneficial effect on cardiac function and structure in different models of hypertension or diabetes-related cardiac hypertrophy, fibrosis and heart failure. In parallel, Compound I showed moderate but significant antithrombotic activity in acute models of coagulation and arterial thrombosis. All these pathological events can be observed in SSc patients at different levels and further support the use of Compound I in these patients.

Finally, Compound I has a significant inhibitory effect on the accumulation of leukocytes and total inflammatory cells in broncho-alveolar lavage of presensitized mice treated with ovalbumin.

In conclusion, Compound I inhibits fibrosis in different organs (skin, kidney, and heart). It improves cardiac systolic and diastolic function and has positive effect on arterial stiffness at mostly unchanged blood pressure and demonstrated antithrombotic activity in two models of thrombosis in rats and in one model in mouse. In addition, Compound I reduces inflammation on a model of lung injury exhibiting a predominant Th2-type response.

Example B-2: 8-Week Double-Blind, Randomized, Placebo-Controlled Study Diffuse in Patients with Cutaneous Systemic Sclerosis (dcSSc)

An 8-week double-blind, randomized, placebo-controlled study followed by a 16-week open-label extension with Compound I was performed in patients with early dcSSc who had a baseline modified Rodnan skin thickness score (mRSS) of at least 15. The primary end point was safety during the double-blind phase of the trial. Exploratory end points included the identification of an LPA-induced gene signature in patients' skin.

Seventeen of 32 patients were randomly assigned to receive placebo and 15 to receive Compound I. Thirty patients participated in the open-label extension study. The most frequent adverse events reported for Compound I during the blinded phase were headache, diarrhea, nausea, and falling, and the safety profile was acceptable during the open-label extension. At week 8, the reduction in MRSS was numerically greater in the Compound I group than in the placebo group (mean±SD change −3.57±4.18 versus −2.76±4.85; treatment effect −1.2 [95% confidence interval −4.37, 2.02]). A greater reduction of LPA-related genes was observed in skin samples from the Compound I group at week 8, indicating $LPA_1$ target engagement.

Clinical outcomes from the 16-week open label extension study are provided below.

| | Median Decrease in mRSS | Responder Rate |
|---|---|---|
| 24-weeks of continuous treatment | −7.5 | 78.6% |
| Subjects switched from placebo to Compound I | −7.0 | 69.2% |

Biomarker analysis of skin biopsies showed reductions in LPA-related genes. A numerical improvement versus baseline of some disease biomarkers (COMP and TSP1) was observed in the initial Compound I group when the treatment duration was extended up to 24 weeks.

Compound I was well tolerated in patients with dcSSc. The MRSS improved during the study although the difference was not significant, and additional gene signature analysis suggested target engagement. In addition, there was clinically significant improvement in HAQ-DI (assesses functional disability) at week 24.

Example B-3: 52-Week Double-Blind, Randomized, Placebo-Controlled Study Diffuse in Patients with Cutaneous Systemic Sclerosis (dcSSc)

The overall objective is to investigate the efficacy, safety, and tolerability of 2 dose regimens of Compound I administered once daily (QD) or twice daily (BID) for 52 weeks in the treatment of subjects with diffuse cutaneous systemic sclerosis (diffuse cutaneous SSc).

Primary Objective

The primary objective is to demonstrate the efficacy of 1 or 2 dose regimens of Compound I versus placebo in subjects with diffuse cutaneous SSc, as determined by a comparison of change in forced vital capacity (FVC) % predicted after 52 weeks of treatment.

Secondary Objectives

Evaluate the effect of 2 dose regimens of Compound I versus placebo on Health Assessment Questionnaire-Disability Index [HAQ-DI] after 52 weeks of treatment.

Evaluate the effect of 2 dose regimens of Compound I versus placebo on Physician Global Assessment (MDGA) after 52 weeks of treatment.

Evaluate the effect of 2 dose regimens of Compound I versus placebo on Patient Global Assessment (PTGA) after 52 weeks of treatment.

Evaluate the effect of 2 dose regimens of Compound I versus placebo on the Physical Effects subscale of the scleroderma skin patient-reported outcome (SSPRO-18) after 52 weeks of treatment.

Evaluate the effect of 2 dose regimens of Compound I versus placebo on the Physical Limitations subscale of the SSPRO-18 after 52 weeks of treatment.

Evaluate the effect of 2 dose regimens of Compound I versus placebo on the modified Rodnan skin score (mRSS), after 52 weeks of treatment.

Evaluate the effect of 2 dose regimens of Compound I versus placebo on American College of Rheumatology-Composite Response Index Systemic Sclerosis (ACR-CRISS), defined as improvement in from Baseline in mRSS, HAQ-DI, PTGA, MDGA and FVC % predicted after 52 weeks of treatment.

Evaluate the effect of 2 dose regimens of Compound I versus placebo on ACR-CRISS-20, defined as improvement in ≥3 core set measures from Baseline of ≥20% in mRSS, ≥20% in HAQ-DI, ≥20% in PTGA, ≥20% in MDGA and ≥5% in FVC % predicted after 52 weeks of treatment.

Assess safety and tolerability of Compound I on adverse events (AEs), the adverse event of special interest (AESI) (orthostatic hypotension), concomitant medication use, vital signs, 12-lead electrocardiogram (ECG) and clinical safety laboratory evaluations (hematology, chemistry, inflammatory parameters, coagulation panel and urinalysis).

Evaluate the pharmacokinetics (PK) of Compound I and metabolite(s).

Exploratory Objectives

Evaluate the effect of 2 dose regimens of Compound I versus placebo on the SSPRO-18 after 52 weeks of treatment.

Evaluate the effect of 2 dose regimens of Compound I versus placebo on University of California Los Angeles Scleroderma Clinical Trial Consortium Gastrointestinal Tract (UCLA SCTC GIT 2.0) after 52 weeks of treatment.

Evaluate the effect of 2 dose regimens of Compound I versus placebo on Raynaud's phenomenon using the Raynaud's Assessment.

Evaluate the effect of 2 dose regimens of Compound I versus placebo on Scleroderma HAQ (SHAG) at Week 52.

Evaluate the effect of 2 dose regimens of Compound I versus placebo on change from Baseline in Systemic Sclerosis Quality of Life Questionnaire (SScQoL) scores.

Evaluate the effect of 2 dose regimens of Compound I versus placebo on change from Baseline in SF-12® Health Survey (SF-12) scores.

Evaluate the effect of 2 dose regimens of Compound I versus placebo on change from Baseline in pain and pain component scale scores.

Evaluate the effect of 2 dose regimens of Compound I versus placebo on change from Baseline in fatigue based on the Functional Assessment of Chronic Illness Therapy—Fatigue Scale (FACIT-F) score.

Evaluate the effect of 2 dose regimens of Compound I versus placebo on change from Baseline in protein expression of markers of inflammation and fibrosis in skin biopsies.

Evaluate the effect of 2 dose regimens of Compound I versus placebo on change from Baseline in transcriptomics associated with LPAR1 pathway, inflammation and fibrosis in skin biopsies.

Evaluate the effect of 2 dose regimens of Compound I versus placebo on change from Baseline in lung fibrosis after 52 weeks of treatment in subjects with suitable Baseline high resolution computed tomography (HRCT).

Evaluate the effect of 2 dose regimens of Compound I versus placebo on change from Baseline in diffusing capacity of the lungs for carbon monoxide (DLCO) after 52 weeks of treatment.

Evaluate the effect of 2 dose regimens of Compound I versus placebo on change from Baseline in serum and plasma biomarkers associated with LPAR1 pathway, inflammation and/or fibrosis.

Trial Design

This is a randomized, double-blind, placebo-controlled, repeat-dose, multicenter trial. Subjects will be screened within 4 weeks prior to the Baseline (Day 1) Visit. Approximately 300 subjects who meet the trial eligibility criteria will be randomized on Day 1 in a 1:1:1 ratio to receive Compound I 300 mg QD, Compound I 300 mg BID or placebo for 52 weeks. Randomization will be stratified according to Screening use of mycophenolate mofetil (yes/no) and presence of interstitial lung disease (ILD) (yes/no) based on a Screening HRCT scan.

The trial will include up to a 4-week Screening Period and a 52-week Double-blind Treatment Period. Subjects will take their first dose of trial drug at the clinic and will return to the clinic for trial visits at Week 4 and every 6 weeks thereafter until Week 52. All subjects who complete the Double-blind Treatment Period (Week 52) will be eligible to enter a 52-week extension trial. Subjects not entering the extension will return to the clinic for a Safety Follow-up Visit 4 weeks after the last dose of trial drug.

If a subject prematurely discontinues trial drug, he/she will be asked to remain in the trial, participating in the scheduled trial visits through Week 52. If a subject prematurely discontinues trial drug and does not wish to continue in the trial, he/she will be asked to return for a clinic visit and undergo the Week 52 assessments.

Inclusion Criteria

Eligible subjects must meet/provide all of the following criteria:

Written informed consent. Male or female between the ages of 18 and 75 years, inclusive, at Screening. Meets the 2013 American College of Rheumatology/European League Against Rheumatism classification criteria for SSc with a total score of ≥9 (Van den Hoogen et al., 2013). Classified as having skin involvement proximal to the elbow and/or knee (diffuse cutaneous SSc subset by LeRoy and Medsger, 2001). At the time of enrollment, less than 36 months since the onset of the first SSc manifestation, other than Raynaud's phenomenon. Skin thickening from SSc in the forearm suitable for repeat biopsy. mRSS units ≥15 at Screening. FVC ≥45% predicted at Screening, as determined by spirometry. Willing and able to comply with the prescribed treatment protocol and evaluations for the duration of the trial.

Exclusion Criteria

Subjects will be ineligible for trial participation if they meet any of the following criteria:

Positive for anti-centromere antibodies. Diagnosed with sine scleroderma or limited cutaneous SSc. Diagnosed with other autoimmune connective tissue diseases, except for fibromyalgia, scleroderma-associated myopathy and secondary Sjogren's syndrome. Scleroderma renal crisis diagnosed within 6 months of the Screening Visit. Any of the following cardiovascular diseases: uncontrolled, severe hypertension (≥160/100 mmHg) or persistent low blood pressure (systolic blood pressure <90 mmHg) within 6 months of Screening, myocardial infarction within 6 months of Screening, unstable cardiac angina within 6 months of Screening. DLCO <40% predicted (corrected for hemoglobin). If severe acute respiratory syndrome coronavirus 2 (SARS-CoV-2) exposure is of clinical concern for any subject, consider using a DLCO up to 6 months before the Screening Visit. Pulmonary arterial hypertension (PAH) by right heart catheterization requiring treatment with more than 1 oral PAH-approved therapy or any parenteral therapy. Treatment is allowed for erectile dysfunction and/or Raynaud's phenomenon/digital ulcers. Corticosteroid use for conditions other than SSc within 4 weeks prior to Screening (topical steroids for dermatological conditions and inhaled/intranasal/intra-articular steroids are allowed). Use of any other non-steroid immunosuppressive agent, small biologic molecule, cytotoxic or anti-fibrotic drug within 4 weeks of Screening, including cyclophosphamide, azathioprine (Imuran®) or other immunosuppressive or cytotoxic medication. Exceptions include mycophenolate mofetil (CellCept®), mycophenolic acid (Myfortic®), methotrexate and low-dose prednisone, as follows: use of CellCept ≤3 g/day, Myfortic ≤2.14 g/day, methotrexate ≤15 mg/week and prednisone ≤10 mg/day (or equivalent dosing of glucocorticoids) is allowed. See Table 9.1 for full details. Subjects taking CellCept, Myfortic or methotrexate must have been doing so for ≥6 months and the dose must have been stable for ≥16 weeks prior to the Day 1 Visit. Prednisone must have been at a stable dose for ≥8 weeks prior to the Day 1 Visit. It is acceptable to be on background low-dose prednisone and anti-malarial drug along with CellCept, Myfortic or methotrexate. Rituximab must not have been used within 6 months of the Day 1 Visit. Known active bacterial, viral, fungal, mycobacterial or other infection, including tuberculosis or atypical mycobacterial disease (fungal infections of nail beds are allowed). Use of a U.S. Food and Drug Administration-approved agent for SSc or an investigational agent for any condition within 90 days or 5 half-lives, whichever is longer, prior to Screening or anticipated use during the course of the trial. Malignant condition in the past 5 years (except successfully treated basal/squamous cell carcinoma of the skin or cervical cancer in situ). Women of childbearing potential (WOCBP) or male subjects not agreeing to use highly effective method(s) of birth control throughout the trial and for 1 month after last dose of trial drug. Pregnant or lactating women.

Previous enrollment in this trial or participation in a prior Compound I clinical trial. Any other condition that, in the opinion of the Investigator, would preclude enrollment in the trial.

Dosage Form, Strength, Dose Regimen, Route of Administration

Compound I 150 mg tablets and matching placebo tablets will be used in this trial.

Subjects will take 2 tablets of trial drug orally in the morning and evening with a meal.

Compound I 300 mg QD regimen: 2 Compound I tablets in the morning and 2 placebo tablets in the evening. Compound I 300 mg BID regimen: 2 Compound I tablets in the morning and 2 Compound I tablets in the evening.

Placebo regimen: 2 placebo tablets in the morning and 2 placebo tablets in the evening.

Duration of Treatment and Follow-Up

The planned duration of the Double-blind Treatment Period is 52 weeks. All subjects who complete the Double-blind Treatment Period will be eligible to enter into a 52-week extension trial. Subjects not entering the extension trial will return to the clinic 4 weeks after the last dose of trial drug for a Safety Follow-up Visit.

Criteria for Evaluation

Efficacy will be assessed by FVC % predicted, MDGA, mRSS, ACR-CRISS, patient-reported outcomes (HAQ-DI, SHAQ global questions, PTGA, SSPRO-18, UCLA SCTC GIT 2.0 and Raynaud's Assessment), quality-of-life, health status and fatigue evaluations (SScQoL, SF-12, pain scores and fatigue scores [FACIT-F]), HRCT and DLCO.

Blood samples for Compound I and metabolite(s) PK assessment, pharmacogenetic assessment (for drug metabolizing enzymes and/or transporters), autoantibodies and biomarkers associated with the LPAR1 pathway, inflammation or fibrosis will be collected.

A total of four 3-mm biopsies (2 pre-dose at Baseline [Day 1] and 2 at Week 16) will be taken from the forearm (lesional) to analyze for transcriptomics as well as protein expression in skin for markers of the LPAR pathway, fibrosis and inflammation. If involved skin is located in that area, then the involved skin should be used.

Safety will be assessed via AEs, concomitant medication use, physical examinations, vital signs, orthostatic hypotension assessment, laboratory evaluations and 12-lead ECG.

Efficacy Variables

Spirometry

Spirometry, including FVC % predicted, will be assessed using a device provided by the Sponsor. Spirometry should only be performed by a trained assessor and the same assessor should complete the procedure for a given subject throughout the duration of the trial, unless it is not possible.

Spirometry measurements must be performed according to American Thoracic Society (ATS)/European Respiratory Society (ERS) 2019 guidelines [Graham et al., Standardization of Spirometry 2019 Update. An Official American Thoracic Society and European Respiratory Society Technical Statement. Am J Respir Crit Care Med. 2019; 200: e70-e88]. The test will be done in triplicate (3 curves to be provided) and the best result selected according to the guidelines. The best of 3 efforts will be defined as the highest FVC, obtained on any of the 3 blows meeting the ATS/ERS criteria with a maximum of 8 maneuvers.

Spirometry measurements should be attempted at approximately the same time of day from Baseline onwards. On days of clinic visits, subjects must refrain from strenuous activity at least 12 hours prior to pulmonary function testing. Smoking should be discouraged throughout the visit days and will not be permitted in the 30-minute period prior to spirometry. Subjects should also avoid cold temperatures, environmental smoke, dust or areas with strong odors (e.g., perfumes). If treated with bronchodilators, washout of 24 hours for long-acting and 8 hours for short-acting bronchodilators should be observed before spirometry.

Physician Global Assessment

The MDGA is an 11-point Likert scale ranging from 0 to 10 (0=excellent to 10=extremely poor) on which the physician rates the subject's overall health over the past week. There is also a 5-point scale (from 1 to 5; 1=much better to 5=much worse) on which the physician rates the subject's overall scleroderma condition compared to the last clinic visit.

Modified Rodnan Skin Score

The mRSS is a validated method for estimating skin thickening. Seventeen different body areas are scored as normal (0), mild thickening (1), moderate thickening (2) and severe thickening (3), with a maximum score of 51. The assessment should be performed by the Investigator (or designee) who is trained in skin scoring. Except when strictly unavoidable, the same person should perform the assessment at each evaluation during the trial.

American College of Rheumatology-Composite Response Index in Systemic Sclerosis

Subjects will be evaluated using the ACR-CRISS, an outcome measure for diffuse cutaneous SSc. The ACR-CRISS includes core items that assess change in 2 prominent manifestations of early diffuse cutaneous SSc (skin and ILD), functional disability (HAQ-DI) and patient and physician global assessments. In addition, the score captures a clinically meaningful worsening of internal organ involvement requiring treatment.

The ACR-CRISS is a 2-step process that assigns a probability of improvement for a subject that ranges from 0.0 (no improvement) to 1.0 (marked improvement). Step 1 will be evaluated as part of the AE assessment, at which time the Investigator will assess if a subject has developed new or worsening cardiopulmonary and/or renal involvement due to SSc, as outlined below.

New scleroderma renal crisis, defined as follows (adapted from Steen et al., Assessment of kidney involvement. Clin Exp Rheumatol. 2003; 21(3Supp129):529-31):

Hypertensive scleroderma renal crisis:

1. New onset hypertension, defined as any of the following: systolic blood pressure 2140 mmHg; diastolic blood pressure 290 mmHg; rise in systolic blood pressure 230 mmHg; rise in diastolic blood pressure 220 mmHg

AND

2. One of the following 5 features: increase in serum creatinine by 250% over Baseline OR serum creatinine 2120% of ULN for local laboratory; proteinuria 22+ by dipstick; hematuria 22+ by dipstick or 210 red blood cells/high-powered field; thrombocytopenia: <100,000 platelets/mm3; hemolysis, defined as anemia not due to other causes and either of the following: i) schistocytes or other red blood cell fragments seen on blood smear, or ii) increased reticulocyte count Normotensive scleroderma renal crisis:

1. Increase in serum creatinine >50% over Baseline OR serum creatinine 2120% of ULN for local laboratory:

AND

2. One of the following 5 features:proteinuria 22+ by dipstick; hematuria 22+ by dipstick or 210 red blood cells/high-powered field; thrombocytopenia: <100,000 platelets/mm3; hemolysis, defined as anemia not due to other causes and either of the following: i) schistocytes or other red blood cell fragments seen on blood smear, or ii) increased reticulocyte count; Renal biopsy findings consistent with scleroderma renal crisis (microangiopathy)

Decline in FVC % predicted ≥15% (relative), confirmed by another FVC % within a month, HRCT to confirm ILD (if previous scan did not show ILD) and FVC % predicted <80%

New onset of left ventricular failure (defined as ejection fraction ≤45%) requiring treatment New onset of PAH on right heart catheterization requiring treatment.

Gastrointestinal dysmotility requiring enteral (tube feeding) or parenteral nutrition Digital ischemia with gangrene, amputation, or hospitalization requiring treatment If a subject meets any of these criteria, the subject is assigned a probability of 0. Otherwise, in Step 2, the probability of improvement is calculated based on the 5 core measures incorporated into the ACR-CRISS, including changes in mRSS, FVC % predicted, HAQ-DI, PTGA and MDGA [Khanna and Berrocal et al., The American College of Rheumatology Provisional Composite Response Index for Clinical Trials in Early Diffuse Cutaneous Systemic Sclerosis. Arthritis Rheumatol. 2016; 68(2):299-311].

Skin (Lesional) Biopsy

Skin (lesional) biopsies will be obtained from the mid dorsal surface of the forearm (150±20 mm proximal to the ulnar styloid). If involved skin is located in that area, then the involved skin should be used. A biopsy should be performed regardless of whether or not involved skin is present. The biopsies will be used to analyze for transcriptomics as well as protein expression in skin for markers of the LPAR pathway, fibrosis and inflammation.

Two 3-mm skin punch biopsies will be taken next to each other on each of the days that biopsies are collected. The biopsies will be obtained according to standard dermatologic practice. After the biopsies are performed, the Investigator will advise subjects regarding care of the site. The biopsies should be taken from the same arm, approximately 25 mm away from the previous biopsy, to avoid healing of the previous biopsy interfering with analysis.

The location of the biopsy (right or left forearm) and distance from the ulnar styloid will be documented. If, in the opinion of the Investigator, the mid dorsal forearm is not appropriate, the ventral forearm can be selected as the site for the biopsy. The alternative site and the reason for changing the site will be documented.

Investigators have the discretion to manage the biopsy site closure per the standard of care at their site; however, a suture or the use of gelfoam is recommended.

Only the first 110 consenting subjects will have these biopsies completed.

Plasma and Serum Biomarkers

Blood samples will be collected prior to dosing on Day 1, Week 4 and Week 28 as well as at the Week 52 Visit for analysis of plasma and serum biomarkers associated with the LPAR1 pathway, inflammation or fibrosis. Examples of biomarkers that may be measured include, but are not limited to, proteins associated with the complement pathway and components of extracellular matrix pathways.

Only subjects who are able to provide a Baseline blood sample for serum and plasma biomarkers will have this assessment completed.

Lung High Resolution Computed Tomography

Lung HRCT will be reviewed by a central reader. These results must be available prior to randomization. If HRCT has been performed for clinical care in the 3 months prior to Screening and has been reviewed and deemed acceptable per central reader, then HRCT need not be performed at Screening.

Diffusing Capacity of the Lungs for Carbon Monoxide

The site will use its own DLCO equipment and conduct all measurements with the same DLCO equipment in case that several devices are available at the site. Single-breath DLCO measurement will be carried out according to the ATS guideline on DLCO measurements [Graham et al., Executive Summary: 2017 ERS/ATS standards for single-breath carbon monoxide uptake in the lung. Eur Respir J. 2017; 49:16E0016].

DLCO values will be adjusted for altitude, carboxyhemoglobin and the most recent hemoglobin value. The DLCO assessment should always be performed after the FVC measurement and should always be started approximately the same time each day.

Patient-Reported Outcome Assessments

Health Assessment Questionnaire—Disability Index

The HAQ-DI, which is part of the SHAQ, assesses the subject's level of functional ability and includes questions of fine movements of the upper extremity, locomotor activities of the lower extremity and activities that involve both upper and lower extremities. There are 20 questions in 8 categories of functioning including dressing, rising, eating, walking, hygiene, reach, grip and usual activities [Cole et al., Single-factor scoring validation for the Health Assessment Questionnaire-Disability Index (HAQ-DI) in patients with systemic sclerosis and comparison with early rheumatoid arthritis patients. Qual Life Res. 2006; 15(8):1383-94]. The subject's ability to accomplish each activity in the past week is indicated as: without any difficulty, with some difficulty, with much difficulty and unable to do. Any devices that are usually used to complete activities and any categories for which help from another person is needed is also assessed.

Patient Global Assessment

The PTGA is an 11-point Likert scale ranging from 0 to 10 (0=excellent to 10=extremely poor) on which the subject rates his/her overall health and illness-related pain level over the past week and how much the skin involvement due to scleroderma has interfered with daily activity and how rapidly the skin disease has been progressing over the past month. There is also a 5-point Likert scale (from 1 to 5; 1=much better to 5=much worse) on which the subject rates overall scleroderma skin involvement compared to the last clinic visit.

Scleroderma Skin Patient-Reported Outcome Instrument

The SSPRO-18, developed through concept elicitation in patients with diffuse cutaneous and limited cutaneous SSC based on 3 focus groups, is an 18-item, patient-reported outcome instrument that specifically assesses skin-related quality of life in patients with SSc and was developed with extensive patient input and according to the FDA patient-reported outcomes guidance [Man et al., Development and validation of a patient-reported outcome instrument for skin involvement in patients with systemic sclerosis. *Ann Rheum Dis.* 2017; 76:1374-80]. The SSPRO-18 comprises 4 major conceptual constructs—physical effects, emotional effects, physical limitations and social effects—and has reproducibility and high internal consistency. This instrument reflects how subjects feel and function from several different health perspectives. Good test-retest reliability and construct validity has been shown. Responsiveness has been shown for lenabasum vs placebo [Spiera et al., Safety and efficacy of lenabasum in a Phase II, randomized, placebo-controlled trial in adults with systemic sclerosis. *Arthritis Rheumatol.* 2020; 72(8):1350-60].

Scleroderma Health Assessment Questionnaire

The SHAQ consists of the HAQ-DI (8 domains) and also includes a VAS for pain and the following scleroderma-specific VASs: patient global assessment, vascular, digital ulcers, lung involvement and gastrointestinal involvement [Steen and Medsger, 1997]. Developers added the global questions to the HAQ-DI based on evaluation of SSc patients at the University of Pittsburgh Scleroderma Clinic, their HAQ scores, patient report of symptoms and lab tests. The 5 scleroderma-specific VASs ask subjects how much symptoms interfere with daily activities and are scored similarly to a pain VAS. Each VAS score is reported individually. Studies have supported excellent test-retest reliability and construct validity (correlation with other measures in the direction and to the magnitude expected) and responsiveness of abatacept vs placebo for the global questions from the SHAQ [Johnson et al., The Health Assessment Questionnaire Disability Index and Scleroderma Health Assessment Questionnaire in scleroderma trials: an evaluation of their measurement properties. *Arthritis Rheum.* 2005; 53:256-62; Smyth et al., A cross-sectional comparison of three self-reported functional indices in scleroderma. Rheumatology. 2003; 42(6):732-8; Khanna et al., Abatacept in early diffuse cutaneous systemic sclerosis: results of a phase 2 investigator-initiated, multicenter, double-blind, randomized, placebo-controlled trial. *Arthritis Rheumatol.* 2020; 72:125-36].

UCLA Scleroderma Clinical Trial Consortium Gastrointestinal Tract Instrument

The UCLA SCTC GIT 2.0 captures SSc-related gastrointestinal activity and severity. This instrument is an improvement over the scleroderma gastrointestinal tract (SSC-GIT 1.0) instrument because it is shorter (34 items versus 52 items) but still reliable and valid instrument that differentiates reflux symptoms from symptoms of distension/bloating, adds a scale to evaluate rectal incontinence because of its high prevalence in SSc and develops a composite score that captures overall gastrointestinal tract burden associated with SSc [Khanna et al., Reliability and validity of UCLA Scleroderma Clinical Trial Consortium Gastrointestinal Tract (UCLA SCTC GIT 2.0) instrument. *Arthritis Rheumatol.* 2009; 61(9):1257-63].

The UCLA SCTC GIT 2.0 has 7 scales—reflux, distension/bloating, diarrhea, fecal soilage, constipation, emotional well-being and social functioning; a total GIT score is also calculated to capture overall burden of SSc-associated gastrointestinal involvement. Items are scored on a 0 to 3 scale and do not require conversion to a 0 to 100 scale.

Raynaud's Assessment

The Raynaud's Condition Score Diary captures frequency, duration and severity of Raynaud's phenomenon activity and has face, content, criterion, discriminant and construct validity in subjects with SSc [Merkel et al., *J Rheumatol.* 2003; 30:1630-47]. Subjects will be provided an electronic device to capture symptoms daily through Week 52.

Systemic Sclerosis Quality of Life Questionnaire

The SScQoL, developed through concept elicitation interviews in patients with diffuse cutaneous and limited cutaneous SSc, is a validated tool that has 29 questions divided into 5 subscales relating to physical functioning, emotional functioning, social functioning, sleep and pain, which are important disease-specific factors associated with quality of life in SSc [Sierakowska et al., Factors associated with quality of life in systemic sclerosis: a cross-sectional study. *Qual Life Res.* 2019; 28:3347-54]. Good test-retest reliability and construct validity has been shown [Reay N. The quality of life in patients with diffuse and limited systemic sclerosis. Published online 2008. https://etheses.whiterose.ac.uk/26111/1/503274.pdf]. No studies have yet determined responsiveness to date.

SF-12 Health Survey

The SF-12 [Ware et al., A 12-Item Short-Form Health Survey: construction of scales and preliminary tests of reliability and validity. *Med Care.* 1996; 34:220-33] is a 12-item survey used to assess general health-related quality of life. The SF-12 items are scored to generate a physical component score (PCS) and mental component score (MCS) from the subject's perspective. The SF-12 examines 8 domains of health outcomes, including physical functioning, role-physical, bodily pain, general health, vitality, social functioning, role-emotional and mental health.

Pain Questionnaire

Subjects will complete a pain questionnaire that has 3 questions regarding the severity of pain experienced during the past week due to Raynaud's, arthritis and finger ulceration and/or calcinosis. Subjects will rate their pain from 0 (no pain) to 10 (very severe pain).

Functional Assessment of Chronic Illness Therapy—Fatigue Scale

The FACIT-F is a 13-item measure that assesses self-reported fatigue and its impact upon daily activities and function. It was developed in the mid-1990s to meet a growing demand for more precise evaluation of fatigue associated with anemia in cancer patients. Subsequent to its development, it has been employed in over 150 published studies, including over 40,000 patients. Studied groups have included patients with cancer, rheumatoid arthritis, osteoarthritis, psoriatic arthritis, ankylosing spondylitis, multiple sclerosis, psoriasis and SSc. The FACIT-F is reliable and valid in subjects with SSc [Harel et al., Canadian Scleroderma Research Group. Measuring fatigue in SSc: a comparison of the Short Form-36 Vitality subscale and Functional Assessment of Chronic Illness Therapy-Fatigue scale. *Rheumatology* (*Oxford*) 2012:51:2177-85; Strickland et al., Predictors of health-related quality of life and fatigue in systemic sclerosis: evaluation of the EuroQol-5D and FACIT-F assessment tools. *Clin Rheumatol.* 2012; 31:1215-22].

Example B-4: Pharmacokinetics (PK) of Compound I and the Effect of Food in Healthy Adult Subjects The PK of Compound I and food effect were evaluated in an open-label study in healthy volunteers to inform the dose and dosing condition of the tablet formulations used in the clinical studies. Dose proportionality and food effect were evaluated using a 2-way, 2-period crossover design in two cohorts:150 mg and 300 mg single dose under fasting condition in Cohort 1 and 450 mg single dose under fasting and high-fat, high calorie meal condition in Cohort 2. Multiple-dose PK was evaluated using a 2-period, fixed sequence crossover design. Subjects received Compound I twice a day (BID) of 300 mg (Cohort 3) or 450 mg (Cohort 4) administered with low-fat meals in Period 1 and with high-fat meals in Period 2.

PK sample collections: For cohort 1 and 2, blood samples were collected at predose, 0.5, 1, 2, 3, 4, 6, 8, 12, 24, 36, 48, 72, 96 and 120 h post dose. For cohort 3 and 4, blood samples were collected at predose, 0.5, 1, 2, 4, 5, 12 hrs after the first dose on Day 1. After the last dose on Day 5, PK samples were taken at predose, 0.5, 1, 2, 4, 6, 12, 24, 36, 60, 84, 108 hr in Period 1 and predose, 0.5, 1, 2, 4, 6, 12 hours post last dose in Period 2.

Plasma concentrations of Compound I were determined using a validated high performance liquid chromatography-tandem mass spectrometry (HPLC MS/MS) method. The analytical range of Compound I were 250-50,000 ng/mL (high range) and 25-25,000 ng/mL (low range). Dose-proportionality of pharmacokinetic parameters were examined by analysis of variance (ANOVA) where the $AUC_{0\text{-}last}$, $AUC_{0\text{-}inf}$, and $C_{max}$ parameters were dose normalized. 90% confidence intervals (CIs) were derived by exponentiation of the CIs obtained for the difference between the treatment LSMs (Least square means). Dose proportionality was established if the 90% CI for the ratio of the geometric means for the dose-normalized parameters lay within the limits of (0.7, 1.43).

Food effect was evaluated using ANOVA on the ln-transformed PK parameters. The ANOVA model included sequence, treatment, and period as fixed effects and subject nested within sequence as a random effect. Geometric least square means, geometric mean ratio (High fat vs. fasted) and 90% confidence interval of PK parameters (AUC and Cmax) were calculated from the ANOVA model.

Compound I Cmax and AUC increased in a less than dose-proportional manner from 150 to 450 mg, with minimal exposure increase from 300 mg to 450 mg (see Table below). Less than dose proportional PK by ANOVA analysis.

PK Parameters Following a 150, 300 and 450 mg Dose Administered Under Fasted Conditions

| Compound I Dose | Cmax (ng/mL) | $AUC_{0\text{-}inf}$ (ng*h/mL) | $AUC_{0\text{-}last}$ (ng*h/mL) | $T_{max}$ (hr) | $t_{1/2}$ (hr) |
|---|---|---|---|---|---|
| 150 mg | 11100 (47%) | 85200 (37%) | 83800 (37%) | 3.5 | 21.8 |
| 300 mg | 14500 (40%) | 120000 (32%) | 118000 (32%) | 4.0 | 22.4 |
| 450 mg | 15200 (49%) | 126000 (47%) | 125000 (47%) | 3.0 | 18.3 |

At 450 mg, high-fat, high-calorie meal increased the exposure of Compound I. The GMRs of Compound I $AUC_{0\text{-}last}$, $AUC_{0\text{-}inf}$ and $C_{max}$ were approximately 212%, 212% and 191%, respectively, for dosing with high-fat meals compared to dosing under fasted conditions (see following table).

Summary of Statistical Comparisons of Compound I Pharmacokinetic Parameters at 450 mg Following Fed and Fasted Conditions

| | Geometric LSM[1] | | | |
|---|---|---|---|---|
| | Fed[3] | Fasted | GMR[2] (%) | 90% Confidence Interval (%) |
| AUC0-last (ng · hr/mL) | 245900 | 115800 | 212.37 | 175.15-257.49 |
| AUC0-inf (ng · hr/mL) | 248300 | 117000 | 212.23 | 175.12-257.20 |
| Cmax (ng/ml) | 26680 | 13980 | 190.85 | 1.64-225.34 |

Similar Compound I exposure was achieved following administration of 300 mg BID with meal compared to results seen in the Example B-3 study. Therefore, 300 mg BID with meal was selected as the top dose for the following studies, with 300 mg QD dose also included to inform the dose-response relationship for Compound I.

Compound I Pharmacokinetic Parameters at Steady State Following Fed Conditions

| Dose (mg) | Meal Condition | $C_{max,ss}$ (ng/mL) | $AUC_{tau}$ (ng · h/mL) | $C_{trough}$ (ng/mL) | $t_{1/2}$ (hr) |
|---|---|---|---|---|---|
| 300 | Low-fat meal[1] | 15900 (28%) | 129000 (23%) | 6570 (13%) | 24.6 |
| 300 | High-fat meal[2] | 21700 (29%) | 166000 (24%) | 8627 (17%) | 24.6 |
| 450 | Low-fat meal[1] | 18400 (22%) | 163000 (23%) | 11000 (35%) | 27.7 |
| 450 | High-fat meal[3] | 25800 (35%) | 204000 (35%) | 11000 (23%) | 27.7 |

[1]Low fat meals as in FDA guidance, containing 11-14 g of fat, 400-500 total calories, 25% of calories from fat.
[2]High fat, reduced calorie meals, containing 33-44 g of fat, 600-800 total calories, 50% of calories from fat.
[3]High fat, high calorie meal as in FDA guidance, containing 55-65 g of fat, 800-1000 total calories, 50% of calories from fat. Data are presented as mean (% CV), except for $t_{1/2}$, which is presented as median.

Example B-5: A Multicenter, Open-Label Extension Trial to Evaluate the Efficacy, Safety and Tolerability of Compound I in Subjects with Diffuse Cutaneous Systemic Sclerosis This is an open label, repeat-dose, multicenter extension trial of Example B-3. Subjects who complete the double-blind Treatment Period (Week 52) in Trial Example B-3 will be eligible to enter this 52-week extension trial.

On Day 1 (Week 52 Visit of Example B-3), subjects will receive their first dose of Compound I in this extension trial at the clinic and will return to the clinic for trial visits at Week 4 and every 6 weeks thereafter until Week 52.

If a subject prematurely discontinues trial drug, he/she will be asked to remain in the trial, participating in the scheduled trial visits through Week 52. If a subject prematurely discontinues trial drug and does not wish to continue in the trial, he/she will return for a clinic visit and undergo the Week 52 assessments. Subjects will return to the clinic for a Safety Follow-up Visit 4 weeks after the last dose of Compound I.

Subject Population

Inclusion Criteria:

Written informed consent. Completed the double-blind Treatment Period (Week 52) in Trial Example B-3; subjects prematurely discontinued from trial drug in Trial Example B-3 for reasons other than safety or toxicity can be included at the discretion of the Investigator after completing Trial Example B-3 scheduled visits, including Week 52 assessments. Willing and able to comply with the prescribed treatment protocol and evaluations for the duration of the trial.

Exclusion Criteria:

Anticipated use of another investigational agent for any condition during the course of the trial. New diagnosis of malignant condition after enrolling in Trial Example B-3 (except successfully treated basal/squamous cell carcinoma of the skin or cervical cancer in situ). Women of childbearing potential (WOCBP) or male subjects not agreeing to use highly effective method(s) of birth control throughout the trial and for 1 month after last dose of trial drug. Pregnant or lactating women. Any new development with the subject's disease or condition or any significant laboratory test abnormality during the course of Trial Example B-3 that, in the opinion of the Investigator, would potentially put the subject at unacceptable risk. Subjects will be ineligible if, in the opinion of the Investigator, they are unlikely to comply with the trial protocol or have a concomitant disease or condition that could interfere with the conduct of the trial.

Dosage Form, Strength, Dose Regimen, Route of Administration

Compound I 150 mg tablets will be used in this trial. The dose regimen for all subjects will be Compound I 300 mg BID. Subjects will take 2 Compound I 150 mg tablets orally in the morning and evening with a meal.

Endpoints

Two types of Baseline are defined: Trial Baseline, defined as the latest measurement prior to the first dose of Compound I in this extension trial. Compound I Baseline, defined as the latest measurement prior to the first dose of Compound I in either Trial Example B-3 or this extension trial. For subjects who received placebo in Trial Example B-3, Trial Baseline will be the same as Compound I Baseline.

Primary Efficacy Endpoint

The primary endpoint is the change from both Baselines in FVC % predicted at Week 52.

Exploratory Efficacy Endpoints

Change from both Baselines in HAQ-DI at Week 52.

Change from both Baselines in MDGA at Week 52.

Change from both Baselines in PTGA at Week 52.

Change from both Baselines in the Physical Effects subscale of the SSPRO-18 at Week 52.

Change from both Baselines in the Physical Limitations subscale of the SSPRO-18 at Week 52.

Proportion of subjects with an mRSS decrease of ≥5 points and 25% from both Baselines at Week 52.

Responder rate (defined as ACR-CRISS [predicted probability] of at least 0.6) at Week 52.

Proportion of subjects with an improvement in ≥3 of 5 core measures from both Baselines: ≥20% in mRSS, ≥20% in HAQ-DI, ≥20% in PTGA, ≥20% in MDGA and ≥5% for FVC % predicted at Week 52 (ACR-CRISS-20).

Change from both Baselines in the SSPRO-18 at Week 52.

Change from both Baselines in each scale of the UCLA SCTC GIT 2.0 and the total GIT score at Week 52.

Change from both Baselines in Raynaud's phenomenon using the Raynaud's Assessment at Week 52.

Change from both Baselines in the SHAQ at Week 52.

Change from both Baselines in SScQoL scores at Week 52.

Change from both Baselines in SF-12 scores at Week 52.

Change from both Baselines in pain and pain component scale scores at Week 52.

Change from both Baselines in the FACIT-F score at Week 52.

Change from both Baselines in the mRSS at Week 52.

Change from both Baselines in lung fibrosis based on HRCT at Week 52.

Change from both Baselines in DLCO at Week 52.

Change from both Baselines in serum and plasma biomarkers associated with LPAR1 pathway, inflammation and/or fibrosis at Week 52.

Safety and Tolerability Endpoints

Incidence of TEAEs and the AESI (orthostatic hypotension). Concomitant medication use. Change from both Baselines in vital signs. Change from both Baselines in 12-lead ECG measurements. Change from both Baselines in clinical safety laboratory test results.

Pharmacokinetic Endpoint

Pre- and post-dose concentrations of Compound I and metabolite(s).

Rescue Medications Allowed Due to Clinically Significant Deterioration

Initiation/change in dose permitted in case of clinically significant deterioration, defined as: an absolute decline since Trial Baseline in FVC % predicted ≥10% or an absolute decline since Trial Baseline in FVC % predicted ≥5 to 9% with associated decline in DLCO ≥15% since Trial Baseline; or relative change since Trial Baseline in mRSS of >25% and an absolute change since Trial Baseline of >5 points; or clinically significant deterioration in other organ systems or that does not meet above criteria, per Investigator assessment, may be appropriate (consultation with the Medical Monitor should occur prior).

Other causes for FVC decline (i.e., respiratory tract infection) should be excluded. Repeat FVC/spirometry should be performed and confirmed prior to initiation of rescue medication if, to the Investigator's clinical judgment, well-founded doubts in the test's quality and the subject's good condition justify the associated delay in subject care, and the increase in risk for the subject.

Compound I is an in vitro inhibitor of organic anion transporters 1 and 3 (OAT1 and OAT3) and may increase the systemic exposures of methotrexate.

DLCO=diffusing capacity of the lungs for carbon monoxide; FVC=forced vital capacity; mRSS=modified Rodnan skin score; OATP=organic anion transporter polypeptide.

| Medication | Treatment and Post-treatment Follow-up Periods |
|---|---|
| Non-steroidal medication | |
| Stable therapy with mycophenolate mofetil/ CellCept ≤3 g/day, Myfortic ≤2.14 g/day | Pre-trial dose to be continued except for deterioration |
| Methotrexate ≤15 mg/week | Pre-trial dose to be continued except for deterioration (≤15 mg/week in any event) |
| Azathioprine | Not permitted except for deterioration |
| Cyclophosphamide | Not permitted except for deterioration |
| Hydroxychloroquine | Pre-trial dose to be continued except for deterioration |
| Colchicine, D-penicillamine, sulfasalazine | Not permitted except for deterioration |
| Rituximab | Not permitted except for deterioration |
| Tocilizumab, abatacept, leflunomide, tacrolimus, newer antiarthritic treatments such as tofacitinib, potassium para-aminobenzoate | Not permitted except for deterioration |
| Pirfenidone | Not permitted except for deterioration |
| Nintedanib | Not permitted except for deterioration |
| Steroids | |

-continued

| Medication | Treatment and Post-treatment Follow-up Periods |
|---|---|
| Prednisone >10 mg/day | Not permitted except for deterioration |

Example B-6: A Phase 2b Trial to Evaluate the Efficacy, Safety and Tolerability of Compound I in Subjects with Idiopathic Pulmonary Fibrosis (IPF)

The trial will be conducted in 2 parts, Part 1 (Core Phase) followed by Part 2 (Extension Phase). The Core Phase will include a 52-week, randomized, double-blind, placebo-controlled treatment period and the Extension Phase will include a 52-week, open-label extension (OLE).

Part 1 (Core Phase)

The overall objective of the Core Phase is to investigate the efficacy, safety and tolerability of 2 dose regimens of Compound I, a selective antagonist of LPAR1, administered QD or BID for 52 weeks in the treatment of subjects with IPF.

Primary Objective

The primary objective is to demonstrate the efficacy of 2 dose regimens of Compound I versus placebo in subjects with IPF, as determined by a comparison of change in FVC % predicted after 52 weeks of treatment.

Secondary Objectives

Evaluate the effect of 2 dose regimens of Compound I versus placebo on the proportion of subjects with decline in FVC % predicted ≥10% from Baseline after 52 weeks of treatment.

Evaluate the effect of 2 dose regimens of Compound I versus placebo on the changes from Baseline in the 6-Minute Walk Test (6MWT) after 52 weeks of treatment.

Evaluate the effect of 2 dose regimens of Compound I versus placebo on the King's Brief Interstitial Lung Disease Questionnaire (K-BILD) after 52 weeks of treatment.

Evaluate the effect of 2 dose regimens of Compound I versus placebo on the L-IPF after 52 weeks of treatment.

Evaluate the effect of 2 dose regimens Compound I versus placebo on the Leicester Cough Questionnaire (LCQ) after 52 weeks of treatment.

Evaluate the effect of 2 dose regimens of Compound I versus placebo on the rate of hospitalization due to respiratory distress up to 52 weeks of treatment.

Evaluate the effect of 2 dose regimens of Compound I versus placebo on the composite endpoint of progression-free survival (PFS), where progression includes decline in FVC % predicted ≥10% from Baseline or death over 52 weeks of treatment.

Assess safety and tolerability of Compound I, inclusive of, but not limited to, adverse events (AEs), SAES and AESI.

Evaluate the PK of Compound I.

Exploratory Objectives

Evaluate the effect of 2 dose regimens of Compound I versus placebo on change from Baseline in SF-12® Health Survey (SF-12) scores after 52 weeks of treatment.

Evaluate the effect of 2 dose regimens of Compound I versus placebo on change from Baseline in titrated oxygen requirement (TOR) after 52 weeks of treatment.

Evaluate the effect of 2 dose regimens of Compound I versus placebo on change from Baseline in DLCO after 52 weeks of treatment.

Evaluate the effect of 2 dose regimens of Compound I versus placebo on time to first IPF-related acute exacerbation (as defined by Collard et al., Acute exacerbation of idiopathic pulmonary fibrosis. an international working group report. Am J Respir Crit Care Med. 2016; 194(3): 265-75) from Baseline up to 52 weeks of treatment.

Evaluate the effect of 2 dose regimens of Compound I versus placebo on all-cause mortality up to 52 weeks of treatment.

Evaluate the effect of 2 dose regimens of Compound I versus placebo on mortality due to respiratory deterioration up to 52 weeks of treatment Evaluate the effect of 2 dose regimens of Compound I versus placebo on mortality due to IPF disease-related events up to 52 weeks of treatment.

In subjects having adequate Baseline (Screening or within 6 months prior to Screening) and 52-week HRCT scans, evaluate the effect of 2 dose regimens of Compound I versus placebo on the following after 52 weeks of treatment: Change from Baseline in total lung volume of high-resolution computed tomography (HRCT); Change from Baseline in volume of lung fibrosis scores on HRCT; % change from Baseline of total lung volume of lung fibrosis scores on HRCT; Change from Baseline in volume of normal lung on HRCT; % change from Baseline in FVC % predicted and the relationship to mean % change from Baseline in lung fibrosis scores.

Part 2 (Extension Phase)

The overall objective of the Extension Phase is to investigate the long-term efficacy, safety and tolerability of Compound I, administered at a dose of 300 mg BID to subjects with IPF in a 52-week OLE following completion of the Core Phase of the trial. The dose for the Extension Phase may be modified based on the results of the Core Phase.

Two types of Baseline are defined for the Extension Phase: OLE Baseline, defined as the latest measurement prior to the first dose of Compound I in Extension Phase; or Compound I Baseline, defined as the latest measurement prior to the first dose of Compound I in either the Core Phase or the Extension Phase. For subjects who received placebo in the Core Phase, OLE Baseline will be the same as Compound I Baseline.

Primary Objective

The primary efficacy objective is to assess the efficacy of Compound I in subjects with IPF after 52 weeks of open-label treatment.

Safety Objective

The safety objective is to examine the safety and tolerability of 52 weeks of open-label treatment with Compound I based on: TEAE assessment; Concomitant medication use; Vital signs; 12-lead electrocardiogram (ECG); Clinical safety laboratory results.

Exploratory Objectives

The exploratory efficacy objective is to evaluate the efficacy of 52 weeks of open-label treatment with Compound I via additional efficacy measurements: Proportion of subjects with decline in FVC % predicted ≥10%; 6MWT; K-BILD; L-IPF; LCQ; SF-12 scores; Hospitalization due to respiratory distress; Composite endpoint of PFS, where progression includes decline in FVC % predicted ≥10% or death; TOR; DLCO; IPF-related acute exacerbation; All-cause mortality; Mortality due to IPF disease-related events; HRCT scans: total lung volume, volume of lung fibrosis scores, total lung volume of lung fibrosis scores, volume of normal lung on HRCT.

The exploratory PK objective is to evaluate the PK of Compound I

Overall Trial Design and Plan

This is a randomized, double-blind, placebo-controlled, repeat-dose, multicenter trial to evaluate the efficacy, safety and tolerability of Compound I in subjects with IPF. Subjects will be screened within 8 weeks prior to the Baseline (Day 1) Visit. Approximately 135 subjects who meet the trial eligibility criteria will be randomly assigned in a 1:1:1 ratio on Day 1 to receive Compound I 300 mg once daily (QD), Compound I 300 mg twice daily (BID) or placebo for 52 weeks using the following 2 stratification factors:

Prior use of approved IPF therapy (i.e., nintedanib or pirfenidone): yes or no

FVC % predicted at Baseline: ≥70% or <70%

The Core Phase will include up to an 8-week Screening Period and a 52-week Double-blind Treatment Period. Subjects will take their first dose of trial drug at the clinic on Day 1 (Week 0) and will participate in trial visits at Week 4 and every 6 weeks thereafter until Week 52. Subjects who complete the 52-week Double-blind Treatment Period may be eligible to enroll into the Extension Phase of the trial. If the subject does not enroll into the Extension Phase, a Safety Follow-up Visit will occur 4 weeks after the last dose of trial drug.

If a subject prematurely discontinues trial drug, he/she will be asked to remain in the trial, participating in the scheduled trial visits through Week 52. If a subject prematurely discontinues trial drug and does not wish to continue in the trial, he/she will be asked to return for a clinic visit and undergo the Week 52 assessments.

The Extension Phase of the trial is an optional, open-label, repeat-dose, multicenter extension of the Core Phase. Subjects who complete the Double-blind Treatment Period (Week 52) in the Core Phase of the trial may be eligible to enter this 52 week Extension Phase. Subjects entering the Extension Phase will complete the Week 52 Visit, which will be considered Day 1 of the Extension Phase, and will receive their first dose of open-label Compound I in the Extension Phase at the clinic and return to the clinic for trial visits at Weeks 56, 62 and 68, then every 12 weeks through Week 104. The Week 52 Visit activities will serve as Baseline for the Extension Phase. Subjects will return to the clinic for a Safety Follow-up Visit 4 weeks after the last dose of Compound I.

If a subject prematurely discontinues Compound I, he/she will be asked to remain in the trial, participating in the scheduled trial visits through Week 104. If a subject prematurely discontinues Compound I and does not wish to continue in the trial, he/she will be asked to return for a clinic visit and undergo the Week 104 assessments.

Inclusion Criteria for the Core Phase

Eligible subjects must meet/provide all of the following criteria:

Written informed consent.

Male or female ≥18 years of age at Screening.

Current diagnosis of IPF, as defined by ATS/ERS/JRS/ALAT guidelines [Raghu et al., Idiopathic pulmonary fibrosis (an update) and progressive pulmonary fibrosis in adults: an official ATS/ERS/JRS/ALAT Clinical Practice Guideline. Am J Respir Crit Care Med. 2022; 205(9):e18-47]; the date of initial diagnosis of IPF should be ≤7 years prior to Screening.

No recent changes or planned changes to the dose or regimen for IPF therapy, defined as: receiving a stable dose of IPF-approved therapy (i.e., nintedanib or pirfenidone) for a minimum of 3 months prior to Day 1 with no plans to change the background regimen during trial participation; or not currently receiving background IPF-approved therapy at Screening (either naive to IPF-approved therapy or previously discontinued any IPF-approved therapy at least 4 weeks prior to Day 1 or drug-specific, 5 half-lives elimination period if longer than 4 weeks), and with no current plans to restart treatment during trial participation. Subjects receiving any additional agent for IPF therapy must be on a stable regimen for at least 3 months prior to Day 1 with no current plans to change the treatment regimen during trial participation. Any previously discontinued therapy used to treat IPF must have been discontinued at least 4 weeks prior to Day 1 or 5 half-lives for that specific therapy must have elapsed, whichever is longer, with no plans to restart the therapy during trial participation.

Lung HRCT historically performed within 6 months prior to the Screening Visit and according to the minimum requirements for IPF diagnosis by central review based on subject's HRCT. If an evaluable HRCT is not available within 6 months prior to Screening, an HRCT will be performed at Screening to determine eligibility, according to the same requirements as the historical HRCT. The HRCT must demonstrate a usual interstitial pneumonia or probable usual interstitial pneumonia pattern based on central review vendor interpretation. Histopathology in combination with HRCT results supportive of an IPF or IPF likely diagnosis according to Raghu et al., 2022 can be submitted to support subject eligibility.

HRCT shows ≥10% to <50% parenchymal fibrosis (reticulation) and the extent of fibrotic changes is greater than the extent of emphysema on the most recent HRCT scan.

Meets all of the following criteria during the Screening Period, as determined by central review: FVC ≥45% predicted of normal; forced expiratory volume in 1 second (FEV1)/FVC ≥0.7; DLCO corrected for hemoglobin is ≥25% and ≤90% predicted of normal.

Estimated minimum life expectancy of ≥30 months for non-IPF-related disease, in the opinion of the Investigator.

Vaccinations are up to date.

Willing and able to comply with the prescribed treatment protocol and evaluations for the duration of the trial.

Exclusion Criteria for the Core Phase

Subjects will be ineligible for trial participation if they meet any of the following criteria: any of the following cardiovascular diseases: uncontrolled, severe hypertension (≥160/100 mmHg), within 6 months of Screening; myocardial infarction within 6 months of Screening unstable cardiac angina within 6 months of Screening.

ILD associated with known primary diseases (e.g., sarcoidosis, amyloidosis and coronavirus disease 2019 [COVID-19]), connective tissue disorders (e.g., rheumatoid arthritis, systemic lupus erythematosus, Sjogren's, dermatomyositis, scleroderma), exposures (e.g., radiation, silica, asbestos and coal dust) or drugs (e.g., amiodarone).

Known active bacterial, viral, fungal, mycobacterial or other infection, including tuberculosis or atypical mycobacterial disease (fungal infections of nail beds are allowed). The subject must be 3 months beyond any acute infection with COVID-19 if there has been a prior infection.

Clinically significant pulmonary hypertension requiring chronic medical therapy.

Use of any of the following therapies within 4 weeks prior to Screening, during the Screening Period or planned during the trial: prednisone at steady dose >10 mg/day or equivalent or cyclosporine. Change in regimen or dosage of any immunosuppressant during the Screening Period through the end of trial participation will require consultation with and approval by the trial Medical Monitor. Avoiding the use of listed prohibited treatments must not be considered detrimental and must be indicated by the treating physician. Subjects must not be withdrawn from any standard-of-care treatment that is considered necessary for the clinical management of the subject in order to fulfill the trial eligibility requirements.

Use of rifampin within 2 weeks prior to Day 1 or planned during the trial.

Malignant condition in the past 5 years (except successfully treated basal/squamous cell carcinoma of the skin or cervical cancer in situ).

Women of childbearing potential (WOCBP) or male subjects not agreeing to use highly effective method(s) of birth control throughout the trial and for 4 weeks after last dose of trial drug. Pregnant or lactating women and women who plan to become pregnant or breast feed during the trial and within 4 weeks after the last dose of trial drug.

Current drug or alcohol abuse or history of either within the previous 2 years, in the opinion of the Investigator or as reported by the subject.

Previous enrollment in this trial or participation in a prior Compound I clinical trial. Exposure to an experimental drug or experimental vaccine within either 30 days, 5 half-lives of the test agent, or twice the duration of the biological effect of the test agent, whichever is the longest, prior to Day 1.

Known history of positive test for human immunodeficiency virus (HIV). Active hepatitis.

Current alcoholic liver disease, primary biliary cirrhosis or primary sclerosing cholangitis.

Previous organ transplant (including allogeneic and autologous marrow transplant).

International normalized ratio >2, prolonged prothrombin time >1.5×the upper limit of normal (ULN) or partial thromboplastin time >1.5×ULN at Screening. Alanine aminotransferase (ALT) or aspartate aminotransferase (AST) >2.0×ULN. Estimated glomerular filtration rate <30 mL/min/1.73 m2 at Screening.

Any confirmed Grade 3 or higher laboratory abnormality. Any laboratory abnormality at Screening that, in the opinion of the Investigator, would preclude the subject's participation in the trial.

Any other condition that, in the opinion of the Investigator, would preclude enrollment in the trial.

Inclusion Criteria for the Extension Phase

Eligible subjects must meet/provide all of the following criteria:

Written informed consent.

Completed the Double-blind Treatment Period (Week 52) of the Core Phase of the trial; subjects prematurely discontinued from trial drug in the Core Phase of the trial for reasons other than safety or tolerability may be included at the discretion of the Investigator after completing scheduled visits, including Week 52 assessments.

Willing and able to comply with the prescribed treatment protocol and evaluations for the duration of the Extension Phase of the trial.

Exclusion Criteria for the Extension Phase

Subjects will be ineligible for trial participation if they meet any of the following criteria: anticipated use of another investigational agent for any condition during the course of the trial; new diagnosis of malignant condition after enrolling in Core Phase (except successfully treated basal/squamous cell carcinoma of the skin or cervical cancer in situ); estimated minimum life expectancy ≤18 months, in the opinion of the Investigator; WOCBP or male subjects not agreeing to use highly effective method(s) of birth control throughout the trial and for 1 month after last dose of Compound I; pregnant or lactating women; any other new development of the disease/condition/significant laboratory test abnormality during the course of the Core Phase of the trial, in the opinion of the Investigator, that would potentially put the subject at unacceptable risk; in the opinion of the Investigator, unlikely to comply with the trial protocol or has a concomitant disease or condition that could interfere with the conduct of the trial.

Treatments Administered

During the Core Phase of the trial, on Day 1 of the Double-blind Treatment Period, subjects will be randomized in a 1:1:1 ratio to receive for 52 weeks: Compound I 300 mg QD, or Compound I 300 mg BID, or Placebo.

During the Extension Phase, all subjects will receive open-label Compound I 300 mg BID for 52 weeks. The dose for the Extension Phase may be modified based on the results of the Core Phase.

Compound I will be provided as film-coated 150 mg tablets for oral administration.

Placebo tablets match the appearance of active tablets.

Subjects will take 2 Compound I 150 mg tablets orally in the morning and evening with a meal. The dose for the Extension Phase may be modified based on the results of the Core Phase.

Concomitant Therapy and Restricted Medications

Medication use restricted during the trial is presented in the following table:

| Medication | Restricted Time Period |
|---|---|
| Prednisone at steady dose >10 mg/day or equivalent or cyclosporine A | 4 weeks prior to Screening through trial completion Topical steroids for dermatological conditions and inhaled/intranasal/intra-articular steroids are allowed during the trial. Short bursts for acute illnesses (asthma, allergic reaction) are permitted |
| Other immunosuppressant agents | Treatment with any other immunosuppressant during the Screening Period through the end of trial participation will require consultation and approval by the trial Medical Monitor |
| Commercially approved agent for interstitial lung disease or an investigational agent for any condition | 90 days or 5 half-lives, whichever is longer, prior to Screening through trial completion |
| Drug/alcohol abuse | History of abuse within the past 2 years or abuse during trial |
| Rifampin* | 2 weeks prior to dosing through trial completion |
| OATP inhibitors: clarithromycin, erythromycin and gemfibrozil P-gp inhibitors: amiodarone, carvedilol, dronedarone, itraconazole, propafenone, quinidine, ranolazine and verapamil BCRP inhibitor: eltrombopag | 3 days prior to dosing through trial completion |

*Rifampicin is a CYP enzyme inducer and an OATP inhibitor.

In case of a clinically significant deterioration in lung function, initiation of additional therapy is allowed, as described in the table below, after Week 28. Clinically significant deterioration includes: An absolute decline since Baseline in FVC % predicted ≥10% or an absolute decline since Baseline in FVC % predicted ≥5 to 9% with associated decline in DLCO ≥15% since Baseline, or Clinically significant deterioration in other organ systems, per Investigator assessment.

DLCO=diffusing capacity of the lungs for carbon monoxide; FVC=forced vital capacity.

Other causes for FVC decline (i.e., respiratory tract infection) should be excluded. Repeat FVC/spirometry should be performed and confirmed prior to initiation of rescue medication if, to the Investigator's clinical judgment, well-founded doubts in the test's quality and the subject's good condition justify the associated delay in subject care, and the increase in risk for the subject.

Rescue Medications Allowed After Week 28 Due to Clinically Significant Deterioration

| Medication | Screening Period | Treatment and Post-treatment Follow-up Periods |
|---|---|---|
| | Non-steroidal medication | |
| Nintedanib | Not permitted | Not permitted except for deterioration* |
| Pirfenidone | Not permitted | Not permitted except for deterioration* |
| Mycophenolate mofetil/CellCept ≤3 g/day, Myfortic ≤2.14 g/day | Not permitted | Not permitted except for deterioration* |
| Cyclophosphamide | Not permitted for 4 weeks prior to Screening and throughout Screening | Not permitted except for deterioration* |
| | Steroids | |
| Prednisone >10 mg/day | Not permitted for 4 weeks prior to Screening and throughout Screening | Not permitted except for deterioration* |

*Initiation/change in dose permitted after the Week 28 Visit in case of clinically significant deterioration, defined as:
An absolute decline since Baseline in FVC % predicted ≥10% or an absolute decline since Baseline in FVC % predicted ≥5 to 9% with associated decline in DLCO ≥15% since Baseline, or
Clinically significant deterioration in other organ systems, per Investigator assessment. Other causes for FVC decline (i.e., respiratory tract infection) should be excluded. Repeat FVC/spirometry should be performed and confirmed prior to initiation of rescue medication if, to the Investigator's clinical judgment, well-founded doubts in the test's quality and the subject's good condition justify the associated delay in subject care, and the increase in risk for the subject.

Efficacy Variables

Spirometry

Spirometry, including FVC % predicted, will be assessed using a device provided by the Sponsor. Spirometry should only be performed by a trained assessor and the same assessor should complete the procedure for a given subject throughout the duration of the trial, unless it is not possible.

Spirometry measurements must be performed according to ATS/ERS 2019 guidelines [Graham et al., *Am J Respir Crit Care Med.* 2019; 200:e70-e88]. The test will be done in triplicate (3 curves to be provided) and the best result selected according to the guidelines. The best of 3 efforts will be defined as the highest FVC, obtained on any of the 3 blows meeting the ATS/ERS criteria with a maximum of 8 maneuvers.

Spirometry measurements should be attempted at approximately the same time of day from Baseline onwards. On days of clinic visits, subjects must refrain from strenuous activity at least 12 hours prior to pulmonary function testing. Smoking should be discouraged throughout the visit days and will not be permitted in the 30-minute period prior to spirometry. Subjects should also avoid cold temperatures, environmental smoke, dust or areas with strong odors (e.g., perfumes). If treated with bronchodilators, washout of 24 hours for long-acting and 8 hours for short-acting bronchodilators should be observed before spirometry.

Spirometry results will be electronically transmitted. To ensure the quality of primary endpoint measurement, a central spirometry review will occur. Results will be over-read by a central reader, confirmed by the clinical site and data will be transferred into the clinical database.

Rate the severity of your breathing problems over the last week: 0: no breathing problems; 1: mild breathing problems; 2: moderate breathing problems; 3: severe breathing problems; 4: very severe breathing problems.

How have your breathing problems changed since the start of the trial? +3: very much better; +2: much better; +1: a little better; 0: no change; −1: a little worse; −2: much worse; −3: very much worse.

6-Minute Walk Test

The 6MWT measures the distance a subject can quickly walk on a flat, hard surface in 6 minutes (6-minute walk distance). This test evaluates the global and integrated responses of all the systems involved during exercise, including the pulmonary and cardiovascular systems, systemic circulation, peripheral circulation, blood, neuromuscular units and muscle metabolism. The 6MWT will be performed according to ATS guidelines for the 6MWT [Lancaster, *Multidiscip Respir Med.* 2018; 13; 13:45].

Titrated Oxygen Requirement

Oxygen titration will be performed to determine the lowest oxygen flow rate required to maintain an oxygen saturation ($Sp,_{O2}$) of 296% in the standing position (TOR). Titration will begin with the subject breathing room air. $Sp,_{O2}$ will be monitored for 1 minute. If the $Sp,_{O2}$ is 296%, the test will conclude. If $Sp,_{O2}$ is <96%, the oxygen flow rate will be increased each minute to achieve a target $Sp,_{O2}$ of 296% using the following titration steps: 1, 2, 3, 4, 5, 6, 8, 12 and 15 $L \cdot min^{-1}$.

Diffusing Capacity of the Lungs for Carbon Monoxide

The site will use its own DLCO equipment and conduct all measurements with the same DLCO equipment in case that several devices are available at the site. Single-breath DLCO measurement will be carried out according to the ATS guideline on DLCO measurements [Graham et al., *Eur Respir J.* 2017; 49:16E00 16].

DLCO values will be adjusted for altitude, carboxyhemoglobin and the most recent hemoglobin value. The DLCO assessment should always be performed after the FVC measurement and should always be started approximately the same time each day.

Lung High-Resolution Computed Tomography

Lung HRCT will be reviewed by a central reader. These results must be available prior to randomization. If HRCT has been performed for clinical care in the 6 months prior to Screening and has been reviewed and deemed acceptable, then HRCT need not be performed at Screening.

Patient-Reported Outcome Assessments

Living with IPF

The L-IPF is a validated questionnaire that assesses symptoms, disease impacts and health-related quality of life in subjects with IPF [Swigris et al., 2020]. This questionnaire was developed with input from the FDA and comprises 2 modules: a 15-item symptom module with 3 domains (dyspnea, cough and energy), all with a 24-hour recall, and a 20-item impacts module with 1-week recall. All items in both modules have response options in a 5-point (0-4) numerical rating scale format.

King's Brief Interstitial Lung Disease Questionnaire

The K-BILD is a self-completed health status questionnaire comprising 15 items and a 7-point Likert response scale that was developed and validated specifically for patients with IPF [Patel et al., 2012]. This questionnaire has 3 domains: psychological, breathlessness and activities and chest symptoms. The K-BILD domains and total score range from 0 to 100; 100 represents best health status. The K-BILD scoring has recently changed with the introduction of a logit transformation step. The minimal clinically important difference for the K-BILD total score (logit version), as determined by both anchor and distribution-based methods, is a change of 5 units [Sinha et al., 2019].

Leicester Cough Questionnaire

The LCQ is a patient-reported questionnaire evaluating the impact of cough on quality of life. This questionnaire was originally developed for use in people with idiopathic chronic cough and has since been validated for use in people with bronchiectasis and chronic obstructive pulmonary disease [Birring et al., *Thorax.* 2003; 58:339-43].

The LCQ comprises 19 items and takes 5 to 10 minutes to complete. Each item assesses symptoms or the impact of symptoms over the last 2 weeks on a 7-point Likert scale. Scores in 3 domains (physical, psychological and social) are calculated as a mean for each domain (range: 1 to 7). A total score (range: 3 to 21) is also calculated by summing the domain scores. Higher scores indicate better quality of life.

SF-12 Health Survey

The SF-1 2 [Ware et al., Med Care. 1996; 34:220-33] is a 12-item survey used to assess general health-related quality of life. The SF-12 items are scored to generate a physical component score (PCS) and mental component score (MCS) from the subject's perspective. The SF-12 examines 8 domains of health outcomes, including physical functioning, role-physical, bodily pain, general health, vitality, social functioning, role-emotional and mental health. The SF-12 is a shorter version of the SF-36, which has accepted validity for use in subjects with IPF [Swigris et al., *Respir Med.* 2010; 104:296-304; Tomioka et al., *Intern Med.* 2007; 46:1533-42] and is 1 of 4 questionnaires used in the IPF Prospective Outcomes (IPF-PRO), an ongoing observational US registry of patients with confirmed IPF that records patient-reported outcomes.

The examples and embodiments described herein are for illustrative purposes only and various modifications or changes suggested to persons skilled in the art are to be included within the spirit and purview of this application and scope of the appended claims.

We claim:

1. A method of treating systemic sclerosis or lung disease in a subject in need thereof, comprising administering to the subject a therapeutically effective amount of 2-(4-methoxy-3-(3-methylphenethoxy)benzamido)-2,3-dihydro-1H-indene-2-carboxylic acid (Compound I), or a pharmaceutically acceptable salt thereof, wherein Compound I, or a pharmaceutically acceptable salt thereof, is administered with a meal and at a daily dose equivalent to at least about 300 mg/day of Compound I.

2. The method of claim 1, wherein Compound I is a crystalline form of Compound I (Form 1) and is characterized as having an X-ray powder diffraction (XRPD) pattern with peaks at 5.2 0.20 2-Theta, 9.0 0.20 2-Theta, 14.4+0.20 2-Theta, and 17.7 10.20 2-Theta, as measured using Cu (Ka) radiation.

3. The method of claim 2, wherein the crystalline form of Compound I (Form 1) comprises less than 1% w/w of crystalline Form 2 of Compound I.

4. The method of claim 1, wherein the systemic sclerosis is chosen from limited cutaneous systemic sclerosis, diffuse cutaneous systemic sclerosis, and systemic sclerosis sine scleroderma.

5. The method of claim 1, wherein the lung disease is lung fibrosis, interstitial lung disease (ILD), idiopathic interstitial pneumonia, connective tissue disease-associated interstitial lung disease (CTD-ILD), sarcoidosis, hypersensitivity pneumonitis, eosinophilic ILD, familial pulmonary fibrosis, idiopathic pulmonary fibrosis (IPF), non-specific interstitial pneumonia (NSIP), cryptogenic organizing pneumonia (COP), respiratory bronchiolitis interstitial lung disease (RBILD), desquamative interstitial pneumonia (DIP), acute interstitial pneumonia (AIP), or lymphoid interstitial pneumonia (LIP), or systemic sclerosis-associated interstitial lung disease (SSc-ILD).

6. The method of claim 1, wherein Compound I, or a pharmaceutically acceptable salt thereof, is administered for a period of at least about 24 consecutive weeks, at least about 36 consecutive weeks, or at least about 52 consecutive weeks.

7. The method of claim 1, wherein Compound I, or a pharmaceutically acceptable salt thereof, is administered orally.

8. The method of claim 1, wherein Compound I, or a pharmaceutically acceptable salt thereof, is administered at a dose equivalent to about 300 mg of Compound I once daily.

9. The method of claim 1, wherein Compound I, or a pharmaceutically acceptable salt thereof, is administered at a dose equivalent to about 300 mg of Compound I twice daily for a total daily dose equivalent to about 600 mg/day of Compound I.

10. The method of claim 1, wherein Compound I, or a pharmaceutically acceptable salt thereof, is administered in combination with a cough suppression medication, a corticosteroid, an immunosuppressant, N-acetyl cysteine (NAC), an anti-fibrotic therapeutic agent, or combinations thereof; or with N-acetyl cysteine, a corticosteroid, an immunosuppressant, pirfenidone, nintedanib, imatinib, a tyrosine kinase inhibitor, PBI-4050, recombinant pentraxin-2/SAP (PRM-151), aerosol IFN-y, an inhibitor of CTGF activity, a LPA receptor antagonist, an autotaxin inhibitor, a galectin-3 inhibitor, a LOXL2 inhibitor, tipelukast, an integrin antagonist, a PI3K inhibitor, a JNK inhibitor, a ROCK inhibitor, an anti-IL-13 compound, a CCL2 antagonist, a CCR2 antagonist, an anti-CD20 compound, an anticoagulant, a collagen V treatment, an ASK1 inhibitor, or combinations thereof; or with nintedanib, or a pharmaceutically acceptable salt thereof; or with pirfenidone.

11. The method of claim 1, wherein Compound I, or a pharmaceutically acceptable salt thereof, is administered in the form of a solid form pharmaceutical composition.

12. The method of claim 11, wherein the solid form pharmaceutical composition is a tablet, a pill, or a capsule.

13. The method of claim 1, wherein Compound I, or a pharmaceutically acceptable salt thereof, is administered in the form of one or more tablets.

14. The pharmaceutical composition of claim 13, wherein each tablet and comprises about 50 mg to about 300 mg of Compound I, or about 50 mg to about 150 mg of Compound I.

15. The method of claim 1, wherein the subject is an adult human.

16. A method of treating systemic sclerosis or lung disease in a subject in need thereof, comprising administering to the subject a therapeutically effective amount of 2-(4-methoxy-3-(3-methylphenethoxy)benzamido)-2,3-dihydro-1H-indene-2-carboxylic acid (Compound I), or a pharmaceutically acceptable salt thereof, wherein Compound I, or a pharmaceutically acceptable salt thereof, is administered orally in the form of a solid form pharmaceutical composition once or twice daily with a meal.

17. The method of claim 16, wherein Compound I, or a pharmaceutically acceptable salt thereof, is administered in the form of one or more tablets.

18. The method of claim 16, wherein Compound I, or a pharmaceutically acceptable salt thereof, is administered at a dose equivalent to about 300 mg of Compound I once daily, or at a dose equivalent to about 300 mg of Compound I twice daily for a total daily dose equivalent to about 600 mg/day of Compound I.

19. The method of claim 16, wherein Compound I, or a pharmaceutically acceptable salt thereof, is administered for a period of at least about 24 consecutive weeks, at least about 36 consecutive weeks, or at least about 52 consecutive weeks.

* * * * *